(12) United States Patent
Van Gorcom et al.

(10) Patent No.: US 6,350,602 B1
(45) Date of Patent: *Feb. 26, 2002

(54) CLONING AND EXPRESSION OF PHYTASE FROM ASPERGILLUS

(75) Inventors: Robert F. M. Van Gorcom; Willem Van Hartingsveldt, both of Delft; Petrus Andreas Van Paridon, Noordwijk; Annemarie Eveline Veenstra, Nieuw Vennep; Rudolf G. M. Luiten, Leiden; Gerardus C. M. Selten, Berkel en Rodenrijs, all of (NL)

(73) Assignee: DSM N.V., Te Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/233,510

(22) Filed: Jan. 20, 1999

Related U.S. Application Data

(63) Continuation of application No. 08/417,448, filed on Apr. 10, 1995, now Pat. No. 5,863,533, and a continuation of application No. 08/151,574, filed on Nov. 12, 1993, now Pat. No. 5,436,156, which is a continuation of application No. 07/688,578, filed as application No. PCT/NL90/00140 on Sep. 27, 1990.

(30) Foreign Application Priority Data

Sep. 27, 1989 (EP) .............................. 89202436
Aug. 17, 1990 (EP) .............................. 90202231

(51) Int. Cl.$^7$ .............................. C12N 9/16; C12N 1/20; C12N 15/63; C12P 21/06; C07H 21/04
(52) U.S. Cl. .................. 435/196; 435/69.1; 435/252.3; 435/320.1; 536/23.1; 536/23.2
(58) Field of Search .............................. 435/196, 69.1, 435/252.3, 320.1; 536/23.1, 23.2

(56) References Cited

U.S. PATENT DOCUMENTS 3,297,548 A   1/1967  Ware et al. .................. 435/196
5,436,156 A * 7/1995  Van Gorcom et al. ... 435/252.3

FOREIGN PATENT DOCUMENTS

EP    0 321 004    6/1986
EP    0 287 152    10/1988

OTHER PUBLICATIONS

Graf, E., ed., *Phytic Acid: Chemistry and Applications* (1986) Pilatus Press, Minneapolis, MN, Chapter 2, pp. 23–42.
Powar et al., *J. Bacteriol* 151(3):1102–1108 (1982).
Cosgrove, *Austral. J. Biol. Sci.* 23:1207–1220 (1970).
Nayini et al., *Lebensmittel Wissenschaft und Technologie* 17:24–26 (1984).
Yamada et al., *Agric. Biol. Chem.* 32(10):1275–1282 (1968).
Nelson et al., *J. Nutrition* 101:1289–1294 (1971).
Han, *Animal Feed Sci. & Technology* 24:345–350 (1989).
Product Information Brochure published by Alko Ltd., entitled "Finase™ Enzymes by Alko" Rajamaki, Finland, 4 pages total, Undated.
Ullah, *Preparative Biochem* 18(4):443–458 (1988).
Ullah, Enzyme and Engineering Conference IX, Oct. 4–8, 1987, Santa Barbara, CA (poster presentation) 2 pages total.
Ullah, *Preparatory Biochem.* 18(4)459–471 (1988).
Ullah, et al., *Preparatory Biochem.* 17(1):63–91 (1987).
Mullaney et al., Filamentous Fungi Conference (Apr., 1987) Pacific Grove, CA (poster presentation) 15 pages total.
Samson et al., *Nature* 318:191–194 1985.
Mullaney et al., "Positive identification of a lambda gt 11 clone containing a region of fungal phytase gene by immunoprobe and sequence verification", *Appl. Microbiol. Biotechnol.* 35:611–614 (1991).

\* cited by examiner

*Primary Examiner*—Ponnathapu Achutamurthy
*Assistant Examiner*—Peter P. Tung
(74) *Attorney, Agent, or Firm*—Morrison & Foerster LLP

(57) ABSTRACT

A nucleotide sequence encoding phytase has been isolated and cloned. The coding sequence has been inserted into an expression construct which in turn has been inserted into a vector capable of transforming a microbial expression host. The transformed microbial hosts may be used to economically produce phytase on an industrial scale. The phytase produced via the present invention may be used in a variety of processes requiring the conversion of phytate to inositol and inorganic phosphate.

24 Claims, 36 Drawing Sheets

N-TERMINAL AMINOACID SEQUENCES

| Position | A | B | C |
|---|---|---|---|
| 01 | | | LEU |
| 02 | | | ALA |
| 03 | | | VAL |
| 04 | | | PRO |
| 05 | | ALA | ALA |
| 06 | | SER | SER |
| 07 | | --- | ARG |
| 08 | ----** | --- | ASN |
| 09 | GLN | GLN | GLN |
| 10 | SER | SER | SER |
| 11 | SER | SER | SER |
| 12 | --- | --- | GLY |
| 13 | ASP | ASP | ASP |
| 14 | THR | THR | THR |
| 15 | VAL | VAL | VAL |
| 16 | ASP | ASP | ASP |
| 17 | GLN | GLN | |
| 18 | | GLY | |
| 19 | | TYR | |
| 20 | | GLN | |
| 21 | | ARG | |
| 22 | | PHE | |
| 23 | | SER | |
| 24 | | GLU | |
| 25 | | THR | |
| 26 | | SER | |
| 27 | | HIS | |
| 28 | | LEU | |
| 29 | | ARG | |
| 30 | | (GLY)* | |
| 31 | | GLN | |
| 32 | | TYR | |
| 33 | | ALA | |
| 34 | | PRO | |
| 35 | | PHE | |
| 36 | | PHE | |
| 37 | | (ASP) | |
| 38 | | LEU | |
| 39 | | ALA | |

Figure 1a

PEPTIDE AMINOACID SEQUENCES

| Position | A | B | C | D | E |
|---|---|---|---|---|---|
| 01 | GLN | (TRP)* | MET | ALA | VAL |
| 02 | ----** | SER | MET | SER | VAL |
| 03 | GLN | PHE | GLN | SER | ASP |
| 04 | ALA | ASP | CYS | ALA | --- |
| 05 | GLU | THR | GLN | GLU | ARG |
| 06 | GLN | ILE | ALA | LYS | PHE |
| 07 | GLU | SER | GLU | GLY | PRO |
| 08 | PRO | THR | GLN | TYR | TYR |
| 09 | LEU | SER | GLU | ASP | THR |
| 10 | VAL | THR | PRO | LEU | GLY |
| 11 | (ARG) | VAL | LEU | VAL | --- |
| 12 | VAL | ASP | VAL | VAL | ALA |
| 13 | LEU | THR | ARG | | |
| 14 | VAL | LYS | VAL | | |
| 15 | ASN | LEU | LEU | | |
| 16 | (ASP) | SER | VAL | | |
| 17 | (ARG) | PRO | ASN | | |
| 18 | (VAL) | PHE | ASP | | |
| 19 | VAL | (CYS) | ARG | | |
| 20 | PRO | (ASP) | | | |
| 21 | | LEU | | | |
| 22 | | PHE | | | |
| 23 | | THR | | | |

Figure 1b

N-TERMINUS 100KD PROTEIN

Position
| | |
|---|---|
| 01 | VAL |
| 02 | VAL |
| 03 | ASP |
| 04 | GLU |
| 05 | ARG |
| 06 | PHE |
| 07 | PRO |
| 08 | TYR |
| 09 | THR |
| 10 | GLY |

```
                 1   2   3   4   5   6   7   8   9   10  11  12  13  14  15  16  17  18  19  20
Peptide C: Leu-Ala-Val-Pro-Ala-Ser-Arg-Asn-Gln-Ser-Ser-Gly-Asp-Ser-Thr-Val-Asp
Peptide B:                     Ala-Ser-***-***-Gln-Ser-***-Asp-Gln-Gly-Tyr-Gln-
Peptide A:                                 *-Gln-Ser-Ser-*-Asp-Thr-Val-Asp-Gln Possible
codons:5' CTG-GCG-GTG-CCG-GCG-TCG-CGG-AAT-CAA-TCG-TCG-GGG-GAT-ACG-GTG-GAT-CAA-GGG-TAT- CAA-
           A   A   A   A   A   A   A       G   A   A   C   A   C   A   A   C   A   C   G
           T   T   T   T   T   T   T               T   T       T   T   T   T   T
           C   C   C   C   C   C   C               C   C       C   C   C   C   C
                                     TTA               AGT AGT
                                     G         AGT AGA    C   C
                                                 C   G AB1024:  3'-CGG-CAG-GGG-CGG-CGG-TCG-GCG-TTG-GTC-TCG-TCG-CCG-CTG-TGG-CAC-CTG-GTC
AB1065:                      3'-CCG-CTG-TGG-CAC-CTG-GTC
                                                     A
AB1066:                                              G
AB1067:                                          A
AB1068:                                      A
AB1069:                              A
AB1070:                              A       A   A   G       A
AB1226:                                                              3'-CAG-CTG-GTC-CCG-ATG-GTC
                                                                         C   A
AB1227:                                                              3'-CAG-CTG-GTC-CCG-ATG-GTC
                                                                         C   A   T   A   A   T
                                                                             A
AB1298:                                                              3'-CTG-TGG-CAG-CTG-GTG-CCG-ATG-GTC
                                                                         A   C   C   A   T   C   A   T
```

(phytase N-terminus, continued)

Peptide B:
```
         21  22  23  24  25  26  27  28  29  30  31  32  33  34  35  36  37  38  39
        (Arg)Phe-Ser-Glu-Thr-Ser-His-Leu-Arg-(Gly)-Gln-Tyr-Ala-Pro-Phe-Phe-(Asp)-Leu-Ala
         CGG-TTT-TCG-GAG-ACG-TCG-CAT-CTG-CGG- GGG- CAG-TAT-CGC-CCG-TTT-TTT- GAT- CTG-GCG
          T   T   A   A   A   A   A   T   T    A     T   A   C   C   C   C    C    A   A
          T   T   C   A   T   T   T   C   C    T     T   C   T   T   T   C    C    T   T
          C   C   C                                  C   A                    T    C   C
         AGG AGT     AGT         TTG AGG          TTG  A                           TTG  A
          A   C                   A   A           A
```

AB1388:
```
                                                            3'-CCG-GTC- ATG-CGG-GGG- AAG- AAG-  CTG- GA
                                                                                C    C           A
```

Peptide A: (Gln- ? -Gln-Ala-Glu-Gln-Glu-Pro-Leu-Val-(Ser/Arg)-Val-Leu-Val-(Asp/Asn)

```
       1   2   3   4   5   6   7   8   9  10  11  12  13  14  15
      CAG-???-CAG-GCG-GAG-CAG-GAG-CCG-CTG-GTG-(TCG/CGG)-GTG-CTG-GTG-(GAT/AAT)
       A       A   A   A   A   T   A   T   A       A      A   A   A     C
                               C       C   C       C      C   C   C     T
                                           TTG     AGT    AGG  TTG      C
                                            A       C               A
```

AB1295:    3'- GTC. CGC.CTC. GTC. CTC. GGG. GAG. CA -5'
                T    G    T    T    T   C A C

```
        16        17       18  19  20  21  22
      -Asp/Thr/Arg-(Arg/Val)-Val-Pro-(Pro)-Met-Gly
      -GAT/ACG/CGG-(CGG/GTG)-GTG-CCG-(CCG)-ATG-GGG
       C   A   A    A   A    A   A    A    T
       T   T   T    T   T    T   T    C    C
       C   C   C    C   C    C   C    C
       AGG AGG               A
            A
```

```
              1   2   3   4   5   6   7   8   9  10  11  12  13  14  15  16  17  18
Peptide B: (Trp)-Ser-Phe-Asp-Thr-Ile-Ser-Thr-Ser-Thr-Val-Asp-Thr-Lys-Leu-Ser-Pro-Phe- (TGG)-TCG-TTT-GAT-ACG-ATA-TCG-ACG-TCG-ACG-GTG-GAT-ACG-AAG-CTG-TCG-CCG-TTT-
                A   C   C   A   T   A   A   A   A   C   A   A   A   A   A   A   C
                T       T   C   C   T   T   T   T       T   T   T       T   T   T
                C           C       C   C   C   C       C   C   C       C   C   C
               AGT                         AGT                         TTG AGT
                C                           C                           A   C AB1296 :    3'-AAG. CTG.TGC. TAG.AGG. TGG.AGG. TGG. CAC. CTG. TGC. TTC-5'
                                       TCC    C TCC   C                    AB1297:  3'-GGC.AAG.
                                                                                          G 19  20  21  22  23  24  25  26  27  28  29  30  31  32  33
            (Cys)-(Asp)-Leu-Phe-Thr-(Thr)-(Asp)-(Glu)-(Cys)-Ile)-(Cys)-(Thr/Asn)-(Tyr)-(Arg/Gly)-(Tyr)-Leu (GTG)-(GAT)- CTG- TTT- ACG-(ACG)-(GAT)- GAG) - (TGT)-(ATA)-(ACG/AAT) - (TAT)-(CGG / GGG)-(TAT)-CTG
          C    C      A    C    A    A    T     A     C     T     A     C      A     A          C     A
                      T         C    T              C                    C      T                T     T
                      C         C    C         C                                C                C     C
                     TTG                       AGG                                                TTG
                      A                         A                                                       A (ACG). (CTG). GAG. AAG. TGC. (TGC). (CTG). (CTC). (ACG).(TAG).(T)-5'
                     C                 G Figure 2b (sheet 2 of 2 )
```

```
 1   2   3   4   5   6   7   8   9  10  11  12  13  14  15  16  17  18  19  20  21  22  23
Phe-Ser-Tyr-Gly-Ala-Ala-Ile-Pro-Gln-Ser-Thr-Gln-Glu-Lys-Gln-Phe-Ser-Gln-Glu-Phe-Arg-Asp-Gly

5'-TTT-TCG-TAT-GGG-GCG-GCG-ATA-CCG-CAG-TCG-ACG-CAG-GAG-AAG-CAG-TTT-TCG-CAG-GAG-TTT-CGG-GAT-GGG
        C   A   C   A   A   T   A   A   A   A   A   A   A   A   A   C   A   A   A   C   A
        T           T   T   C   T   T       T   T                   T           T   T   T
        C           C   C       C   C       C   C                   C   AGT     C   C   C
       AGT                                                              AGT     AGG
                                            C                           C       C

AB1025: 3'-ATG-CCG-CGG-CGG-TAG-GGG-GTC-TCG-TGG-GTC-CTC-TTC-GTC-CTC-GTC-AAG-TCG-GTC-CTC-AAG-GC-5'
AB1026:                                     3'-GTC-CTC-TTC-GTC-CTC-GTC-AAG-TCG-GTC-CTC-AAG-GC-5'
                                                               T       AGA     T
                                                                       C       C

AB1027: 3'-ATG-CCG-GCG-CGC-TAA-GGC-GTC-5'
           A   T   T   G   G
               A   A
               G   G
```

```
GTCGACTTCCCGTCCTATTCGGCCTCGTCCGCTGAAGATCCATCCCACCA
 SalI
TTGCACGTGGGCCACCTTTGTGAGCTTCTAACCTGAACTGGTAGAGTATC     100

ACACACCATGCCAAGGTGGGATGAAGGGGTTATATGAGACCGTCCGGTCC

GGCGCGATGGCCGTAGCTGCCACTCGCTGCTGTGCAAGAAATTACTTCTC     200

ATAGGCATCATGGGCGTCTCTGCTGTTCTACTTCCTTTGTATCTCCTGTC
         translation start
TGGGTATGCTAAGCACCACAATCAAAGTCTAATAAGGACCCTCCCTTCCG     300
    start<--------------------------------------

AGGGCCCCTGAAGCTCGGACTGTGTGGGACTACTGATCGCTGACTATCTG
--intron-----------------------------------------

TGCAGAGTCACCTCCGGACTGGCAGTCCCCGCCTCGAGAAATCAATCCAG     400
->end
TTGCGATACGGTCGATCAGGGGTATCAATGCTTCTCCGAGACTTCGCATC

TTTGGGGTCAATACGCACCGTTCTTCTCTGGCAAACGAATCGGTCATC      500

TCCCCTGAGGTGCCCGCCGGATGCAGAGTCACTTTCGCTCAGGTCCTCTC

CCGTCATGGAGCGCGGTATCCGACCGACTCCAAGGGCAAGAAATACTCCG     600

CTCTCATTGAGGAGATCCAGCAGAACGCGACCACCTTTGACGGAAAATAT

GCCTTCCTGAAGACATACAACTACAGCTTGGGTGCAGATGACCTGACTCC     700

CTTCGGAGAACAGGAGCTAGTCAACTCCGGCATCAAGTTCTACCAGCGGT

ACGAATCGCTCACAAGGAACATCGTTCCATTCATCCGATCCTCTGGCTCC     800

AGCCGCGTGATCGCCTCCGGCAAGAAATTCATCGAGGGCTTCCAGAGCAC

CAAGCTGAAGGATCCTCGTGCCCAGCCCGGCCAATCGTCGCCCAAGATCG     900
         BamHI
ACGTGGTCATTTCCGAGGCCAGCTCATCCAACAACACTCTCGACCCAGGC

ACCTGCACTGTCTTCGAAGACAGCGAATTGGCCGATACCGTCGAAGCCAA     1000
```

```
TTTCACCGCCACGTTCGTCCCTCCATTCGTCAACGTCTGGAGAACGACC

TGTCCGGTGTGACTCTCACAGACACAGAAGTGACCTACCTCATGGACATG    1100

TGCTCCTTCGACACCATCTCCACCAGCACCGTCGACACCAAGCTGTCCCC
                                   SalI
CTTCTGTGACCTGTTCACCCATGACGAATGGATCAACTACGACTACCTCC    1200

AGTCCTTGAAAAGTATTACGGCCATGGTGCAGGTAACCCGCTCGGCCCG

ACCCAGGGCGTCGGCTACGCTAACGAGCTCATCGCCCGTCTGACCCACTC    1300

GCCTGTCCACGATGACACCAGTTCCAACCACACTTTGGACTCGAGCCCGG

CTACCTTTCCGCTCAACTCTACTCTCTACGCGGACTTTTCGCATGACAAC    1400

GGCATCATCTCCATTCTCTTTGCTTTAGGTCTGTACAACGGCACTAAGCC

GCTATCTACCACGACCGTGGAGAATATCACCCAGACAGATGGATTCTCGT    1500

CTGCTTGGACGGTTCCGTTTGCTTCGCGTTTGTACGTCGAGATGATGCAG

TGTCAGGCGGAGCAGGAGCCGCTGGTCCGTGTCTTGGTTAATGATCGCGT    1600

TGTCCCGCTGCATGGGTGTCCGGTTGATGCTTTGGGGAGATGTACCCGGG

ATAGCTTTGTGAGGGGGTTGAGCTTTGCTAGATCTGGGGGTGATTGGGCG    1700

GAGTGTTTTGCTTAGCTGAATTACCTTGATGAATGGTATGTATCACATTG
translation stop
CATATCATTAGCACTTCAGGTATGTATTATCGAAGATGTATATCGAAAGG    1800

ATCAATGGTGACTGTCACTGGTTATCTGAATATCCCTCTATACCTCGTCC

CACAACCAATCATCACCCTTTAAACAATCACACTCAACGCACAGCGTACA    1900

AACGAACAAACGCACAAGAATATTTTACACTCCTCCCCAACGCAATACC

AACCGCAATTCATCATACCTCATATAAATACAATACAATACAATACATCC    2000
```

```
ATCCCTACCCTCAAGTCCACCCATCCTATAATCAATCCCTACTTACTTAC

TTCTCCCCCTCCCCCTCACCCTTCCCAGAACTCACCCCCGAAGTAGTAAT    2100

AGTAGTAGTAGAAGAAGCAGACGACCTCTCCACCAATCTCTTCGGCCTCT

TATCCCCATACGCTACACAAACCCCCACCCCGTTAGCATGCACTCAGAA     2200

AATAATCAAAAATAACTAAGAAGGAAAAAAAGAAGAAGAAAGGTTACAT

ACTCCTCTCATACAAACTCCAAGACGTATACATCAAGATGGGCAATCCCA    2300

CCATTACTGATATCCATCTATGAACCCATTCCCATCCCACGTTAGTTGAT

TACTTTACTTAGAAGAAGAAAAAGGGAAGGGAAGGGAAAGAAGTGGATGG    2400

GATTGAGTTAGTGCTCACCGTCTCGCAGCAAGTTTATATTCTTTTGTTTG

GCGGATATCTTTCACTGCTCCTGCTGGACGTTGTCACGGGGTGGTAGTGG    2500

TTGGCGGTGGTGAGGGTCCATGATCACTCTTGGTTTGGGGGGTTGTTGTT

GTCGTTGTTGTTGTTGGGTGGGCATTTTCTTTTCTTCACTTGGGGAT      2600

TATTATTTGGAATTGGTTAGTTTGAGTGAGTGGGTAATATTGAATGGGTG

ATTATTGGGAATGAAGTAGATTTGGCTATGAATGGTTGATGGGATGGAAT    2700

GAATGGATGGATGAATAGATGGAGGCGGAAAAGTCAGGTGGTTTGAGGTT

CGGATTATTATCTTTGTGCCTGAGGCATCACTCTCCATCTATGTTGTTCT    2800

TTCTATACCGATCTACCAGAGCTAAGTTGACTGATTCTACCACAGTGCAC

AATAAGTATGTACTTATTTCATTTAGAGTATTTAGATTAACCCGCTGTGC    2900

TATTTGCCGTAGCTTTCCACCCAATTTCGAAGTTCGAAGAATTAAAACTC

ATCCTACAGTACAGAATAGAAGTAAAAGGAGAAGAGAAAAACAAGATAAT    3000
```

```
ACAACCAGTCCAGGTCCATTCTAGATCTCGAATGACCACCAAATAAGAAA

GCAACAAGCAAGTAAGCAAAGCATAAGTCTAAATGAACGCCAATAACTTC    3100

ATCGCCTGCCTTTGAAACTGAACGCTATGCACGAATGGCTCGAAATGATT

CCCTTAACTCCGTAGTATTGAGAGTGAGAGGAAAAGAAAAAAGAGACAG     3200

AAAAGCTGACCATGGGAAAGAAGCATGATCAGTCGGGAATGGATCTGCGG

GTTGAGATAGATATGAGTTGCCTCGCAGATCCGGTGACAAGATAAGAGAA    3300

TTGGGAGATGTGATCAGCCACTGTAACTTCATCAAGCATCGACATTCAAC

CGTCGGGTCTGCGGGTTGAGATGCAAGTTGAGATGCCACGCAGACCCGAA    3400

CAGAGTGAGAGATGTGAGACTTTTGAACCACTGTGACTTCATCAAGCATC

AAAACACACTCCATGGTCAATCGGTTAGGGTGTGAGGGTTGATATGCCAG    3500

GTTCGATGCCACGCAGACCCGAACCGACTGAGAAATATGAAAAGTTGGAC

AGCCACTTCATCTTCATCAAGCGTAAAACCCCAATCAATGGTAAATCGAA    3600

AACGAATCTGCGGGCTGATGTGGAAATGAGACGAATGCCTCGCAGATTCG

AAGACACGTAAATCGAGATGAACAATCACTTTAACTTCATCAAAGCCTTA    3700

AATCACCCAATGGCCAGTCTATTCGGGTCTGCGGGTTGAGGTTCCTGTTG

AGATGCCACGCAGACTGCGAACATGCGATGCATTATAAGTTGGACGAGTG    3800

TAGACTGACCATTGATAACCGAGATAAACAATCACTTCAACTTCATCAAA

GCCTTAAATCACTCAATGGCCAGTCTGTTTGCGGTCTGCGGGCTGATACC    3900

CAAGTTGCGATGCCACGCAGACTGCAAACATTGATCGAGAGACGAGAAAA

ACAACGCACTTTAACTTCAACAAAAGCCTTTCAATCAGTCAATGGCCAGT    4000
```

```
CTGTTCGCGGTCTGCGGGCTGATATGCGAGTTGAGGTGCCTCGCAGACCG

CGAACATGCGATGTAATTTCTTAGTTAGACGAGTGCCTGGCCATTGAGAA    4100

ACGAGAGAAACAACCACTTTAACTTCATGAAAGCCTTGAACTACTCAATG

ACCCGTCTGTTGGCGGTCTGCGGGCTGATATTCGAGTTGAGATGCCACGC    4200

AGACCGCCAACATGCGATGTATCATGTAAGTTAGATGAGTGACTGGCCAT

TGAGAAACGAGAGAAACAACCACACTTCATGAGAGCCTTAAATTATTCAA    4300

TGACCAGTCTGTTCACGGTCTGCGGGTTGGTATGCGAGTCGAGGTGCCTC

GCAGACCGCGAACATGCGATGTTTTCGATGGACGAGTGAAGCCTGACGAT    4400

CGAGAACTATCTCAGTTGGGTTGGCCATTCGGCTGGCCGTTGGGTTTAGT

ATTAGGATCGTCAGGTTTGTCCGATGGAACGTTCCGTTTGCGTGCGTTGG    4500

CGCGACGAGCCCTCTCCTCGGCGTGATTCTGAAATTCTGCAATCAGGGCA

GCCGCAGCACGGCGACGGGACGTCCTCCAGGAGCTGTGTTGAAGTTTCGG    4600

GGTGGCGGTCCAGAAGGGGGAGTTACATTAAAAGCCTCATAGATGTCTTT

GGGTGGTTCCGGGGGGCCCATCGCAAGATCTTCTGGAGTTGTGCGTCTGA    4700

TCATCTCTTGAGTGTAATTGCGACGCAGACCGAGCTTCAGGATTTTGGAA

GGGCTGGATCGCTCCTGCTGACTCTTTCCCTCAGCGGGCTTCGTCTCGGC    4800

AGTCTTCATTTCGGCGGGCTGATCTTCCATCTCAGAATGGGATCGCTTTC

TGGTCGCTGCACCCGCTCCTCCCTTCAAGGTCAGCTTGATGCGCAGCGTC    4900

TTGGGCGGCTCAGCTGGTGGAGTTGGTTCCGGCTCTGGCTCCCTCCGGCG

TCGCTTGGGCACTTGAGTAGTCTCTGAGGCTTCGCCGCGGCGCCGTTTGC    5000
```

```
GAGTCGGCTCCTTGGTCTCTTTGGCCTCTTTCACTTCACCTGGACCGTCT
TTCGGGGCGGTTTCATCGTGCTGAGCGATCAAGGTTTGGATGTAGGCAGC    5100
CGGCATCATTCGATCAACGGCAATTCCTCTCTTGCGGGCCTCCTCCCGAG
CCTTGATTGTCGCCTTGACCTCGTCCACGTTTTCGAAGAAGAAAGGCATC    5200
TTGTTATCCTGAGGCAAGTTGCGCTCTCCCATGCGTGGGGATATCCGAAG
ATGCGGTCCTTCTCGAACTGTTCATGAGACTTCAGACGAATTGGAGGCTG    5300
GGGGAGCAATTTGTCTCCGTAGGTGTTGTTAGGGCGGAACCAAGAATAGC
CTTCGCCTACAACGACAAGCTCTTCGCCAAATTTATTTTTTGGCCTGTA    5400
AAAACGAACCCATCCTCGTCAGTCCACCGGTGCGTCTCGGACGTAGAGAT
TGGCTTACTTATTCCCTCAACGCCGATCTCTGCCTGGGGCTGCGCTTCGG    5500
ATGCGGCCTCGGTCACGGCTCCGCCTCGGACTGCACCGCTGGAGTTTCGG
TCTTCTTCTCCTGCTTCTCCAGGTACTCCTTGCGTAACTCTTCGATCAGC    5600
CTCGGCTTCCGATGACTGCTCAAATTCTGGAGCAACAGCTGCCGCGGCCA
GGTCAAGCAGGCGGTTTGCTAAAACTGCCCATTTTCCATCGACACCTGCC    5700
TCCGACGCCTGTGCAAAACCAGCTGTTTTCGCATTGGCCTGTTTGTTGGC
ACGCGTCTTCTTGACTGCTGCCTTGCCCTTTACTTCCTTGAGAGCAGACT    5800
CTGGCTTAGATGATGGTGCACGGTTTCTGCGGAAGCGCCGCTCAGATTCC
AAAGATTCCATAGCTTTAATGGTAGGCTTTCTGGTTCTTCCAGAAGTGCG    5900
CGCAGCTGACGTAGTGGTTGAGTAGCTGGCAGTTGGGGATCCTGGGCCCT
CATTGGAACCATCAAGACCAAATTTGTTTCCATACATATCAGCATGGTAT    6000
```

```
TCAAAAGGAAAACTTTCGCCGTACGGAGTACTGCGTTCGATTCCGGGTGT

ATCCAAGTCGTATCCAGACATGGTGTCGAATTCAGCCTTGCTGTCAAGAG    6100

CAGGGGTACTTTCAATGCTGTCAGCAACCACGCGGCCAAAGGGCGTCTTC

GGGAAGAAGGTGTTTCAAGAGAAGCGTCATCCACGGCCTGGCTTGCGGC    6200

GTTGATTGCAGACTTTCGAGTAGATCGCTGAGGTCGCGAACTGGTTCGAG

TAGCAACCTGTGAATTGGCAGCCTTGTGACTGCTTCGATTCACTGCAGAG    6300

ACGGAGTAGACTGCACTGATTTGGAATTCTGAGTCGCAGCCATTCTGGAT

TTGCGTTCGGCGCGACGAGATCTCGCAGTCGTGGTACGAGGAGTAGAGCG    6400

AGGCTGCGTAGCAGTGTTGCAAGCTTGGTGCTAGCCTCCTGGGCTTCAGC

AGCTTCAGCAGTGGTGGCAGACGCAGCAGAATTAGCGGAGCTTTATCGGC    6500

TTTGCCGCTCTGAGCGTTGGGAGTAGAAGTGAGAGAAGAGGTAGAGTCCA

CGGAAGAAGTCTTCTCGCTGTTCTCAAAGCCGTTCAGCTTTGCTGGCATA    6600

GACTTACGCGTCTTGCGGCTGTTGGAAGCGGAAGAGTTCATGGCGGGAGA

GGAGACGTTAGAAGTAGACATGGTGGGGTTTGTTGACGGGTTTTGAGTAA    6700

CAAGAGACTTGCGTCGATCTTTGAGTGTTCTTGACAGAAAGTTATGCAAC
```

<u>GTCGAC</u>  6756
 SalI

```
ATGGGCGTCTCTGCTGTTCTACTTCCTTTGTATCTCCTGTCTGGAGTCAC
 M  G  V  S  A  V  L  L  P  L  Y  L  L  S  G  V  T
-23        -20            '                    -10

CTCCGGACTGGCAGTCCCCGCCTCGAGAAATCAATCCAGTTGCGATACGG      100
  S   L  A  V  P  A  S  R  N  Q  S  S  C  D  T
   '          -1 +1              '              10

TCGATCAGGGGTATCAATGCTTCTCCGAGACTTCGCATCTTTGGGGTCAA
 V  D  Q  G  Y  Q  C  F  S  E  T  S  H  L  W  G  Q
          '              20                      '

TACGCACCGTTCTTCTCTCTGGCAAACGAATCGGTCATCTCCCCTGAGGT      200
  Y  A  P  F  F  S  L  A  N  E  S  V  I  S  P  E  V
     30              '                    40

GCCCGCCGGATGCAGAGTCACTTTCGCTCAGGTCCTCTCCCGTCATGGAG
    P  A  G  C  R  V  T  F  A  Q  V  L  S  R  H  G
  '           50              '                60

CGCGGTATCCGACCGACTCCAAGGGCAAGAAATACTCCGCTCTCATTGAG      300
 A  R  Y  P  T  D  S  K  G  K  K  Y  S  A  L  I  E
           '              70                     '

GAGATCCAGCAGAACGCGACCACCTTTGACGGAAAATATGCCTTCCTGAA
 E  I  Q  Q  N  A  T  T  F  D  G  K  Y  A  F  L  K
    80              '                   90

GACATACAACTACAGCTTGGGTGCAGATGACCTGACTCCCTTCGGAGAAC      400
  T  Y  N  Y  S  L  G  A  D  D  L  T  P  F  G  E
   '         100              '              110

AGGAGCTAGTCAACTCCGGCATCAAGTTCTACCAGCGGTACGAATCGCTC
 Q  E  L  V  N  S  G  I  K  F  Y  Q  R  Y  E  S  L
          '             120                      '

ACAAGGAACATCGTTCCATTCATCCGATCCTCTGGCTCCAGCCGCGTGAT      500
  T  R  N  I  V  P  F  I  R  S  S  G  S  S  R  V  I
    130                            140

CGCCTCCGGCAAGAAATTCATCGAGGGCTTCCAGAGCACCAAGCTGAAGG
 A  S  G  K  K  F  I  E  G  F  Q  S  T  K  L  K
   '         150              '              160

ATCCTCGTGCCCAGCCCGGCCAATCGTCGCCCAAGATCGACGTGGTCATT      600
 D  P  R  A  Q  P  G  Q  S  S  P  K  I  D  V  V  I
          '             170                      '

TCCGAGGCCAGCTCATCCAACAACACTCTCGACCCAGGCACCTGCACTGT
  S  E  A  S  S  S  N  N  T  L  D  P  G  T  C  T  V
    180                '                  190

CTTCGAAGACAGCGAATTGGCCGATACCGTCGAAGCCAATTTCACCGCCA      700
   F  E  D  S  E  L  A  D  T  V  E  A  N  F  T  A
  '          200              '                210
```

```
CGTTCGTCCCCTCCATTCGTCAACGTCTGGAGAACGACCTGTCCGGTGTG
 T  F  V  P  S  I  R  Q  R  L  E  N  D  L  S  G  V
              '           220              '

ACTCTCACAGACACAGAAGTGACCTACCTCATGGACATGTGCTCCTTCGA    800
 T  L  T  D  T  E  V  T  Y  L  M  D  M  C  S  F  D
       230           '           240

CACCATCTCCACCAGCACCGTCGACACCAAGCTGTCCCCCTTCTGTGACC
 T  I  S  T  S  T  V  D  T  K  L  S  P  F  C  D
    '           250              '           260

TGTTCACCCATGACGAATGGATCAACTACGACTACCTCCAGTCCTTGAAA    900
 L  F  T  H  D  E  W  I  N  Y  D  Y  L  Q  S  L  K
              '           270              '

AAGTATTACGGCCATGGTGCAGGTAACCCGCTCGGCCCGACCCAGGGCGT
 K  Y  Y  G  H  G  A  G  N  P  L  G  P  T  Q  G  V
       280              '           290

CGGCTACGCTAACGAGCTCATCGCCCGTCTGACCCACTCGCCTGTCCACG    1000
    G  Y  A  N  E  L  I  A  R  L  T  H  S  P  V  H
    '           300              '           310

ATGACACCAGTTCCAACCACACTTTGGACTCGAGCCCGGCTACCTTTCCG
 D  D  T  S  S  N  H  T  L  D  S  S  P  A  T  F  P
              '           320              '

CTCAACTCTACTCTCTACGCGGACTTTTCGCATGACAACGGCATCATCTC    1100
 L  N  S  T  L  Y  A  D  F  S  H  D  N  G  I  I  S
       330              '           340

CATTCTCTTTGCTTTAGGTCTGTACAACGGCACTAAGCCGCTATCTACCA
 I  L  F  A  L  G  L  Y  N  G  T  K  P  L  S  T
    '           350              '           360

CGACCGTGGAGAATATCACCCAGACAGATGGATTCTCGTCTGCTTGGACG    1200
 T  T  V  E  N  I  T  Q  T  D  G  F  S  S  A  W  T
              '           370              '

GTTCCGTTTGCTTCGCGTTTGTACGTCGAGATGATGCAGTGTCAGGCGGA
 V  P  F  A  S  R  L  Y  V  E  M  M  Q  C  Q  A  E
       380              '           390

GCAGGAGCCGCTGGTCCGTGTCTTGGTTAATGATCGCGTTGTCCCGCTGC    1300
    Q  E  P  L  V  R  V  L  V  N  D  R  V  V  P  L
    '           400              '           410

ATGGGTGTCCGGTTGATGCTTTGGGGAGATGTACCCGGGATAGCTTTGTG
 H  G  C  P  V  D  A  L  G  R  C  T  R  D  S  F  V
              '           420              '

AGGGGGTTGAGCTTTGCTAGATCTGGGGGTGATTGGGCGGAGTGTTTTGC    1400
 R  G  L  S  F  A  R  S  G  G  D  W  A  E  C  F  A
       430              '           440

TTAG                                                  1404
```

A

```
                      SEQUENCE LISTING (1) GENERAL INFORMATION:

(iii) NUMBER OF SEQUENCES: 52

(2) INFORMATION FOR SEQ ID NO:1:

(i) SEQUENCE CHARACTERISTICS:
         (A) LENGTH: 9 amino acids
         (B) TYPE: amino acid
         (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:1:

Gln Ser Ser Xaa Asp Thr Val Asp Gln
1               5

(2) INFORMATION FOR SEQ ID NO:2:

(i) SEQUENCE CHARACTERISTICS:
         (A) LENGTH: 35 amino acids
         (B) TYPE: amino acid
         (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:2:

Ala Ser Xaa Xaa Gln Ser Ser Xaa Asp Thr Val Asp Gln Gly Tyr Gln
1               5                   10                  15

Arg Phe Ser Glu Thr Ser His Leu Arg Xaa Gln Tyr Ala Pro Phe Phe
                20                  25                  30

Asp Leu Ala
        35

(2) INFORMATION FOR SEQ ID NO:3:

(i) SEQUENCE CHARACTERISTICS:
         (A) LENGTH: 10 amino acids
         (B) TYPE: amino acid
         (D) TOPOLOGY: linear
```

(ii) MOLECULE TYPE: peptide (iii) HYPOTHETICAL: NO (v) FRAGMENT TYPE: N-terminal (xi) SEQUENCE DESCRIPTION: SEQ ID NO:3:

Val Val Asp Glu Arg Phe Pro Tyr Thr Gly
1               5                   10

(2) INFORMATION FOR SEQ ID NO:4:

(i) SEQUENCE CHARACTERISTICS:
             (A) LENGTH: 20 amino acids
             (B) TYPE: amino acid
             (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:4:

Gln Xaa Gln Ala Glu Gln Glu Pro Leu Val Arg Val Leu Val Asn Asp
1               5                   10                  15

Arg Val Val Pro
            20

(2) INFORMATION FOR SEQ ID NO:5:

(i) SEQUENCE CHARACTERISTICS:
             (A) LENGTH: 23 amino acids
             (B) TYPE: amino acid
             (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:5:

Xaa Ser Phe Asp Thr Ile Ser Thr Ser Thr Val Asp Thr Lys Leu Ser
1               5                   10                  15

Pro Phe Cys Asp Leu Phe Thr
            20

(2) INFORMATION FOR SEQ ID NO:6:

(i) SEQUENCE CHARACTERISTICS:
             (A) LENGTH: 16 amino acids
             (B) TYPE: amino acid
             (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:6:

Leu Ala Val Pro Ala Ser Arg Asn Gln Ser Ser Gly Asp Thr Val Asp
1               5                   10                  15

(2) INFORMATION FOR SEQ ID NO:7:

(i) SEQUENCE CHARACTERISTICS:

(A) LENGTH: 19 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:7:

Met Met Gln Cys Gln Ala Glu Gln Glu Pro Leu Val Arg Val Leu Val
1               5                   10                  15

Asn Asp Arg (2) INFORMATION FOR SEQ ID NO:8:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:8:

Ala Ser Ser Ala Glu Lys Gly Tyr Asp Leu Val Val
1               5                   10

(2) INFORMATION FOR SEQ ID NO:9:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:9:

Val Val Asp Xaa Arg Phe Pro Tyr Thr Gly Xaa Ala
1               5                   10

(2) INFORMATION FOR SEQ ID NO:10:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (iii) HYPOTHETICAL: YES (vi) ORIGINAL SOURCE:
            Phytase N-terminus reverse
            translation (xi) SEQUENCE DESCRIPTION: SEQ ID NO:10:

YTNGCNGTNC CNGCNWSNMG NAAYCARWSN WSNGGNGAYA CNGTNGAYCA RGGNTAYCAR      60

MGNTTWWWSA RACNWSNCAW YTNMGNGGNC ARTAYGCNCC NTTYTTYGAY YTNGCN         116

(2) INFORMATION FOR SEQ ID NO:11:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (iii) HYPOTHETICAL: YES (vi) ORIGINAL SOURCE:
        internal fragment A (Phytase)
        reverse translation (xi) SEQUENCE DESCRIPTION: SEQ ID NO:11:

```
CARNNNCARG CRGANCARGA RCCRYTNGTN HSNGTNYTNG TNRAYVVNVK NGTNCCNCCN    60

ATGGGN                                                              66
```

(2) INFORMATION FOR SEQ ID NO:12:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: DNA (iii) HYPOTHETICAL: YES (vi) ORIGINAL SOURCE:
        internal fragment B (Phytase)
        reverse translation (xi) SEQUENCE DESCRIPTION: SEQ ID NO:12:

```
TGGWSNTTYG AYACNATHWS NACNWSNACN GTNGAYACNA ARYTNWSNCC NTTYTCYGAY    60

YTNTTYACNA CNGAYGARTG YATHAMNTAY VGNTAYYTN                          99
```

(2) INFORMATION FOR SEQ ID NO:13:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (iii) HYPOTHETICAL: YES (vi) ORIGINAL SOURCE:
        alkaline phosphatase reverse
        translation (xi) SEQUENCE DESCRIPTION: SEQ ID NO:13:

```
TTYWSNTAYG GNGCNGCNAT HCCNCARWSN ACNCARGARA ARCARTTYWS NCARGARTTY    60

MGNGAYGGN                                                           69
```

(2) INFORMATION FOR SEQ ID NO:14:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (synthetic)

```
        (iii) HYPOTHETICAL: NO (vi) ORIGINAL SOURCE:
              AB1024

(xi) SEQUENCE DESCRIPTION: SEQ ID NO:14:

CTGGTCGACG GTGTCGCCGC TGCTCTGGTT GCGGCTGGCG GGGACGGC                48

(2) INFORMATION FOR SEQ ID NO:15:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: DNA (synthetic)

(iii) HYPOTHETICAL: NO (vi) ORIGINAL SOURCE:
              AB1065

(xi) SEQUENCE DESCRIPTION: SEQ ID NO:15:

CTGRTCCACG GTGTCGCC                                                 18

(2) INFORMATION FOR SEQ ID NO:16:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: DNA (synthetic)

(iii) HYPOTHETICAL: NO (vi) ORIGINAL SOURCE:
              AB1066

(xi) SEQUENCE DESCRIPTION: SEQ ID NO:16:

CTGRTCGACG GTGTCGCC                                                 18

(2) INFORMATION FOR SEQ ID NO:17:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: DNA (synthetic)

(iii) HYPOTHETICAL: NO (vi) ORIGINAL SOURCE:
              AB1067

(xi) SEQUENCE DESCRIPTION: SEQ ID NO:17:

CTGRTCCACA GTGTCGCC                                                 18

(2) INFORMATION FOR SEQ ID NO:18:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: DNA (synthetic)
```

(iii) HYPOTHETICAL: NO (vi) ORIGINAL SOURCE:
         AB1069

(xi) SEQUENCE DESCRIPTION: SEQ ID NO:18:

CTGRTCCACG GTATCGCC                                                    18

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (vi) ORIGINAL SOURCE:
         AB1069

(xi) SEQUENCE DESCRIPTION: SEQ ID NO:19:

CTGGTCCACG GTGTCACC                                                    18

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (vi) ORIGINAL SOURCE:
         AB1070

(xi) SEQUENCE DESCRIPTION: SEQ ID NO:20:

CTGATCGACA GTATCACC                                                    18

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (vi) ORIGINAL SOURCE:
         AB1226

(xi) SEQUENCE DESCRIPTION: SEQ ID NO:21:

CTGGTARCCC TGRTCSAC                                                    18

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear

```
         (ii) MOLECULE TYPE: DNA (synthetic)

(iii) HYPOTHETICAL: NO (vi) ORIGINAL SOURCE:
              AB1227

(xi) SEQUENCE DESCRIPTION: SEQ ID NO:22:

YTGRTADCCY TGRTCVAC                                                        18

(2) INFORMATION FOR SEQ ID NO:23:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (synthetic)

(iii) HYPOTHETICAL: NO (vi) ORIGINAL SOURCE:
              AB1298

(xi) SEQUENCE DESCRIPTION: SEQ ID NO:23:

YTGRTASCCK TGRTCSACSG TRTC                                                 24

(2) INFORMATION FOR SEQ ID NO:24:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (synthetic)

(iii) HYPOTHETICAL: NO (vi) ORIGINAL SOURCE:
              AB1388

(xi) SEQUENCE DESCRIPTION: SEQ ID NO:24:

ARGTCGAAGA ASGGSGCGTA CTGSCC                                               26

(2) INFORMATION FOR SEQ ID NO:25:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: DNA (synthetic)

(iii) HYPOTHETICAL: NO (vi) ORIGINAL SOURCE:
              AB1295

(xi) SEQUENCE DESCRIPTION: SEQ ID NO:25:

ACSARSGGYT CYTGYTCSGC YTG                                                  23

(2) INFORMATION FOR SEQ ID NO:26:

(i) SEQUENCE CHARACTERISTICS:
              (A) LENGTH: 36 base pairs
              (B) TYPE: nucleic acid
              (C) STRANDEDNESS: single
              (D) TOPOLOGY: linear
```

(ii) MOLECULE TYPE: DNA (synthetic)

(iii) HYPOTHETICAL: NO (vi) ORIGINAL SOURCE:
                AB1296

(xi) SEQUENCE DESCRIPTION: SEQ ID NO:26:

CTTCGTGTCC ACSGTSSWSG TSSWGATCGT GTCGAA                                    36

(2) INFORMATION FOR SEQ ID NO:27:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA (synthetic)

(iii) HYPOTHETICAL: NO (vi) ORIGINAL SOURCE:
                AB1297

(xi) SEQUENCE DESCRIPTION: SEQ ID NO:27:

TGATGCACTC GTCSGTSGTG AASAGGTCGC AGAASGG                                   37

(2) INFORMATION FOR SEQ ID NO:28:

(i) SEQUENCE CHARACTERISTICS:
            (A) LENGTH: 56 base pairs
            (B) TYPE: nucleic acid
            (C) STRANDEDNESS: single
            (D) TOPOLOGY: linear (ii) MOLECULE TYPE: DNA (synthetic)

(iii) HYPOTHETICAL: NO (vi) ORIGINAL SOURCE:
                AB1025

(xi) SEQUENCE DESCRIPTION: SEQ ID NO:28:

CGGAACTCCT GGCTGAACTG CTTCTCCTGG GTGCTCTGGG GGATGGCGGC GCCGTA            56

(2) INFORMATION FOR SEQ ID NO:29:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (synthetic)

(iii) HYPOTHETICAL: NO (vi) ORIGINAL SOURCE:
                AB1026

(xi) SEQUENCE DESCRIPTION: SEQ ID NO:29:

CGGAAYTCCT GVSWGAACTG CTTYTCCTG                                           29

(2) INFORMATION FOR SEQ ID NO:30:

(i) SEQUENCE CHARACTERISTICS:
            (A) LENGTH: 21 base pairs
            (B) TYPE: nucleic acid
            (C) STRANDEDNESS: single (D) TOPOLOGY: linear (ii) MOLECULE TYPE: DNA (synthetic)

(iii) HYPOTHETICAL: NO (vi) ORIGINAL SOURCE:
            AB1027

(xi) SEQUENCE DESCRIPTION: SEQ ID NO:30:

CTGSGGRATN GCNCGRCCGT A                                               21

(2) INFORMATION FOR SEQ ID NO:31:

(i) SEQUENCE CHARACTERISTICS:
        (A) LENGTH: 6756 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Aspergillus ficuum (Aspergillus niger)
        (B) STRAIN: NRRL 3135

(vii) IMMEDIATE SOURCE:
        (A) LIBRARY: lambda AF
        (B) CLONE: pAF2-3, pAF2-6, pAF2-7

(ix) FEATURE:
        (A) NAME/KEY: exon
        (B) LOCATION: 210..253

(ix) FEATURE:
        (A) NAME/KEY: intron
        (B) LOCATION: 254..355

(ix) FEATURE:
        (A) NAME/KEY: exon
        (B) LOCATION: 356..1715

(ix) FEATURE:
        (A) NAME/KEY: CDS
        (B) LOCATION: join(210..253, 356..1715)
        (D) OTHER INFORMATION: /codon_start= 210
            /product= "Phytase"

(ix) FEATURE:
        (A) NAME/KEY: sig_peptide
        (B) LOCATION: 210..380

(ix) FEATURE:
        (A) NAME/KEY: mat_peptide
        (B) LOCATION: 381..1712
        (C) IDENTIFICATION METHOD: experimental
        (D) OTHER INFORMATION: /function= "inositol phosphate
            phosphatase"
            /product= "Phytase"
            /evidence= EXPERIMENTAL (xi) SEQUENCE DESCRIPTION: SEQ ID NO:31:

GTCGACTTCC CGTCCTATTC GGCCTCGTCC GCTGAAGATC CATCCCACCA TTGCACGTGG        60

GCCACCTTTG TGAGCTTCTA ACCTGAACTG GTAGAGTATC ACACACCATG CCAAGGTGGG       120

ATGAAGGGGT TATATGAGAC CGTCCGGTCC GGCGCGATGG CCGTAGCTGC CACTCGCTGC       180

TGTGCAAGAA ATTACTTCTC ATAGGCATC ATG GGC GTC TCT GCT GTT CTA CTT        233
                                Met Gly Val Ser Ala Val Leu Leu
                                -23             -20

```
CCT TTG TAT CTC CTG TCT  GG GTATGCTAAG CACCACAATC AAAGTCTAAT        283
Pro Leu Tyr Leu Leu Ser  Gly
-15                 -10

AAGGACCCTC CCTTCCGAGG GCCCCTGAAG CTCGGACTGT GTGGGACTAC TGATCGCTGA   343

CTATCTGTGC AG A GTC ACC TCC GGA CTG GCA GTC CCC GCC TCG AGA AAT     392
             Val Thr Ser Gly Leu Ala Val Pro Ala Ser Arg Asn
              -8          -5                              1

CAA TCC AGT TGC GAT ACG GTC GAT CAG GGG TAT CAA TGC TTC TCC GAG     440
Gln Ser Ser Cys Asp Thr Val Asp Gln Gly Tyr Gln Cys Phe Ser Glu
 5              10                  15                      20

ACT TCG CAT CTT TGG GGT CAA TAC GCA CCG TTC TTC TCT CTG GCA AAC     488
Thr Ser His Leu Trp Gly Gln Tyr Ala Pro Phe Phe Ser Leu Ala Asn
                25                  30                  35

GAA TCG GTC ATC TCC CCT GAG GTG CCC GCC GGA TGC AGA GTC ACT TTC     536
Glu Ser Val Ile Ser Pro Glu Val Pro Ala Gly Cys Arg Val Thr Phe
                40                  45                  50

GCT CAG GTC CTC TCC CGT CAT GGA GCG CGG TAT CCG ACC GAC TCC AAG     584
Ala Gln Val Leu Ser Arg His Gly Ala Arg Tyr Pro Thr Asp Ser Lys
            55                  60                  65

GGC AAG AAA TAC TCC GCT CTC ATT GAG GAG ATC CAG CAG AAC GCG ACC     632
Gly Lys Lys Tyr Ser Ala Leu Ile Glu Glu Ile Gln Gln Asn Ala Thr
        70                  75                  80

ACC TTT GAC GGA AAA TAT GCC TTC CTG AAG ACA TAC AAC TAC AGC TTG     680
Thr Phe Asp Gly Lys Tyr Ala Phe Leu Lys Thr Tyr Asn Tyr Ser Leu
 85             90                  95                     100

GGT GCA GAT GAC CTG ACT CCC TTC GGA GAA CAG GAG CTA GTC AAC TCC     728
Gly Ala Asp Asp Leu Thr Pro Phe Gly Glu Gln Glu Leu Val Asn Ser
                105                 110                 115

GGC ATC AAG TTC TAC CAG CGG TAC GAA TCG CTC ACA AGG AAC ATC GTT     776
Gly Ile Lys Phe Tyr Gln Arg Tyr Glu Ser Leu Thr Arg Asn Ile Val
            120                 125                 130

CCA TTC ATC CGA TCC TCT GGC TCC AGC CGC GTG ATC GCC TCC GGC AAG     824
Pro Phe Ile Arg Ser Ser Gly Ser Ser Arg Val Ile Ala Ser Gly Lys
        135                 140                 145

AAA TTC ATC GAG GGC TTC CAG AGC ACC AAG CTG AAG GAT CCT CGT GCC     872
Lys Phe Ile Glu Gly Phe Gln Ser Thr Lys Leu Lys Asp Pro Arg Ala
    150                 155                 160

CAG CCC GGC CAA TCG TCG CCC AAG ATC GAC GTG GTC ATT TCC GAG GCC     920
Gln Pro Gly Gln Ser Ser Pro Lys Ile Asp Val Val Ile Ser Glu Ala
165                 170                 175                 180

AGC TCA TCC AAC AAC ACT CTC GAC CCA GGC ACC TGC ACT GTC TTC GAA     968
Ser Ser Ser Asn Asn Thr Leu Asp Pro Gly Thr Cys Thr Val Phe Glu
                185                 190                 195

GAC AGC GAA TTG GCC GAT ACC GTC GAA GCC AAT TTC ACC GCC ACG TTC     1016
Asp Ser Glu Leu Ala Asp Thr Val Glu Ala Asn Phe Thr Ala Thr Phe
            200                 205                 210

GTC CCC TCC ATT CGT CAA CGT CTG GAG AAC GAC CTG TCC GGT GTG ACT     1064
Val Pro Ser Ile Arg Gln Arg Leu Glu Asn Asp Leu Ser Gly Val Thr
        215                 220                 225

CTC ACA GAC ACA GAA GTG ACC TAC CTC ATG GAC ATG TGC TCC TTC GAC     1112
Leu Thr Asp Thr Glu Val Thr Tyr Leu Met Asp Met Cys Ser Phe Asp
    230                 235                 240

ACC ATC TCC ACC AGC ACC GTC GAC ACC AAG CTG TCC CCC TTC TGT GAC     1160
Thr Ile Ser Thr Ser Thr Val Asp Thr Lys Leu Ser Pro Phe Cys Asp
245                 250                 255                 260

CTG TTC ACC CAT GAC GAA TGG ATC AAC TAC GAC TAC CTC CAG TCC TTG     1208
Leu Phe Thr His Asp Glu Trp Ile Asn Tyr Asp Tyr Leu Gln Ser Leu
                265                 270                 275

AAA AAG TAT TAC GGC CAT GGT GCA GGT AAC CCG CTC GGC CCG ACC CAG     1256
```

```
               Lys Lys Tyr Tyr Gly His Gly Ala Gly Asn Pro Leu Gly Pro Thr Gln
                       280                 285                 290

GGC GTC GGC TAC GCT AAC GAG CTC ATC GCC CGT CTG ACC CAC TCG CCT              1304
Gly Val Gly Tyr Ala Asn Glu Leu Ile Ala Arg Leu Thr His Ser Pro
            295                 300                 305

GTC CAC GAT GAC ACC AGT TCC AAC CAC ACT TTG GAC TCG AGC CCG GCT              1352
Val His Asp Asp Thr Ser Ser Asn His Thr Leu Asp Ser Ser Pro Ala
        310                 315                 320

ACC TTT CCG CTC AAC TCT ACT CTC TAC GCG GAC TTT TCG CAT GAC AAC              1400
Thr Phe Pro Leu Asn Ser Thr Leu Tyr Ala Asp Phe Ser His Asp Asn
325                 330                 335                 340

GGC ATC ATC TCC ATT CTC TTT GCT TTA GGT CTG TAC AAC GGC ACT AAG              1448
Gly Ile Ile Ser Ile Leu Phe Ala Leu Gly Leu Tyr Asn Gly Thr Lys
                345                 350                 355

CCG CTA TCT ACC ACG ACC GTG GAG AAT ATC ACC CAG ACA GAT GGA TTC              1496
Pro Leu Ser Thr Thr Thr Val Glu Asn Ile Thr Gln Thr Asp Gly Phe
            360                 365                 370

TCG TCT GCT TGG ACG GTT CCG TTT GCT TCG CGT TTG TAC GTC GAG ATG              1544
Ser Ser Ala Trp Thr Val Pro Phe Ala Ser Arg Leu Tyr Val Glu Met
        375                 380                 385

ATG CAG TGT CAG GCG GAG CAG GAG CCG CTG GTC CGT GTC TTG GTT AAT              1592
Met Gln Cys Gln Ala Glu Gln Glu Pro Leu Val Arg Val Leu Val Asn
390                 395                 400

GAT CGC GTT GTC CCG CTG CAT GGG TGT CCG GTT GAT GCT TTG GGG AGA              1640
Asp Arg Val Val Pro Leu His Gly Cys Pro Val Asp Ala Leu Gly Arg
405                 410                 415                 420

TGT ACC CGG GAT AGC TTT GTG AGG GGG TTG AGC TTT GCT AGA TCT GGG              1688
Cys Thr Arg Asp Ser Phe Val Arg Gly Leu Ser Phe Ala Arg Ser Gly
                425                 430                 435

GGT GAT TGG GCG GAG TGT TTT GCT TAGCTGAATT ACCTTGATGA ATGGTATGTA             1742
Gly Asp Trp Ala Glu Cys Phe Ala
            440                 445

TCACATTGCA TATCATTAGC ACTTCAGGTA TGTATTATCG AAGATGTATA TCGAAAGGAT            1802

CAATGGTGAC TGTCACTGGT TATCTGAATA TCCCTCTATA CCTCGTCCCA CAACCAATCA            1862

TCACCCTTTA AACAATCACA CTCAACGCAC AGCGTACAAA CGAACAAACG CACAAAGAAT            1922

ATTTTACACT CCTCCCCAAC GCAATACCAA CCGCAATTCA TCATACCTCA TATAAATACA            1982

ATACAATACA ATACATCCAT CCCTACCCTC AAGTCCACCC ATCCTATAAT CAATCCCTAC            2042

TTACTTACTT CTCCCCCTCC CCCTCACCCT TCCCAGAACT CACCCCCGAA GTAGTAATAG            2102

TAGTAGTAGA AGAAGCAGAC GACCTCTCCA CCAATCTCTT CGGCCTCTTA TCCCCATACG            2162

CTACACAAAA CCCCCACCCC GTTAGCATGC ACTCAGAAAA TAATCAAAAA TAACTAAGAA            2222

GGAAAAAAAA GAAGAAGAAA GGTTACATAC TCCTCTCATA CAAACTCCAA GACGTATACA            2282

TCAAGATGGG CAATCCCACC ATTACTGATA TCCATCTATG AACCCATTCC CATCCCACGT            2342

TAGTTGATTA CTTTACTTAG AAGAAGAAAA AGGGAAGGGA AGGGAAAGAA GTGGATGGGA            2402

TTGAGTTAGT GCTCACCGTC TCGCAGCAAG TTTATATTCT TTTGTTTGGC GGATATCTTT            2462

CACTGCTCCT GCTGGACGTT GTCACGGGGT GGTAGTGGTT GGCGGTGGTG AGGGTCCATG            2522

ATCACTCTTG GTTTGGGGGG TTGTTGTTGT CGTTGTTGTT GTTGTTGGGT GGGCATTTTC            2582

TTTTCTTCAC TTGGGGATTA TTATTTGGAA TTGGTTAGTT TGAGTGAGTG GGTAATATTG            2642

AATGGGTGAT TATTGGGAAT GAAGTAGATT TGGCTATGAA TGGTTGATGG GATGGAATGA            2702

ATGGATGGAT GAATAGATGG AGGCGGAAAA GTCAGGTGGT TTGAGGTTCG GATTATTATC            2762

TTTGTGCCTG AGGCATCACT CTCCATCTAT GTTGTTCTTT CTATACCGAT CTACCAGAGC           2822
```

```
TAAGTTGACT GATTCTACCA CAGTGCACAA TAAGTATGTA CTTATTTCAT TTAGAGTATT    2882
TAGATTAACC CGCTGTGCTA TTTGCCGTAG CTTTCCACCC AATTTCGAAG TTCGAAGAAT    2942
TAAAACTCAT CCTACAGTAC AGAATAGAAG TAAAAGGAGA AGAGAAAAAC AAGATAATAC    3002
AACCAGTCCA GGTCCATTCT AGATCTCGAA TGACCACCAA ATAAGAAAGC AACAAGCAAG    3062
TAAGCAAAGC ATAAGTCTAA ATGAACGCCA ATAACTTCAT CGCCTGCCTT TGAAACTGAA    3122
CGCTATGCAC GAATGGCTCG AAATGATTCC CTTAACTCCG TAGTATTGAG AGTGAGAGGA    3182
AAAGAAAAAA AGAGACAGAA AAGCTGACCA TGGGAAAGAA GCATGATCAG TCGGGAATGG    3242
ATCTGCGGGT TGAGATAGAT ATGAGTTGCC TCGCAGATCC GGTGACAAGA TAAGAGAATT    3302
GGGAGATGTG ATCAGCCACT GTAACTTCAT CAAGCATCGA CATTCAACGG TCGGGTCTGC    3362
GGGTTGAGAT GCAAGTTGAG ATGCCACGCA GACCCGAACA GAGTGAGAGA TGTGAGACTT    3422
TTGAACCACT GTGACTTCAT CAAGCATCAA ACACACTCC ATGGTCAATC GGTTAGGGTG    3482
TGAGGGTTGA TATGCCAGGT TCGATGCCAC GCAGACCCGA ACCGACTGAG AAATATGAAA    3542
AGTTGGACAG CCACTTCATC TTCATCAAGC GTAAAACCCC AATCAATGGT AAATCGAAAA    3602
CGAATCTGCG GGCTGATGTG GAAATGAGAC GAATGCCTCG CAGATTCGAA GACACGTAAA    3662
TCGAGATGAA CAATCACTTT AACTTCATCA AAGCCTTAAA TCACCCAATG GCCAGTCTAT    3722
TCGGGTCTGC GGGTTGAGGT TCCTGTTGAG ATGCCACGCA GACTGCGAAC ATGCGATGCA    3782
TTATAAGTTG GACGAGTGTA GACTGACCAT TGATAACCGA GATAAACAAT CACTTCAACT    3842
TCATCAAAGC CTTAAATCAC TCAATGGCCA GTCTGTTTGC GGTCTGCGGG CTGATACCCA    3902
AGTTGCGATG CCACGCAGAC TGCAAACATT GATCGAGAGA CGAGAAAAAC AACGCACTTT    3962
AACTTCAACA AAAGCCTTTC AATCAGTCAA TGGCCAGTCT GTTCGCGGTC TGCGGGCTGA    4022
TATGCGAGTT GAGGTGCCTC GCAGACCGCG AACATGCGAT GTAATTTCTT AGTTAGACGA    4082
GTGCCTGGCC ATTGAGAAAC GAGAGAAACA ACCACTTTAA CTTCATGAAA GCCTTGAACT    4142
ACTCAATGAC CCGTCTGTTG GCGGTCTGCG GGCTGATATT CGAGTTGAGA TGCCACGCAG    4202
ACCGCCAACA TGCGATGTAT CATGTAAGTT AGATGAGTGA CTGGCCATTG AGAAACGAGA    4262
GAAACAACCA CACTTCATGA GAGCCTTAAA TTATTCAATG ACCAGTCTGT TCACGGTCTG    4322
CGGGTTGGTA TGCGAGTCGA GGTGCCTCGC AGACCGCGAA CATGCGATGT TTTCGATGGA    4382
CGAGTGAAGC CTGACGATCG AGAACTATCT CAGTTGGGTT GGCCATTCGG CTGGCCGTTG    4442
GGTTTAGTAT TAGGATCGTC AGGTTTGTCC GATGGAACGT TCCGTTTGCG TGCGTTGGCG    4502
CGACGAGCCC TCTCCTCGGC GTGATTCTGA AATTCTGCAA TCAGGGCAGC CGCAGCACGG    4562
CGACGGGACG TCCTCCAGGA GCTGTGTTGA AGTTTCGGGG TGGCGGTCCA GAAGGGGGAG    4622
TTACATTAAA AGCCTCATAG ATGTCTTTGG GTGGTTCCGG GGGGCCCATC GCAAGATCTT    4682
CTGGAGTTGT GCGTCTGATC ATCTCTTGAG TGTAATTGCG ACGCAGACCG AGCTTCAGGA    4742
TTTTGGAAGG GCTGGATCGC TCCTGCTGAC TCTTTCCCTC AGCGGGCTTC GTCTCGGCAG    4802
TCTTCATTTC GGCGGGCTGA TCTTCCATCT CAGAATGGGA TCGCTTTCTG GTCGCTGCAC    4862
CCGCTCCTCC CTTCAAGGTC AGCTTGATGC GCAGCGTCTT GGGCGGCTCA GCTGGTGGAG    4922
TTGGTTCCGG CTCTGGCTCC CTCCGGCGTC GCTTGGGCAC TTGAGTAGTC TCTGAGGCTT    4982
CGCCGCGGCG CCGTTTGCGA GTCGGCTCCT TGGTCTCTTT GGCCTCTTTC ACTTCACCTG    5042
GACCGTCTTT CGGGCGGTT  TCATCGTGCT GAGCGATCAA GGTTTGGATG TAGGCAGCCG    5102
GCATCATTCG ATCAACGGCA ATTCCTCTCT TGCGGGCCTC CTCCCGAGCC TTGATTGTCG    5162
CCTTGACCTC GTCCACGTTT TCGAAGAAGA AAGGCATCTT GTTATCCTGA GGCAAGTTGC    5222
```

-continued

```
GCTCTCCCAT GCGTGGGGAT ATCCGAAGAT GCGGTCCTTC TCGAACTGTT CATGAGACTT    5282

CAGACGAATT GGAGGCTGGG GGAGCAATTT GTCTCCGTAG GTGTTGTTAG GGCGGAACCA    5342

AGAATAGCCT TCGCCTACAA CGACAAGCTC TTCGCCAAAT TTATTTTTTT GGCCTGTAAA    5402

AACGAACCCA TCCTCGTCAG TCCACCGGTG CGTCTCGGAC GTAGAGATTG GCTTACTTAT    5462

TCCCTCAACG CCGATCTCTG CCTGGGGCTG CGCTTCGGAT GCGGCCTCGG TCACGGCTCC    5522

GCCTCGGACT GCACCGCTGG AGTTTCGGTC TTCTTCTCCT GCTTCTCCAG GTACTCCTTG    5582

CGTAACTCTT CGATCAGCCT CGGCTTCCGA TGACTGCTCA AATTCTGGAG CAACAGCTGC    5642

CGCGGCCAGG TCAAGCAGGC GGTTTGCTAA AACTGCCCAT TTTCCATCGA CACCTGCCTC    5702

CGACGCCTGT GCAAAACCAG CTGTTTTCGC ATTGGCCTGT TTGTTGGCAC GCGTCTTCTT    5762

GACTGCTGCC TTGCCCTTTA CTTCCTTGAG AGCAGACTCT GGCTTAGATG ATGGTGCACG    5822

GTTTCTGCGG AAGCGCCGCT CAGATTCCAA AGATTCCATA GCTTTAATGG TAGGCTTTCT    5882

GGTTCTTCCA GAAGTGCGCG CAGCTGACGT AGTGGTTGAG TAGCTGGCAG TTGGGGATCC    5942

TGGGCCCTCA TTGGAACCAT CAAGACCAAA TTTGTTTCCA TACATATCAG CATGGTATTC    6002

AAAAGGAAAA CTTTCGCCGT ACGGAGTACT GCGTTCGATT CCGGGTGTAT CCAAGTCGTA    6062

TCCAGACATG GTGTCGAATT CAGCCTTGCT GTCAAGAGCA GGGGTACTTT CAATGCTGTC    6122

AGCAACCACG CGGCCAAAGG GCGTCTTCGG GAAAGAAGGT GTTTCAAGAG AAGCGTCATC    6182

CACGGCCTGG CTTGCGGCGT TGATTGCAGA CTTTCGAGTA GATCGCTGAG GTCGCGAACT    6242

GGTTCGAGTA GCAACCTGTG AATTGGCAGC CTTGTGACTG CTTCGATTCA CTGCAGAGAC    6302

GGAGTAGACT GCACTGATTT GGAATTCTGA GTCGCAGCCA TTCTGGATTT GCGTTCGGCG    6362

CGACGAGATC TCGCAGTCGT GGTACGAGGA GTAGAGCGAG GCTGCGTAGC AGTGTTGCAA    6422

GCTTGGTGCT AGCCTCCTGG GCTTCAGCAG CTTCAGCAGT GGTGGCAGAC GCAGCAGAAT    6482

TAGCGGAGCT TTATCGGCTT TGCCGCTCTG AGCGTTGGGA GTAGAAGTGA GAAGAGGT     6542

AGAGTCCACG GAAGAAGTCT TCTCGCTGTT CTCAAAGCCG TTCAGCTTTG CTGGCATAGA    6602

CTTACGCGTC TTGCGGCTGT TGGAAGCGGA AGAGTTCATG GCGGGAGAGG AGACGTTAGA    6662

AGTAGACATG GTGGGGTTTG TTGACGGGTT TTGAGTAACA AGAGACTTGC GTCGATCTTT    6722

GAGTGTTCTT GACAGAAAGT TATGCAACGT CGAC                                6756
```

(2) INFORMATION FOR SEQ ID NO:32:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO:32:

```
Met Gly Val Ser Ala Val Leu Leu Pro Leu Tyr Leu Leu Ser Gly Val
-23         -20             -15             -10

Thr Ser Gly Leu Ala Val Pro Ala Ser Arg Asn Gln Ser Ser Cys Asp
        -5               1               5

Thr Val Asp Gln Gly Tyr Gln Cys Phe Ser Glu Thr Ser His Leu Trp
 10              15              20              25

Gly Gln Tyr Ala Pro Phe Phe Ser Leu Ala Asn Glu Ser Val Ile Ser
                30              35              40

Pro Glu Val Pro Ala Gly Cys Arg Val Thr Phe Ala Gln Val Leu Ser
            45              50              55
```

```
Arg His Gly Ala Arg Tyr Pro Thr Asp Ser Lys Gly Lys Lys Tyr Ser
        60                  65                  70

Ala Leu Ile Glu Glu Ile Gln Gln Asn Ala Thr Thr Phe Asp Gly Lys
    75                  80                  85

Tyr Ala Phe Leu Lys Thr Tyr Asn Tyr Ser Leu Gly Ala Asp Asp Leu
90                  95                  100                 105

Thr Pro Phe Gly Glu Gln Glu Leu Val Asn Ser Gly Ile Lys Phe Tyr
                110                 115                 120

Gln Arg Tyr Glu Ser Leu Thr Arg Asn Ile Val Pro Phe Ile Arg Ser
            125                 130                 135

Ser Gly Ser Ser Arg Val Ile Ala Ser Gly Lys Lys Phe Ile Glu Gly
        140                 145                 150

Phe Gln Ser Thr Lys Leu Lys Asp Pro Arg Ala Gln Pro Gly Gln Ser
    155                 160                 165

Ser Pro Lys Ile Asp Val Val Ile Ser Glu Ala Ser Ser Ser Asn Asn
170                 175                 180                 185

Thr Leu Asp Pro Gly Thr Cys Thr Val Phe Glu Asp Ser Glu Leu Ala
                190                 195                 200

Asp Thr Val Glu Ala Asn Phe Thr Ala Thr Phe Val Pro Ser Ile Arg
            205                 210                 215

Gln Arg Leu Glu Asn Asp Leu Ser Gly Val Thr Leu Thr Asp Thr Glu
        220                 225                 230

Val Thr Tyr Leu Met Asp Met Cys Ser Phe Asp Thr Ile Ser Thr Ser
        235                 240                 245

Thr Val Asp Thr Lys Leu Ser Pro Phe Cys Asp Leu Phe Thr His Asp
250                 255                 260                 265

Glu Trp Ile Asn Tyr Asp Tyr Leu Gln Ser Leu Lys Lys Tyr Tyr Gly
                270                 275                 280

His Gly Ala Gly Asn Pro Leu Gly Pro Thr Gln Gly Val Gly Tyr Ala
            285                 290                 295

Asn Glu Leu Ile Ala Arg Leu Thr His Ser Pro Val His Asp Asp Thr
        300                 305                 310

Ser Ser Asn His Thr Leu Asp Ser Ser Pro Ala Thr Phe Pro Leu Asn
    315                 320                 325

Ser Thr Leu Tyr Ala Asp Phe Ser His Asp Asn Gly Ile Ile Ser Ile
330                 335                 340                 345

Leu Phe Ala Leu Gly Leu Tyr Asn Gly Thr Lys Pro Leu Ser Thr Thr
                350                 355                 360

Thr Val Glu Asn Ile Thr Gln Thr Asp Gly Phe Ser Ser Ala Trp Thr
            365                 370                 375

Val Pro Phe Ala Ser Arg Leu Tyr Val Glu Met Met Gln Cys Gln Ala
        380                 385                 390

Glu Gln Glu Pro Leu Val Arg Val Leu Val Asn Asp Arg Val Val Pro
    395                 400                 405

Leu His Gly Cys Pro Val Asp Ala Leu Gly Arg Cys Thr Arg Asp Ser
410                 415                 420                 425

Phe Val Arg Gly Leu Ser Phe Ala Arg Ser Gly Gly Asp Trp Ala Glu
                430                 435                 440

Cys Phe Ala
```

(2) INFORMATION FOR SEQ ID NO:33:

(i) SEQUENCE CHARACTERISTICS:

(A) LENGTH: 1404 base pairs
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
            (A) ORGANISM: Aspergillus ficuum (Aspergillus niger)
            (B) STRAIN: NRRL 3135

(xi) SEQUENCE DESCRIPTION: SEQ ID NO:33:

| | | | | | |
|---|---|---|---|---|---|
| ATGGGCGTCT | CTGCTGTTCT | ACTTCCTTTG | TATCTCCTGT | CTGGAGTCAC | CTCCGGACTG | 60 |
| GCAGTCCCCG | CCTCGAGAAA | TCAATCCAGT | TGCGATACGG | TCGATCAGGG | GTATCAATGC | 120 |
| TTCTCCGAGA | CTTCGCATCT | TTGGGGTCAA | TACGCACCGT | TCTTCTCTCT | GGCAAACGAA | 180 |
| TCGGTCATCT | CCCCTGAGGT | GCCCGCCGGA | TGCAGAGTCA | CTTTCGCTCA | GGTCCTCTCC | 240 |
| CGTCATGGAG | CGCGGTATCC | GACCGACTCC | AAGGGCAAGA | AATACTCCGC | TCTCATTGAG | 300 |
| GAGATCCAGC | AGAACGCGAC | CACCTTTGAC | GGAAAATATG | CCTTCCTGAA | GACATACAAC | 360 |
| TACAGCTTGG | GTGCAGATGA | CCTGACTCCC | TTCGGAGAAC | AGGAGCTAGT | CAACTCCGGC | 420 |
| ATCAAGTTCT | ACCAGCGGTA | CGAATCGCTC | ACAAGGAACA | TCGTTCCATT | CATCCGATCC | 480 |
| TCTGGCTCCA | GCCGCGTGAT | CGCCTCCGGC | AAGAAATTCA | TCGAGGGCTT | CCAGAGCACC | 540 |
| AAGCTGAAGG | ATCCTCGTGC | CCAGCCCGGC | CAATCGTCGC | CAAGATCGA | CGTGGTCATT | 600 |
| TCCGAGGCCA | GCTCATCCAA | CAACACTCTC | GACCCAGGCA | CCTGCACTGT | CTTCGAAGAC | 660 |
| AGCGAATTGG | CCGATACCGT | CGAAGCCAAT | TTCACCGCCA | CGTTCGTCCC | CTCCATTCGT | 720 |
| CAACGTCTGG | AGAACGACCT | GTCCGGTGTG | ACTCTCACAG | ACACAGAAGT | GACCTACCTC | 780 |
| ATGGACATGT | GCTCCTTCGA | CACCATCTCC | ACCAGCACCG | TCGACACCAA | GCTGTCCCCC | 840 |
| TTCTGTGACC | TGTTCACCCA | TGACGAATGG | ATCAACTACG | ACTACCTCCA | GTCCTTGAAA | 900 |
| AAGTATTACG | GCCATGGTGC | AGGTAACCCG | CTCGGCCCGA | CCCAGGGCGT | CGGCTACGCT | 960 |
| AACGAGCTCA | TCGCCCGTCT | GACCCACTCG | CCTGTCCACG | ATGACACCAG | TTCCAACCAC | 1020 |
| ACTTTGGACT | CGAGCCCGGC | TACCTTTCCG | CTCAACTCTA | CTCTCTACGC | GGACTTTTCG | 1080 |
| CATGACAACG | GCATCATCTC | CATTCTCTTT | GCTTTAGGTC | TGTACAACGG | CACTAAGCCG | 1140 |
| CTATCTACCA | CGACCGTGGA | GAATATCACC | CAGACAGATG | GATTCTCGTC | TGCTTGGACG | 1200 |
| GTTCCGTTTG | CTTCGCGTTT | GTACGTCGAG | ATGATGCAGT | GTCAGGCGGA | GCAGGAGCCG | 1260 |
| CTGGTCCGTG | TCTTGGTTAA | TGATCGCGTT | GTCCCGCTGC | ATGGGTGTCC | GGTTGATGCT | 1320 |
| TTGGGGAGAT | GTACCCGGGA | TAGCTTTGTG | AGGGGGTTGA | GCTTTGCTAG | ATCTGGGGGT | 1380 |
| GATTGGGCGG | AGTGTTTTGC | TTAG | | | | 1404 |

(2) INFORMATION FOR SEQ ID NO:34:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (synthetic)

(iii) HYPOTHETICAL: NO (xi) SEQUENCE DESCRIPTION: SEQ ID NO:34:

```
GGGTAGAATT CAAAAATGGG CGTCTCTGCT GTTCTA                                36

(2) INFORMATION FOR SEQ ID NO:35:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO:35:

AGTGACGAAT TCGTGCTGGT GGAGATGGTG TCG                                   33

(2) INFORMATION FOR SEQ ID NO:36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO:36:

GAGCACCAAG CTGAAGGATC C                                               21

(2) INFORMATION FOR SEQ ID NO:37:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO:37:

AAACTGCAGG CGTTGAGTGT GATTGTTTAA AGGG                                  34

(2) INFORMATION FOR SEQ ID NO:38:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (iii) HYPOTHETICAL: NO (vi) ORIGINAL SOURCE:
         AG-1

(xi) SEQUENCE DESCRIPTION: SEQ ID NO:38:

GACAATGGCT ACACCAGCAC CGCAACGGAC ATTGTTTGGC CC                         42

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
```

(D) TOPOLOGY: linear (ii) MOLECULE TYPE: DNA (synthetic)

(iii) HYPOTHETICAL: NO (vi) ORIGINAL SOURCE:
              AG-2

(xi) SEQUENCE DESCRIPTION: SEQ ID NO:39:

AAGCAGCCAT TGCCCGAAGC CGAT                                              24

(2) INFORMATION FOR SEQ ID NO:40:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (synthetic)

(iii) HYPOTHETICAL: NO (xi) SEQUENCE DESCRIPTION: SEQ ID NO:40:

CTCTGCAGGA ATTCAAGCTA G                                                 21

(2) INFORMATION FOR SEQ ID NO:41:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: DNA (synthetic)

(iii) HYPOTHETICAL: NO (vi) ORIGINAL SOURCE:
              18-2

(xi) SEQUENCE DESCRIPTION: SEQ ID NO:41:

CGAGGCGGGG ACTGCCAGTG CCAACCCTGT GCAGAC                                 36

(2) INFORMATION FOR SEQ ID NO:42:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: DNA (synthetic)

(iii) HYPOTHETICAL: NO (vi) ORIGINAL SOURCE:
              18-3

(xi) SEQUENCE DESCRIPTION: SEQ ID NO:42:

GTCTGCACAG GGTTGGCACT GGCAGTCCCC GCCTCG                                 36

(2) INFORMATION FOR SEQ ID NO:43:

(i) SEQUENCE CHARACTERISTICS:
          (A) LENGTH: 21 base pairs
          (B) TYPE: nucleic acid
          (C) STRANDEDNESS: single
          (D) TOPOLOGY: linear

```
    (ii) MOLECULE TYPE: DNA (synthetic)

(iii) HYPOTHETICAL: NO (xi) SEQUENCE DESCRIPTION: SEQ ID NO:43:

GGCACGAGGA TCCTTCAGCT T                                            21

(2) INFORMATION FOR SEQ ID NO:44:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (synthetic)

(iii) HYPOTHETICAL: NO (xi) SEQUENCE DESCRIPTION: SEQ ID NO:44:

AATTCAAGCT TG                                                      12

(2) INFORMATION FOR SEQ ID NO:45:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: DNA (synthetic)

(iii) HYPOTHETICAL: NO (vi) ORIGINAL SOURCE:
             24-2

(xi) SEQUENCE DESCRIPTION: SEQ ID NO:45:

CGAGCCGGGG ACTGCCAGGC GCTTGGAAAT CACATT                            36

(2) INFORMATION FOR SEQ ID NO:46:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: DNA (synthetic)

(iii) HYPOTHETICAL: NO (vi) ORIGINAL SOURCE:
             24-3

(xi) SEQUENCE DESCRIPTION: SEQ ID NO:46:

AATGTGATTT CCAAGCGCCT GGCAGTCCCC GCCTCG                            36

(2) INFORMATION FOR SEQ ID NO:47:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: DNA (synthetic)

(iii) HYPOTHETICAL: NO (vi) ORIGINAL SOURCE:
```

```
            fyt-2

(xi) SEQUENCE DESCRIPTION: SEQ ID NO:47:

AACAGCAGAG ACGCCCATTG CTGAGGTGTA ATGATG                         36

(2) INFORMATION FOR SEQ ID NO:48:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: DNA (synthetic)

(iii) HYPOTHETICAL: NO (vi) ORIGINAL SOURCE:
            fyt-3

(xi) SEQUENCE DESCRIPTION: SEQ ID NO:48:

CATCATTACA CCTCAGCAAT GGGCGTCTCT GCTGTT                         36

(2) INFORMATION FOR SEQ ID NO:49:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (ii) MOLECULE TYPE: DNA (synthetic)

(iii) HYPOTHETICAL: NO (xi) SEQUENCE DESCRIPTION: SEQ ID NO:49:

AGCTTCCCCG GTAC                                                 14

(2) INFORMATION FOR SEQ ID NO:50:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (ii) MOLECULE TYPE: DNA (synthetic)

(iii) HYPOTHETICAL: NO (xi) SEQUENCE DESCRIPTION: SEQ ID NO:50:

AGCTCCCCCG GATC                                                 14

(2) INFORMATION FOR SEQ ID NO:51:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (synthetic)

(iii) HYPOTHETICAL: NO (xi) SEQUENCE DESCRIPTION: SEQ ID NO:51:

AGCTAGGGGG                                                      10

(2) INFORMATION FOR SEQ ID NO:52:
```

```
    (i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (xi) SEQUENCE DESCRIPTION: SEQ ID NO:52:

TCGACCCCCT                                                              10
```

CLONING AND EXPRESSION OF PHYTASE FROM ASPERGILLUS

This application is a continuation of Ser. No. 08/417,448 filed Apr. 10, 1995, issued as U.S. Pat. No. 5,863,533 on Jan. 29, 1999, Ser. No. 08/151,574 filed Nov. 12, 1993, issued as U.S. Pat. No. 5,436,156 on Jul. 25, 1995, which is a continuation of Ser. No. 07/688,578 filed May 24, 1991, which is a U.S. national phase application of PCT/NL 90/00140 filed on Sep. 27, 1990.

The present invention relates to the microbial production of phytase.

BACKGROUND OF THE INVENTION

Phosphorus is an essential element for the growth of all organisms. In livestock production, feed must be supplemented with inorganic phosphorus in order to obtain a good growth performance of monogastric animals (e.g. pigs, poultry and fish).

In contrast, no inorganic phosphate needs to be added to the feedstuffs of ruminant animals. Microorganisms, present in the rumen, produce enzymes which catalyze the conversion of phytate (myo-inositolhexakis-phosphate) to inositol and inorganic phosphate.

Phytate occurs as a storage phosphorus source in virtually all feed substances originating from plants (for a review see: *Phytic acid, chemistry and applications,* E. Graf (ed.), Pilatus Press; Minneapolis, Minn., U.S.A. (1986)). Phytate comprises 1–3% of all nuts, cereals, legumes, oil seeds, spores and pollen. Complex salts of phytic acid are termed phytin. Phytic acid is considered to be an anti-nutritional factor since it chelates minerals such as calcium, zinc, magnesium, iron and may also react with proteins, thereby decreasing the bioavailability of protein and nutritionally important minerals.

Phytate phosphorus passes through the gastrointestinal tract of monogastric animals and is excreted in the manure. Though some hydrolysis of phytate does occur in the colon, the thus-released inorganic phosphorus has no nutritional value since inorganic phosphorus is absorbed only in the small intestine. As a consequence, a significant amount of the nutritionally important phosphorus is not used by monogastric animals, despite its presence in the feed.

The excretion of phytate phosphorus in manure has further consequences. Intensive livestock production has increased enormously during the past decades. Consequently, the amount of manure produced has increased correspondingly and has caused environmental problems in various parts of the world. This is due, in part, to the accumulation of phosphate from manure in surface waters which has caused eutrophication.

The enzymes produced by microorganisms, that catalyze the conversion of phytate to inositol and inorganic phosphorus are broadly known as phytases. Phytase producing microorganisms comprise bacteria such as *Bacillus subtilis* (V. K. Paver and V. J. Jagannathan (1982) J. Bacteriol. 151, 1102–1108) and Pseudonomas (D. J. Cosgrove (1970) Austral. J. Biol. Sci. 23, 1207–1220); yeasts such as *Saccharomyces cerevisiae* (N. R. Nayini and P. Markakis (1984) Lebensmittel Wissenschaft und Technologie 17, 24–26); and fungi such as *Aspergillus terreus* (K. Yamada, Y. Minoda and S. Yamamoto (1986) Agric. Biol. Chem. 32, 1275–1282). Various other Aspergillus species are known to produce phytase, of which, the phytase produced by *Aspergillus ficuum* has been determined to possess one of the highest levels of specific activity, as well as having better thermostability than phytases produced by other microorganisms (unpublished observations).

The concept of adding microbial phytase to the feedstuffs of monogastric animals has been previously described (Ware, J. H., Bluff, L. and Shieh, T. R. (1967) U.S. Pat. No. 3,297,548; Nelson, T. S., Shieh, T. R., Wodzinski, R. J. and Ware, J. H. (1971) J. Nutrition 101, 1289–1294). To date, however, application of this concept has not been commercially feasible, due to the high cost of the production of the microbial enzymes (Y. W. Han (1989) Animal Feed Sci. & Technol. 24, 345–350). For economic reasons, inorganic phosphorus is still added to monogastric animal feedstuffs.

Microbial phytases have found other industrial uses as well. Exemplary of such utilities is an industrial process for the production of starch from cereals such as corn and wheat. Waste products comprising e.g. corn gluten feeds from such a wet milling process are sold as animal feed. During the steeping process phytase may be supplemented. Conditions (T~50° C. and pH=5.5) are ideal for fungal phytases (see e.g. European Patent Application 0 321 004 to Alko Ltd.). Advantageously, animal feeds derived from the waste products of this process will contain phosphate instead of phytate.

It has also been conceived that phytases may be used in soy processing (see Finase™ Enzymes By Alko, a product information brochure published by Alko Ltd., Rajamäki, Finland). Soybean meal contains high levels of the anti-nutritional factor phytate which renders this protein source unsuitable for application in baby food and feed for fish, calves and other non-ruminants. Enzymatic upgrading of this valuable protein source improves the nutritional and commercial value of this material.

Other researchers have become interested in better characterizing various phytases and improving procedures for the production and use of these phytases. Ullah has published a procedure for the purification of phytase from wild-type *Aspergillus ficuum*, as well as having determined several biochemical parameters of the product obtained by this purification procedure (Ullah, A. (1988a) Preparative Biochem. 18, 443–458). Pertinent data obtained by Ullah is presented in Table 1, below.

The amino acid sequence of the N-terminus of the *A. ficuum* phytase protein has twice been disclosed by Ullah: Ullah, A. (1987) Enzyme and Engineering conference IX, Oct. 4–8, 1987, Santa Barbara, Calif. (poster presentation); and Ullah, A. (1988b) Prep. Biochem. 18, 459–471. The amino acid sequence data obtained by Ullah is reproduced in FIG. 1A, sequence E, below.

Several interesting observations may be made from the disclosures of Ullah. First of all, the "purified" preparation described in Ullah (1988a and 1988b) consists of two protein bands on SDS-PAGE. We have found, however, that phytase purified from *A. ficuum* contains a contaminant and that one of the bands found on SDS-PAGE, identified by Ullah as a phytase, is originating from this contaminant.

This difference is also apparent from the amino acid sequencing data published by Ullah (1987, 1988b; compare FIG. 1A, sequences A and B with sequence C). We have determined, in fact, that one of the amino acid sequences of internal peptides of phytase described by Ullah (see FIG. 1B, sequence E) actually belongs to the contaminating 100 kDa protein (FIG. 1C) which is present in the preparation obtained via the procedure as described by Ullah, and seen as one of the two bands on SDS-PAGE (Ullah, 1988a and 1988b). Ullah does not recognize the presence of such a contaminating protein, and instead identifies it as another form of phytase. The presence of such contamination, in turn, increases the difficulty in selecting and isolating the actual nucleotide sequence encoding phytase activity. Furthermore, the presence of the contamination lowers the specific activity value of the protein tested.

Further regarding the sequence published by Ullah, it should be noted that the amino acid residue at position 12, has been disclosed by Ullah to be glycine. We have consistently found using protein and DNA sequencing techniques, that this residue is not a glycine but is in fact a cysteine (see FIGS. 6 and 8).

Finally, Ullah discloses that phytase is an 85 kDa protein, with a molecular weight after deglycosylation of 61.7 kDa (Ullah, 1988b). This number, which is much lower than the earlier reported 76 kDa protein (Ullah, A. and Gibson, D. (1988) Prep. Biochem. 17(1), 63–91) was based on the relative amount of carbohydrates released by hydrolysis, and the apparent molecular weight of the native protein on SDS-PAGE. We have found, however, that glycosylated phytase has a single apparent molecular weight of 85 kDa, while the deglycosylated protein has an apparent molecular weight in the range of 48–56.5 kDa, depending on the degree of deglycosylation.

Mullaney et al. (Filamentous Fungi Conference, April, 1987, Pacific Grove, Calif. (poster presentation) also disclose the characterization of phytase from A. ficuum. However, this report also contains mention of two protein bands on SDS-PAGE, one of 85 kDa, and one of 100 kDa, which were present in the "purified" protein preparation. These protein bands are both identified by the authors as being forms of phytase. A method for transforming microbial hosts is proposed, but has not been reported. The cloning and isolation of the DNA sequence encoding phytase has not been described.

It will be appreciated that an economical procedure for the production of phytase will be of significant benefit to, inter alia, the animal feed industry. One method of producing a more economical phytase would be to use recombinant DNA techniques to raise expression levels of the enzyme in various microorganisms known to produce high levels of expressed peptides or proteins. To date, however, the isolation and cloning of the DNA sequence encoding phytase activity has not been published.

SUMMARY OF THE INVENTION

The present invention provides a purified and isolated DNA sequence coding for phytase. The isolation and cloning of this phytase encoding DNA sequence has been achieved via the use of specific oligonucleotide probes which were developed especially for the present invention. Preferred DNA sequences encoding phytases are obtainable from fungal sources, especially filamentous fungi of the genus Aspergillus.

It is another object of the present invention to provide a vector containing an expression construct which further contains at least one copy of at least one, preferably homologous DNA sequence encoding phytase, operably linked to an appropriate regulatory region capable of directing the high level expression of peptides or proteins having phytase activity in a suitable expression host.

The expression construct provided by the present invention may be inserted into a vector, preferably a plasmid, which is capable of transforming a microbial host cell and integrating into the genome.

It is a further object of the present invention to provide a transformant, preferably, a microbial host which has been transformed by a vector as described in the preceding paragraph. The transformed hosts provided by the present invention are filamentous fungi of the genera Aspergillus, Trichoderma, Mucor and Penicillium, yeasts of the genera Kluyveromyces and Saccharomyces or bacteria of the genus Bacillus. Especially preferred expression hosts are filamentous fungi of the genus Aspergillus. The transformed hosts are capable of producing high levels of recombinant phytase on an economical, industrial scale.

In other aspects, the invention is directed to recombinant peptides and proteins having phytase activity in glycosylated or unglycosylated form; to a method for the production of said unglycosylated peptides and proteins; to peptides and proteins having phytase activity which are free of impurities; and to monoclonal antibodies reactive with these recombinant or purified proteins.

A comparison of the biochemical parameters of the purified wild-type A. ficuum phytase as obtained by Ullah, against the further purified wild-type A. ficuum phytase, obtained via the present invention, is found in Table 1, below. Of particular note is the specific activity data wherein it is shown that the purified protein which we have obtained has twice the specific activity of that which was published by Ullah.

The present invention further provides nucleotide sequences encoding proteins exhibiting phytase activity, as well as amino acid sequences of these proteins. The sequences provided may be used to design oliconucleotide probes which may in turn be used in hybridization screening studies for the identification of phytase genes from other species, especially microbial species, which may be subsequently isolated and cloned.

The sequences provided by the present invention may also be used as starting materials for the construction of "second generation" phytases. "Second generation" phytases are phytases, altered by mutagenesis techniques (e.g. site-directed mutagenesis), which have properties that differ from those of wild-type phytases or recombinant phytases such as those produced by the present invention. For example, the temperature or pH optimum, specific activity or substrate affinity may be altered so as to be better suited for application in a defined process.

Within the context of the present invention, the term phytase embraces a family of enzymes which catalyze reactions involving the removal of inorganic phosphorous from various myoinositol phosphates.

Phytase activity may be measured via a number of assays, the choice of which is not critical to the present invention. For purposes of illustration, phytase activity may be determined by measuring the amount of enzyme which liberates inorganic phosphorous from 1.5 mM sodium phytate at the rate of 1 $\mu$mol/min at 37° C. and at pH 5.50.

It should be noted that the term "phytase" as recited throughout the text of this specification is intended to encompass all peptides and proteins having phytase activity. This point is illustrated in FIG. 1A which compares sequences A and B (sequences which have been obtained during the course of the present work) with sequence C (published by Ullah, 1988b). The Figure demonstrates that proteins may be obtained via the present invention which lack the first four amino acids (the protein of sequence A lacks the first seven amino acids) of the mature A. ficuum phytase protein. These proteins, however, retain phytase activity. The complete amino acid sequence of the phytase protein, as deduced from the corresponding nucleotide sequence, is shown in FIG. 8.

Phytases produced via the present invention may be applied to a variety of processes which require the conversion of phytate to inositol and inorganic phosphate.

For example, the production of phytases according to the present invention will reduce production costs of microbial phytases in order to allow its economical application in animal feed which eventually will lead to an in vivo price/performance ratio competitive with inorganic phosphate. As a further benefit, the phosphorus content of manure will be considerably decreased.

It will be appreciated that the application of phytases, available at a price competitive with inorganic phosphate, will increase the degrees of freedom for the compound seed industry to produce a high quality feed. For example, when feed is supplemented with phytase, the addition of inorganic phosphate may be omitted and the contents of various materials containing phytate may be increased.

In addition to use in animal feeds and soy processing as discussed above, the phytase obtained via the present invention may also be used in diverse industrial applications such as:

liquid feed for pigs and poultry. It has become common practice to soak feed for several hours prior to feeding. During this period the enzyme will be able to convert phytate to inositol and inorganic phosphate;

an industrial process for the production of inositol or inositol-phosphates from phytate;

other industrial processes using substrates that contain phytate such as the starch industry and in fermentation industries, such as the brewing industry. Chelation of metal ions by phytate may cause these minerals to be unavailable for the production microorganisms. Enzymatic hydrolysis of phytate prevents these problems.

These and other objects and advantages of the present invention will become apparent from the following detailed description.

BRIEF DESCRIPTION OF THE FIGURES

FIG. 1.
A. (SEQ ID NO:1), (SEQ ID NO:2), (SEQ ID NO:6) N-terminal amino acids as determined for purified phytase. The amino acid sequences labeled A and B are provided by the present invention, and originate, from the phytase subforms with isoelectric points of 5.2 and 5.4, respectively. Sequence C is cited from Ullah (1987, 1988b, supra). The amino acid residue located at position 12 of sequences A and B has been determined by the present invention not to be a glycine residue. [* denotes no unambigous identification. ** denotes no residue detected.]
B. (SEQ ID NO:4), (SEQ ID NO:5), (SEQ ID NO:7), (SEQ ID NO:8), (SEQ ID NO:9) N-terminal amino acid sequences of CNBr-cleaved internal phytase fragments. The amino acid sequences labeled A and B (apparent molecular weight approximately 2.5 kDa and 36 kDa peptides, respectively) are provided by the present invention. Sequences C through E are cited from Ullah (1988b, supra).
C. (SEQ ID NO:3) N-terminal amino acid sequence of a 100 kDa protein which has been found by the present invention to be present in crude phytase samples.

FIG. 2.
A. (SEQ ID NO:10), (SEQ ID NO:14), (SEQ ID NO:15), (SEQ ID NO:16), (SEQ ID NO:17), (SEQ ID NO:18), (SEQ ID NO:19), (SEQ ID NO:20), (SEQ ID NO:21), (SEQ ID NO:22), (SEQ ID NO:23), and (SEQ ID NO:24) Oligonucleotide probes designed on basis of the the data from FIG. 1A, peptides A through B.
B. (SEQ ID NO: 13), (SEQ ID NO:28), (SEQ ID NO:29) and (SEQ ID NO:30) Oligonucleotide probes designed on the basis of the data from FIG. 1B, peptides A and B.

FIG. 3. Oligonucleotide probes used for the isolation of the gene encoding the acid-phosphatase.

FIG. 6. (SEQ ID NO:31) and (SEQ ID NO:32) Compilation of the nucleotide sequences of plasmids pAF 2-3, pAF 2-6, and pAF 2-7 encompassing the chromosomal phytase gene locus. The phytase coding region is located from nucleotide position 210 to position 1713, an intron is present in the chromosomal gene from nucleotide position 254 to position 355. Relevant features such as restriction sites, the phytase start and stop codons, and the intron position are indicated.

FIG. 8. (SEQ ID NO:33) Nucleotide sequence of the translated region of the phytase cDNA fragment and the derived amino acid sequence of the phytase protein; the start of the mature phytase protein is indicated as position +1. The amino-terminus of the 36 kDa internal protein fragment is located at amino acid position 241, whereas the 2.5 kDa protein fragment starts at amino acid position 390.

DETAILED DESCRIPTION OF THE INVENTION

Figure 4:
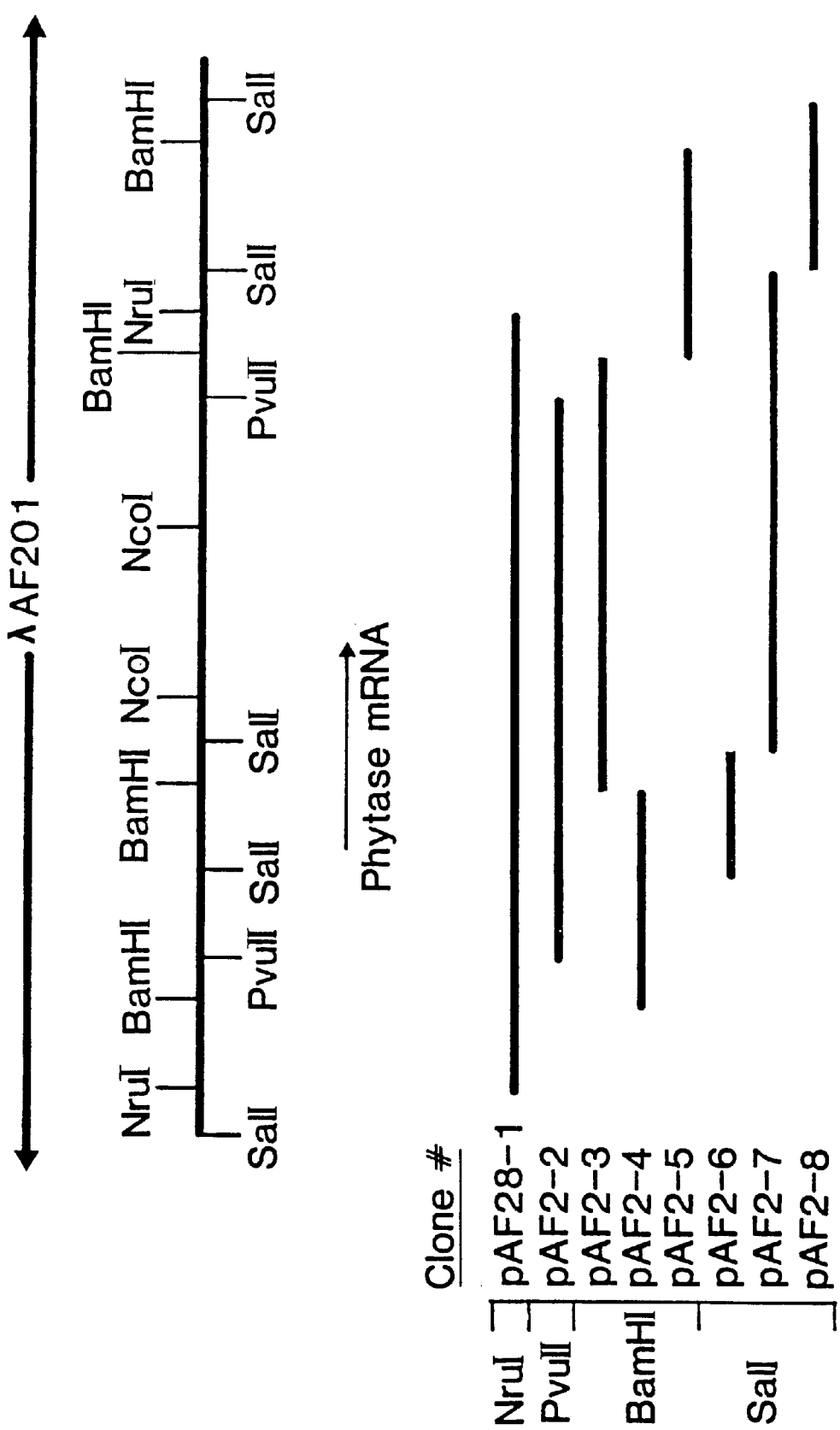
FIG. 4. Restriction map of bacteriophage lambda AF201 containing the phytase locus of A. ficuum. The arrow indicates the position of the phytase gene and the direction of transcription. Clone # shows the subclones derived with indicated restriction enzymes from phage AF201 in pAN 8-1 (for pAF 28-1) and in pUC19 (for all other subclones).

The cloning of the genes encoding selected proteins produced by a microorganism can be achieved in various ways. One method is by purification of the protein of interest, subsequent determination of its N-terminal amino acid sequence and screening of a genomic library of said micro-organism using a DNA oligonucleotide probe based on said N-terminal amino acid sequence. Examples of the successful application of this procedure are the cloning of the Isopenicillin N-synthetase gene from *Cephalosporium acremonium* (S. M. Samson et al. (1985) Nature 318, 191–194) and the isolation of the gene encoding the TAKA amylase for *Aspergillus oryzae* (Boel et al. (1986) EP-A-0238023).

Using this procedure, an attempt has been made to isolate the *Aspergillus ficuum* gene encoding phytase. The protein has been purified extensively, and several biochemical parameters have been determined. The data obtained have been compared to the data published by Ullah (1988a). Both sets of data are given in Table 1, below.

TABLE 1

Biochemical parameters of purified wild-type *A. ficuum* phytase

| Parameter | Present invention | Ullah |
| --- | --- | --- |
| Specific activity* | 100 U/mg protein | 50 U/mg protein |
| Purity: | | |
| SDS-PAGE | 85 kDa | 85/100 kDa |
| IEF-PAGE | 3 or 4 bands | not done |
| Km (Affinity constant) | 250 μM | 40 μM |
| Specificity for: | | |
| Inositol-1-P | not active | not active |
| Inositol-2-P | Km = 3.3 mM | 5% activity |
| pH optimum | 2.5 and 5.5 | 2.5 and 5.5 |
| Temp. optimum (° C.) | 50 | 58 |
| MW (kDa)** | 85 | 85 and 100 |
| MW (unglycosylated)** | 56.5 | 61.7 |
| Isoelectric Point*** | 5.0–5.4 | 4.5 |

TABLE 1-continued

Biochemical parameters of purified wild-type *A. ficuum* phytase

| Parameter | Present invention | Ullah |
| --- | --- | --- |

*Phytase activity is measured by Ullah at 58° C. rather than at 37° C. A unit of phytase activity is defined as that amount of enzyme which liberates inorganic phosphorus from 1.5 mM sodium phytate at the rate of 1 μmol/min at 37° C. and at pH 5.50. To compare the fermentation yields and the specific activities, the activities disclosed by Ullah were corrected for the temperature difference. The correction is based on the difference in phytase activity measured at 37° C. and at 58° C. as shown in Table III of Ullah (1988b).
**Apparent Molecular Weight as determined by SDS-PAGE.
***As determined by IEF-PAGE In order to isolate the gene encoding phytase, a first set of oligonucleotide probes was designed according to the above-described method (FIG. 2A). The design of these probes was based on the amino acid sequence data. As a control for the entire procedure, similar steps were taken to isolate the gene encoding acid-phosphatase, thereby using the protein data published by Ullah and Cummins ((1987) Prep. Biochem. 17, 397–422). For acid-phosphatase, the corresponding gene has been isolated without difficulties. However, for phytase, the situation appeared to be different. Despite many attempts in which probes derived from the N-terminal amino acid sequence were used, no genomic DNA fragments or clones from the genomic library could be isolated which could be positively identified to encompass the gene encoding phytase.

To overcome this problem, the purified phytase was subjected to CNBr-directed cleavage and the resulting protein fragments were isolated. The N-terminal amino acid sequences of these fragments were determined (FIG. 1B), and new oligonucleotide probes were designed, based on the new data (FIG. 2B). Surprisingly, the new oligonucleotide probes did identify specific DNA fragments and were suited to unambiguously identify clones from a genomic library. No cross hybridization was observed between the new clones or DNA fragments isolated therefrom, and the first set of oligonucleotide probes or the clones isolated using the first set of probes.

It will be appreciated that this second set of probes may also be used to identify the coding sequences of related phytases.

The newly isolated clones were used as probes in Northern blot hybridizations. A discrete mRNA could only be detected when the mRNA was isolated from phytase producing mycelium. When RNA from non-phytase producing mycelium was attempted, no hybridization signal was found. The mRNA has a size of about 1800 b, theoretically yielding a protein having a maximal molecular weight of about 60 kDa. This value corresponds to the molecular weight which has been determined for the non-glycosylated protein, and the molecular weight of the protein as deduced from the DNA sequence.

Moreover, when introduced into a fungal cell by transformation, an increase in phytase activity could be demonstrated. This indicates conclusively that the nucleotide sequence encoding phytase has indeed been isolated. The amino acid sequences which have been determined for the purified phytase enzyme, and for the CNBr fragments obtained therefrom, concur with the amino acid sequence deduced from the sequence which was determined for the cloned gene. The nucleotide sequence and the deduced amino acid sequence are given in FIGS. 6 and 8, and further illustrate the cloned sequence encoding phytase.

The isolation of the nucleotide sequence encoding phytase enables the economical production of phytase on an industrial scale, via the application of modern recombinant DNA techniques such as gene amplification, the exchange of regulatory elements such as e.g. promoters, secretional signals, or combinations thereof.

Accordingly, the present invention also comprises a transformed expression host capable of the efficient expression of high levels of peptides or proteins having phytase activity and, if desired, the efficient expression of acid phosphatases as well. Expression hosts of interest are filamentous fungi selected from the genera Aspergillus, Trichoderma, Mucor and Penicillium, yeasts selected from the genera Kluyveromyces and Saccharomyces and bacteria of the genus Bacillus. Preferably, an expression host is selected which is capable of the efficient secretion of their endogenous proteins.

Of particular interest are industrial strains of Aspergillus, especially *niger, ficuum, awamori* or *oryzae*. Alternatively, *Trichoderma reesei, Mucor miehei, Kluyveromyces lactis, Saccharomyces cerevisiae, Bacillus subtilis* or *Bacillus licheniformis* may be used.

The expression construct will comprise the nucleotide sequences encoding the desired enzyme product to be expressed, usually having a signal sequence which is functional in the host and provides for secretion of the product peptide or protein.

Various signal sequences may be used according to the present invention. A signal sequence which is homologous to the cloned nucleotide sequence to be expressed may be used. Alternatively, a signal sequence which is homologous or substantially homologous with the signal sequence of a gene at the target locus of the host may be used to facilitate homologous recombination. Furthermore, signal sequences which have been designed to provide for improved secretion from the selected expression host may also be used. For example, see Von Heyne (1983) Eur. J. Biochem. 133, 17–21; and Perlman and Halverson (1983) J. Mol. Biol. 167, 391–409. The DNA sequence encoding the signal sequence may be joined directly through the sequence encoding the processing signal (cleavage recognition site) to the sequence encoding the desired protein, or through a short bridge, usually fewer than ten codons.

Preferred secretional signal sequences to be used within the scope of the present invention are the signal sequence homologous to the cloned nucleotide sequence to be expressed, the 18 amino acid glucoamylase (AG) signal sequence and the 24 amino acid glucoamylase (AG) signal sequence, the latter two being either homologous or heterologous to the nucleotide sequence to be expressed.

The expression product, or nucleotide sequence of interest may be DNA which is homologous or heterologous to the expression host.

"Homologous" DNA is herein defined as DNA originating from the same genus. For example, Aspergillus is transformed with DNA from Aspergillus. In this way it is possible to improve already existing properties of the fungal genus without introducing new properties, which were not present in the genus before.

"Heterologous" DNA is defined as DNA originating from more than one genus, i.e., as follows from the example given in the preceding paragraph, DNA originating from a genus other than Aspergillus, which is then expressed in Aspergillus.

Nucleotide sequences encoding phytase activity are preferably obtained from a fungal source. More preferred are phytase encoding nucleotide sequences obtained from the genus Aspergillus. Most preferred sequences are obtained from the species *Aspergillus ficuum* or *Aspergillus niger*.

The region 5' to the open reading frame in the nucleotide sequence of interest will comprise the transcriptional initiation regulatory region (or promoter). Any region functional in the host may be employed, including the promoter which is homologous to the phytase-encoding nucleotide sequence to be expressed. However, for the most part, the region which is employed will be homologous with the region of the target locus. This has the effect of substituting the expression product of the target locus with the expression product of interest. To the extent that the level of expression and secretion of the target locus encoded protein provides for efficient production, this transcription initiation regulatory region will normally be found to be satisfactory. However, in some instances, one may wish a higher level of transcription than the target locus gene or one may wish to have inducible expression employing a particular inducing agent. In those instances, a transcriptional initiation regulatory region will be employed which is different from the region in the target locus gene. A large number of transcriptional initiation regulatory regions are known which are functional in filamentous fungi. These regions include those from genes encoding glucoamylase (AG), fungal amylase, acid phosphatase, GAPDH, TrpC, AmdS, AlcA, AldA, histone H2A, Pyr4, PyrG, isopenicillin N synthetase, PGK, acid protease, acyl transferase, and the like.

The target locus will preferably encode a highly expressed protein gene, i.e., a gene whose expression product is expressed to a concentration of at least about 0.1 g/l at the end of the fermentation process. The duration of this process may vary inter alia on the protein product desired. As an example of such a gene, the gene encoding glucoamylase (AG) is illustrative. Other genes of interest include fungal α-amylase, acid phosphatase, protease, acid protease, lipase, phytase and cellobiohydrolase. Especially preferred target loci are the glucoamylase gene of *A. niger*, the fungal amylase gene of *A. oryzae*, the cellobiohydrolase genes of *T. reesei*, the acid protease gene of *Mucor miehei*, the lactase gene of *Kluyveromyces lactis* or the invertase gene of *Saccharomyces cerevisiae*.

The transcriptional termination regulatory region may be from the gene of interest, the target locus, or any other convenient sequence. Where the construct includes further sequences of interest downstream (in the direction of transcription) from the gene of interest, the transcriptional termination regulatory region, if homologous with the target locus, should be substantially smaller than the homologous flanking region.

A selection marker is usually employed, which may be part of the expression construct or separate from the expression construct, so that it may integrate at a site different from the gene of interest. Since the recombinant molecules of the invention are preferably transformed to a host strain that can be used for industrial production, selection markers to monitor the transformation are preferably dominant selection markers, i.e., no mutations have to be introduced into the host strain to be able to use these selection markers. Examples of these are markers that enable transformants to grow on defined nutrient sources (e.g. the *A. nidulans* amdS gene enables *A. niger* transformants to grow on acetamide as the sole nitrogen source) or markers that confer resistance to antibiotics (e.g., the ble gene confers resistance to phleomycin or the hph gene confers resistance to hygromycin B).

The selection gene will have its own transcriptional and translational initiation and termination regulatory regions to allow for independent expression of the marker. A large number of transcriptional initiation regulatory regions are known as described previously and may be used in conjunction with the marker gene. Where antibiotic resistance is employed, the concentration of the antibiotic for selection will vary depending upon the antibiotic, generally ranging from about 30 to 300 µg/ml of the antibiotic.

The various sequences may be joined in accordance with known techniques, such as restriction, joining complementary restriction sites and ligating, blunt ending by filling in overhangs and blunt ligation, Bal31 resection, primer repair, in vitro mutagenesis, or the like. Polylinkers and adapters may be employed, when appropriate, and introduced or removed by known techniques to allow for ease of assembly of the expression construct. At each stage of the synthesis of the construct, the fragment may be cloned, analyzed by restriction enzyme, sequencing or hybridization, or the like. A large number of vectors are available for cloning and the particular choice is not critical to this invention. Normally, cloning will occur in $E.$ $coli$.

The flanking regions may include at least part of the open reading frame of the target locus, particularly the signal sequence, the regulatory regions 5' and 3' of the gene of the target locus, or may extend beyond the regulatory regions. Normally, a flanking region will be at least 100 bp, usually at least 200 bp, and may be 500 bp or more. The flanking regions are selected, so as to disrupt the target gene and prevent its expression. This can be achieved by inserting the expression cassette (comprising the nucleotide sequence to be expressed and optionally including additional elements such as a signal sequence, a transcriptional initiation regulatory region sequence and/or a transcriptional termination regulatory region sequence) into the open reading frame proximal to the 5' region, by substituting all or a portion of the target gene with the expression construct, or by having the expression construct intervene between the transcriptional initiation regulatory region at the target locus and the open reading frame. As already indicated, where the termination regulatory region is homologous with the region at the target locus, the 3'-flanking region should be substantially larger than a termination regulatory region present in the construct.

The present invention also provides the starting material for the construction of 'second-generation' phytases, i.e. phytase enzymes with properties that differ from those of the enzyme isolated herein. Second-generation phytases may have a changed temperature or pH optimum, a changed specific activity or affinity for its substrates, or any other changed quality that makes the enzyme more suited for application in a defined process. $E.$ $coli$ is the best host for such mutagenesis (e.g. site-directed mutagenesis). Since $E.$ $coli$ lacks the splicing machinery for the removal of introns which might be present in the phytase gene, a cDNA clone of phytase is the sequence of choice to be expressed in $E.$ $coli$. This cDNA sequence can be readily mutated by procedures well known in the art, after which the mutated gene may be introduced into the desired expression constructs.

The construct may be transformed into the host as the cloning vector, dither linear or circular, or may be removed from the cloning vector as desired. The cloning vector is preferably a plasmid. The plasmid will usually be linearized within about 1 kbp of the gene of interest. Preferably, the expression construct for the production of the phytases of the present invention will be integrated into the genome of the selected expression host.

A variety of techniques exist for transformation of filamentous fungi. These techniques include protoplast fusion or transformation, electroporation and micro-projectile firing into cells. Protoplast transformation has been found to be successful and may be used with advantage.

Mycelium of the fungal strain of interest is first converted to protoplasts by enzymatic digestion of the cell wall in the presence of an osmotic stabilizer such as KCl or sorbitol. DNA uptake by the protoplasts is aided by the addition of $CaCl_2$ and a concentrated solution of poly-ethylene glycol, the latter substance causing aggregation of the protoplasts, by which process the transforming DNA is included in the aggregates and taken up by the protoplasts. Protoplasts are subsequently allowed to regenerate on solid medium, containing an osmotic stabilizer and, when appropriate, a selective agent, for which the resistance is encoded by the transforming DNA.

After selecting for transformants, the presence of the gene of interest may be determined in a variety of ways. By employing antibodies, where the expression product is heterologous to the host, one can detect the presence of expression of the gene of interest. Alternatively, one may use Southern or Northern blots to detect the presence of the integrated gene or its transcription product.

Amplification of the nucleotide sequence or expression construct of interest may be achieved via standard techniques such as, the introduction of multiple copies of the construct in the transforming vector or the use of the amdS gene as a selective marker (e.g. Weinans et al. (1985) Current Genetics, 9, 361–368). The DNA sequence to be amplified may comprise DNA which is either homologous or heterologous to the expression host, as discussed above.

The cells may then be grown in a convenient nutrient medium. Low concentrations of a protease inhibitor may be employed, such as phenylmethylsulfonyl fluoride, α2-macro-globulins, pepstatin, or the like, Usually, the concentration will be in the range of about 1 µg/ml to 1 mg/ml. The protease gene(s) may be inactivated in order to avoid or reduce degradation of the desired protein.

The transformants may be grown in either batch or continuous fermentation reactors, where the nutrient medium is isolated and the desired product extracted.

Various methods for purifying the product, if necessary, may be employed, such as chromatography (e.g., HPLC), solvent-solvent extraction, electrophoresis, combinations thereof, or the like.

The present invention also provides a downstream processing method in which the fermentation broth (optionally purified) is filtered, followed by a second germ-free filtration, after which the filtered solution is concentrated. The thus-obtained liquid concentrate may be used as follows:

a) Phytase and other proteins may be precipitated from the liquid concentrate by adding acetone to a final volume of 60% (v/v) under continuous stirring. The precipitate may be dried in a vacuum at 35° C. After grinding the dry powder, the enzyme product may be used as such for application experiments. Recovery yields are about 90%.

b) The liquid concentrate may be spray-dried using conventional spray-drying techniques. Recovery yields vary from 80 to 99%.

c) The liquid concentrate may be mixed with carrier materials such as wheat bran. The thus-obtained mixture may be dried in a spray tower or in a fluid bed.

d) The liquid concentrate may be osmotically stabilized by the addition of e.g. sorbitol. A preservative such as benzoic acid may be added to prevent microbial contamination.

All four formulations may be sold to premix manufacturers, compound feed industries, other distributors and farmers.

The examples herein are given by way of illustration and are in no way intended to limit the scope of the present invention. It will be obvious to those skilled in the art that the phytase gene of the invention can be used in heterologous hybridization experiment, directed to the isolation of phytase encoding genes from other micro-organisms.

EXAMPLE 1

Fermentation of *A. ficuum* NRRL 3135

*Aspergillus ficuum* strain NRRL 3135 was obtained from the Northern Region Research Lab, USDA, 1815 North University Street, Peoria., Ill., USA. Fungal spore preparations were made following standard techniques.

Spores and subsequently cells were transferred through a series of batch fermentations in Erlenmeyer flasks to a 10 l fermentor. After growth in batch culture, the contents of this fermentor were used as inoculum for a final 500 liter batch fermentation.

The media used contains: 91 g/l corn starch (BDH Chemicals Ltd.); 38 g/l glucose.$H_2O$; 0.6 g/l $MgSO_4.7H_2O$; 0.6 g/l KCl; 0.2 g/l $FeSO_4.7H_2O$ and 12 g/l $KNO_3$. The pH was maintained at 4.6±0.3 by automatic titration with either 4N NaOH or 4N $H_2SO_4$.

Cells were grown at 28° C. at an automatically controlled dissolved oxygen concentration of 25% air saturation. Phytase production reached a maximum level of 5–10 U/ml after 10 days of fermentation.

EXAMPLE 2

Purification and Characterization of *A. ficuum* Phytase

A. Phytase Activity Assay

100 μl of broth filtrate (diluted when necessary) or supernatant or 100 μl of demiwater as reference are added to an incubation mixture having the following composition:

0.25 M sodium acetate buffer pH 5.5, or glycine HCL-buffer pH 2.5

1 mM phytic acid, sodium salt demiwater up to 900 μl

The resulting mixture is incubated for 30 minutes at 37° C. The reaction is stopped by the addition of 1 ml of 10% TCA (trichloroacetic acid). After the reaction has terminated, 2 ml of reagent (3.66 g of $FeSO_4.7H_2O$ in 50 ml of ammonium molybdate solution (2.5 g $(NH_4)_6Mo_7O_{24}.4H_2O$ and 8 ml $H_2SO_4$, diluted up to 250 ml with demiwater)) is added.

The intensity of the blue color is measured spectrophotometrically at 750 nm. The measurements are indicative of the quantity of phosphate released in relation to a calibration curve of phosphate in the range of 0–1 mMol/l.

Phosphatase stain

Components with phospatase activity were detected by isoelectric focusing using a general phosphatase stain. The gel was incubated with a solution of α-naphthylphosphate and Fast Garnet GBC salt (Sigma, 0.1 & 0.2% (w/v), respectively) in 0.6 M sodium acetate buffer pH 5.5. The reaction, which results in the appearance of a black precipitate, was either terminated with methanol:acetic acid (30:10%, v/v), or, should the protein having phytase activity be further required, by rinsing with distilled water.

B. Purification of *A. ficuum* Phytase

Phytase was purified to homogeneity from the culture broth of *A. ficuum* NRRL 3135. The broth was first made germ-free by filtration. The resulting culture filtrate was subsequently further concentrated in a Filtron ultrafiltration unit with 30 kD cutoff filters. The pH and ionic strength of the sample were adjusted for the purification procedure by washing the sample with 10 mM sodium acetate buffer pH 4.5. The final concentration in this ultrafiltration procedure was approximately 20 fold.

The sample was then applied to a cation exchanger (S-Sepharose Fast-Flow in a HR 16/10 20 ml column, both obtained from Pharmacia) in a Waters Preparative 650 Advanced Protein Purification System. The proteins bound were eluted with a sodium chloride gradient from 0–1 M in the sodium acetate buffer. Phytase eluted at approximately 250 mM NaCl. Phytase activity containing fractions were pooled, concentrated and desalted by ultrafiltration. The resulting solution was applied to an anion exchanger (Q-Sepharose Fast-Flow in a HR 16/10 20 ml column, Pharmacia), and the proteins were again elute a by a sodium chloride gradient from 0–1 M in the acetate buffer described above. Phytase was eluted from this column at approximately 200 mM NaCl.

The result of these purification steps is a partially purified phytase preparation with a specific activity of approximately 40–50 U/mg protein, indicating a 25-fold purification.

Analysis of the purity of the partially purified phytase indicated the presence of a major impurity with a molecular weight of approximately 100 kDa (FIG. 1B, sequence E). Isoelectric focusing indicated the presence of a number of phosphatase activity containing enzymes, including 3–4 phytase subforms (iselectric points varying from 5.0–5.4) (FIG. 1A, sequences A and B).

In order to obtain a homogeneous phytase preparation, a further two-fold purification was achieved by a subsequent separation of the components of the partially purified phytase by isoelectric focusing in a LKB Multiphor system on Ampholine PAG plates (pH range 4–6.5). The proteins with phosphatase activity (including the phytase) were detected by the general phosphatase staining procedure described above. The bands of interest were subsequently excised from the gel and the active protein was eluted by a 16 hr incubation of the gel slices in 10 mM sodium acetate buffer 5.5. The protein fractions were analysed in the specific phytase activity assay, as described in Example 2, thus discriminating the phytase fractions from other acid phosphatases. The final purification factor for phytase was approximately 60 fold (specific activity of final preparation 100 U/mg protein). In this final purification step it wag also possible to isolate different subforms of phytase (FIG. 1A, sequences A and B).

Monoclonal antibodies directed against the *A. ficuum* phytase were prepared, providing an effective purification procedure. The antibody was, coupled to cyanogen bromide-activated Sepharose 4B (5 mg/ml gel), and this matrix was used in a immunoaffinity column. The matrix was shown to bind approximately 1 mg phytase per ml. The phytase could be eluted from the affinity column with a pH 2.5 buffer (100 mM glycine-HCl, 500 mM NaCl) without any loss of activity. This procedure can be used to isolate homogeneous phytase from a crude culture filtrate in one single step with an 80% recovery and a 60-fold purification.

C. Deglycosylation of Phytase

*A. ficuum* phytase (70 μg protein) was incubated with 2.5 U N-Glycanase (Genzyme) in 0.2 M sodium phosphate buffer pH 8.6 and 10 mM 1,10-phenanthroline in a total volume of 30 μl.

After 16 hrs at 37° C., the extent of deglycosylation was checked by electrophoresis (Phast System, Pharmacia). The apparent molecular weight of the phytase was found to decrease from 85 kDa to approximately 56.5 kDa. The periodic acid Schiff (PAS) sugar staining, which identifies native phytase as a glycoprotein, failed to detect any residual carbohydrates attached to the protein. The complete removal of carbohydrate was further substantiated by the sensitive lectin-blotting method. Native and deglycosylated phytase (both 1.5 µg) were run on a standard SDS-PAGE gel and electrophoretically transferred to a PVDF membrane (Immobilon, Millipore) in 25 mM TRIS-glycine buffer pH 8.3, 20% (v/v) methanol, for a period of 16 hrs at 30V.

The membrane was subsequently incubated with 1% (w/v) bovine serum albumin in phospate buffered saline and incubated with concanavalin A-peroxidase (Sigma, 10 µg/ml in phosphate buffered saline). The peroxidase was then stained with 4-chloro-1-naphthol (Sigma).

This sensitive method also failed to detect any residual carbohydrate attached to the deglycosylated phytase.

After deglycosylation, phytase has completely lost its activity, possibly due to aggregation of the enzyme.

EXAMPLE 3

Determination of the Amino Acid Sequence of Phytase and Design of Oligonucleotide Probes A. Determination of the N-terminal Amino Acid Sequence Phytase was electrophoretically transferred from SDS-PAGE or from IEF-PAGE onto a PVDF blotting membrane (Immobilon, Millipore). Electroblotting was performed in 10 mM CAPS (3-cyclohexylamino-propanesulfonic acid) buffer pH 11.0, with 10% (v/v) methanol, for a period of 16 hrs, at 30V and 4° C.

The protein was located with Coomassie Brilliant Blue staining. The band of interest was excised, further destained in methanol and subjected to gas-phase sequencing. The procedure has been carried out several times, using several individual preparations. The results obtained are given in FIG. 1A (sequences A and B).

The amino acid sequence has also been determined for a 100 kDa protein that was present in crude preparations. The data obtained far this protein are given in FIG. 1C. This sequence shows considerable homology with the acid phosphatase that has been isolated from *Aspergillus niger* (MacRae et al. (1988) Gene 71, 339–348).

B. Determination of Internal Amino Acid Sequences

Protein fragmentation by cyanogen bromide

Phytase, purified to homogeneity, was transferred into 100 mM NaHCO$_3$ by ultrafiltration (Microconcentrator Centriron 30, Amicon). The protein was subsequently lyophilized, dissolved in 70% trifluoroacetic acid (v/v), and incubated for 6 hr with an approximately 300-fold molar excess of CNBr. The reaction was terminated by dilution of the mixture with water. The resulting fragments were again lyophilized. The sample was then dissolved in SDS-PAGE sample buffer containing DTT (dithiothreitol), and the extent of fragmentation was determined by PAGE. Analytical PAGE was performed on a Pharmacia Phast-System unit, on 20% SDS-PAGE gels. The gels were prerun to create a continuous buffer system to improve the separation of the small peptides (according to the manual). Peptides were detected using a silver-staining technique known in the art, since Coomassie Brilliant Blue failed to detect the smallest peptide. The result of the procedure was a complete degradation of phytase into peptides with molecular weights of <2.5 kDa, 36 kDa, 57 kDa and 80 kDa.

The peptides were isolated for gas-phase sequencing by SDS-Tricine-PAGE as described by Schagger & Jagow (1987) Anal. Biochem. 166, 368–379 followed by electroblotting as described above.

The N-terminus of the 57 kDa fragment is identical to the N-terminus of phytase as determined by Ullah (1988b, supra), with the exception of the first four amino acids which are absent (FIG. 1A, sequence B). The N-terminal sequences of the 2.5 kDa and 36 kDa peptides are shown in FIG. 1B as sequences A and B.

C. Oligonucleotide Probes

Oligonucleotide probes have been designed, based on the amino acid sequences given in FIGS. 1A and 1B, and were prepared using an Applied Biosystems ABI 380B DNA synthesizer. These oligonucleotides are given in FIGS. 2A and 2B.

EXAMPLE 4

Hybridization of Genomic Blots and Genomic Libraries with a First Set of Oligonucleotide Probes Genomic DNA from *A. ficuum* has been isolated by grinding the mycelium in liquid nitrogen, using standard procedures (e.g. Yelton et al (1984) Proc. Natl. Acad. Sci.-U.S.A., 1470–1474). A genomic library was constructed in the bacteriophage vector lambda EMBL3, using a partial Sau3A digest of *A. ficuum* NRRL 3135 chromosomal DNA, according to standard techniques (e.g. Maniatis et al. (1982) *Molecular cloning, a laboratory manual,* Cold Spring Harbor Laboratory, New York). The thus-obtained genomic library contained 60 to 70 times the *A. ficuum* genome. The library was checked for the occurrence of plaques without insert by hybridization with the lambda EMBL3 stuffer fragment. Less than 1% of the plaques were observed to hybridize to the lambda EMBL3 probe. The insert size was 13 to 17 kb.

To identify conditions and probes that were suited for the screening of the genomic library, genomic DNA was digested with several restriction enzymes, separated on agarose gels and blotted onto Genescreen plus, using the manufacturers instructions. The blots were hybridized with all oligonucleotide probes. Hybridization was performed usings conditions of varying stringency (6×SSC, 40 to 60° C. for the hybridization; up to 0.2×SSC, 65° C. for the washing). Probes 1068 and 1024 (FIG. 2A) were selected for the screening of the genomic library, although no common DNA fragments could be identified that hybridized specifically with both probes. Acid-phosphatase probe 1025 (FIG. 3) gave a specific and discrete hybridization signal and hence this probe was selected for screening the genomic library for the acid phosphatase gene.

Using all three probes, hybridizing plaques could be identified in the genomic library. The hybridization signal corresponding to probe 1025 (acid phosphatase) was strong and reproducible. Hybridization signals of variable intensity were observed using probes 1024 and 1068 (phytase). No cross hybridization between the two series was observed. All three series of plaques were rescreened and DNA was isolated from eight single, positive hybridizing plaques (Maniatis et al., supra). In each series, clones that contained identical hybridizing fragments could be identified, indicating that the inserts of said clones are related and probably overlap the same genomic DNA region. Again, no cross-hybridization could be demonstrated using the two phytase specific series (probes 1024 and 1068), indicating that, although both probes used to isolate the two series of clones were obtained from the N-terminal amino acid sequence of the protein, different genomic DNA fragments had been identified and cloned.

Figure 5:
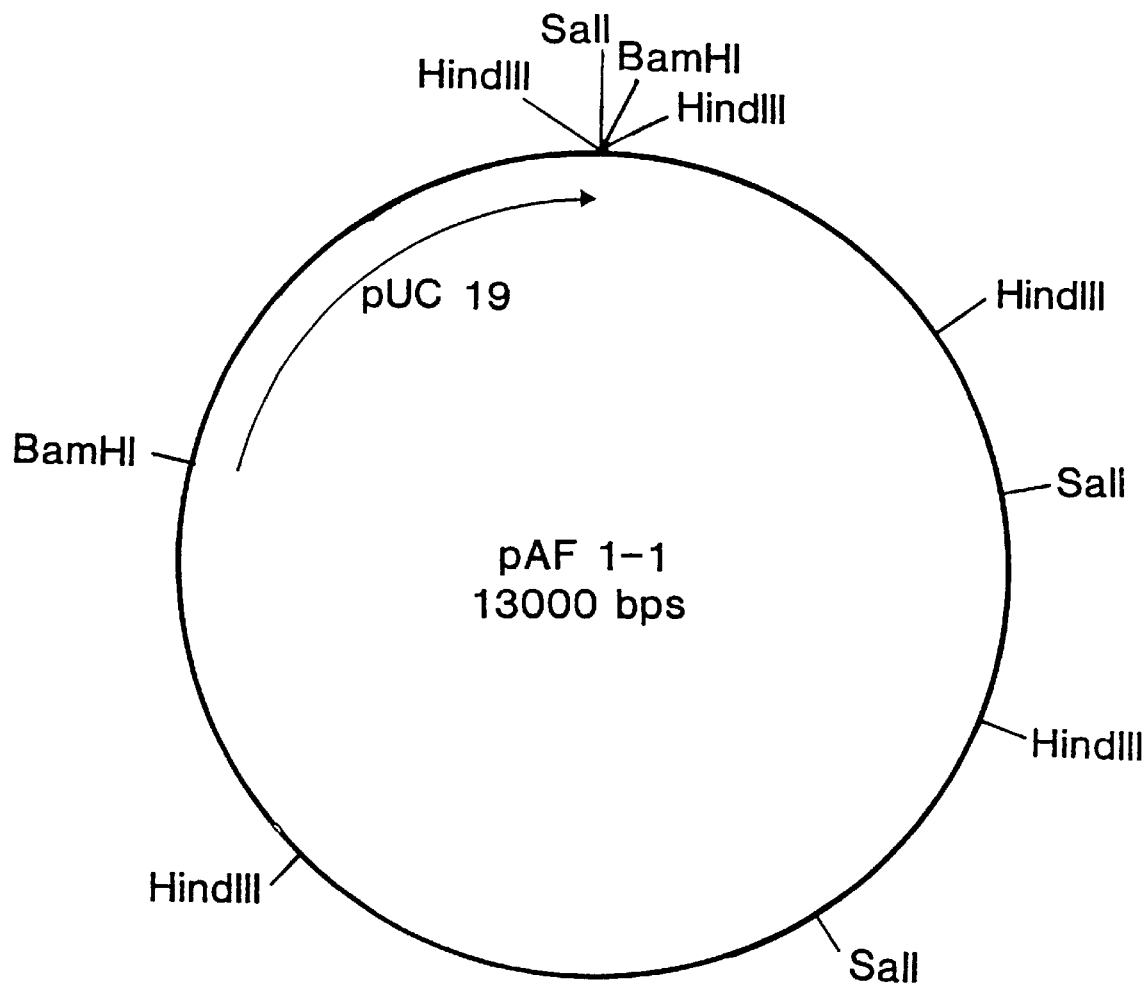
FIG. 5. Physical map of pAF 1-1. The 10 kb BamHI fragment, inserted in pUC19, contains the entire gene encoding acid phosphatase from A. ficuum.

All three series of clones were hybridized with Northern blots containing mRNA isolated from induced and non-induced mycelium (Example 6). The acid phosphatase-specific clones, as well as the isolated internal 3.1 kb SalI fragment from these clones, hybridized exclusively to induced mRNA samples. The mRNA identified by the acid phosphatase-specific probes is about 1800 b in length, which agrees with the known size of the protein (68 kDa, Ullah and Cummins (1987) Prep. Biochem. 17, 397–422). No hybridization of the phytase-specific clones with specific mRNA's could be demonstrated. We have thus concluded that the above-described method was unsuccessful in cloning the gene encoding phytase. It may be further concluded that this failure is not due to a failure in the method used, since the method has been successfully applied to identify the gene encoding acid phosphatase. The lambda clone containing the acid phosphatase gene was deposited on Apr. 24, 1989 at the Centraal Bureau voor Schimmelcultures, Baarn, The Netherlands and has been assigned accession number CBS 214.89. A 10 kb BamHI fragment has been isolated from phage Z1 and subcloned into pUC19. This subclone contains the entire gene encoding acid phosphatase. The subclone, pAF 1-1 (FIG. 5) was deposited on Apr. 24, 1989 as CBS 213.89.

EXAMPLE 5
Isolation of the Gene Encoding Phytase, using a Second Set of Oligonucleotide Probes Probes have been designed using the N-terminal amino acid sequence of CNBr-generated fragments (FIG. 2B, probes 1295, 1296 and 1297) and have been hybridized with genomic DNA as described above. The feasibility of using these probes in the isolation of the gene encoding phytase was again studied by Southern hybridization of genomic blots with the probes. This time, hybridizing fragments of corresponding lengths could be identified, using all three probes, despite the fact that the probes have been derived from non-overlapping regions. No hybridization was found between the new set of probes and the clones that have been isolated using the first set of probes (Example 4). Therefore, the genomic library was rescreened using all three probes in separate experiments. A subset of the clones (lambda AF201, 219, 241 and 243) isolated with each individual probe also hybridized with both other probes, indicating that in this case, using the three different probes, clones were isolated from a single genomic region. Attempts were made to hybridize the newly isolated clones with probes 1024 and 1068. In both cases, no hybridization with the newly isolated clones was observed under conditions in which both probes had successfully hybridized to the clones which were isolated using these probes (see Example 4). This demonstrates that the newly isolated clones have no homology to the probes derived from the N-terminus of the purified phytase.

A lambda EMBL3-clone, which hybridizes to all three probes (1295–1297), was named lambda AF201 (FIG. 4) and was deposited on Mar. 9, 1989 as CBS 155.89.

A 5.1 kb BamHI fragment of lambda AF201 (subcloned in pUC19 and designated pAF 2-3, see FIG. 4), hybridizing to all three oligonucleotide probes, was used to probe a Northern blot. In this case, a discrete mRNA having a size of 1800 bases was identified. This mRNA was found only in induced mycelium. Similar results were obtained when the oligonucleotides were used as probes. Therefore, using the new set of probes, a common DNA fragment has been identified, which hybridizes specifically to an induced mRNA. The length of this mRNA (1800 b) is sufficient to encode a protein of about 60 kDa, which is about the size of the non-glycosylated protein. Clearly, the isolated fragments contain at least part of the gene encoding phytase.

EXAMPLE 6
Isolation of "Induced" and "Non-induced" mRNA

It is known from the literature that the synthesis of phytase by *A. ficuum* is subject to a stringent phosphate-dependent regulation (Han and Callagher (1987) J. Indust. Microbiol. 1, 295–301). Therefore, the demonstration that an isolated gene is subject to a similar regulation can be considered to support the evidence that the gene of interest has been cloned.

In order to isolate mRNA that has been synthesized under both producing and non-producing conditions, *A. ficuum* NRRL 3135 was grown as follows. Spores were first grown overnight in non-inducing medium. The next day, the mycelium was harvested, washed with sterile water and inoculated into either inducing or non-inducing medium. The medium used contains (per liter): 20 g corn starch; 7.5 g glucose; 0.5 g $MgSO_4.7 H_2O$; 0.2 g $FeSO_4.7 H_2O$; and 7.2 g $KNO_3$. For the induction of phytase, up to 2 g/l corn steep liquor was added to the medium, while non-inducing medium contains 2 g/l $K_2HPO_4$. The mycelium was grown for at least a further 100 hours. Samples were taken at selected intervals. Phytase production was followed by the phytase assay as described in Example 2A. Denatured mRNA was separated by electrophoresis and blotted onto Genescreen plus. The blots were hybridized with $^{32}P$-labelled pAF 2-3 or with the isolated 3.1 kb SalI fragment from pAF 1-1 (acid phosphatase) from Example 4. The results are shown in Table 2.

Positive hybridization of the phytase specific 5.1 kb BamHI fragment and the acid phosphatase specific 3.1 kb SalI fragment with isolated mRNA is observed only when cells are grown under conditions which are known to induce the synthesis of phytase and acid phosphatases. From these results it has been concluded that the isolated genes are regulated as expected for phytase and acid phosphatases.

TABLE 2

|   | Time after inoculation | Induced | Non-induced |
|---|---|---|---|
| A | 24 hours | + | − |
| B | 24 hours | + | − |

Hybridization of Northern blots using the phytase-specific 5.1 kb BamHI fragment (A) or the acid phosphatase specific 3.1 kb SalI fragment (B) as a probe;
a + indicates the presence of the 1800 b phytase mRNA or the 1800 b acid phosphatase mRNA.
The relative phytase activity was determined for the 24 hr. samples: induced cultures have 10 times more phytase activity than non-induced cultures.

EXAMPLE 7
Evidence for the Cloning of the Phytase Gene

To obtain definitive proof for the successful isolation of the gene encoding phytase, and to study the feasibility of increasing the expression of the cloned gene, the phytase gene was subcloned into a suitable vector and transformed to *A. niger* 402 (ATCC 9092). To this end, the phytase gene was isolated from the lambda clone AF201 as a 10 kb NruI fragment and cloned into the StuI site of the vector pAN 8-1 (Mattern, I. E. and Punt, P. J. (1988) Fungal Genetics Newsletter 35, 25) which contains the ble gene (conferring resistance to phleomycin) as a selection marker. The resulting construct was named pAF 28-1 (FIG. 4) and was transformed to *A. niger* 402 according to the procedure as described in Example 9, with the exception that the protoplasts were plated on Aspergillus minimal medium supplemented with 30 μg phleomycin/ml and solidified with 0.75% agar. Single transformants were purified and isolated and were tested for production in shake flasks, as described in Examples 1 and 2. As controls, transformants possessing only the vector, as well as the untransformed host were also tested (Table 3). Only *A. niger* 402 containing pAF 28-1 appeared to produce a phytase that reacted with a specific monoclonal antibody directed against *A. ficuum* phytase. The phytase reacting with this monoclonal antibody could be eluted from an immuno affinity column at pH 2.5 and was shown to be identical in molecular weight, degree of glycosylation, isoelectric point and specific activity to the *A. ficuum* phytase. This finding provides clear evidence that *A. niger* 402 cells transformed with pAF 28-1 express a phytase that is virtually identical to the *A. ficuum* phytase. Similar expression was not observed in either type of control cells.

TABLE 3

| Strain | Phytase/Activity U/ml | % of phytase-activity adsorbed onto the immunoaffinity column |
| --- | --- | --- |
| A. niger 402 | 0.5 | 0 |
| A. niger 402 pAF 28-1 | 0.7 | 10 |
| A. niger 402 pAN 8-1 | 0.5 | 0 |

Strains were grown under induced conditions (Example 6). Samples were taken after 96 hours of growth.

EXAMPLE 8

Characterization of the Phytase Gene

The lambda clones containing the phytase gene have bean analyzed by digestion with various restriction enzymes. A map of the genomic region encompassing the phytase gene is given in FIG. 4. Defined restriction fragments have been subcloned in the cloning vector pUC19, as indicated in FIG. 4.

It has previously been shown (Example 5) that the 5.1 kb BamHI fragment present in pAF 2-3 encompasses at least part of the phytase gene. Moreover the oligonucleotide probes 1295 and 1297 (FIG. 2B) were shown to hybridize to the SalI insert from pAF 2-7 (positions of pAF 2 clones are presented in FIG. 4), while probe 1296 probably spans the SalI site between the fragments in pAF 2-6 and pAF 2-7. The results of these experiments indicate that the phytase encoding sequence is located in the lefthand part of the BamHI insert of -pAF 2-3.

Subsequently the nucleotide sequences of the inserts of plasmids pAF 2-3, pAF 2-6, and pAF 2-7 have been determined completely using the dideoxy chain termination method (Sanger et al. (1977) Proc. Natl. Acad. Sci. USA 74, 5463–5467) and shotgun strategies described by Messing et al. (1981, Nucl. Acids Res. 9, 309–321). In addition specific oligonucleotides were synthesized based on nucleotide sequence information obtained during, the sequencing procedure.

Figure 7:
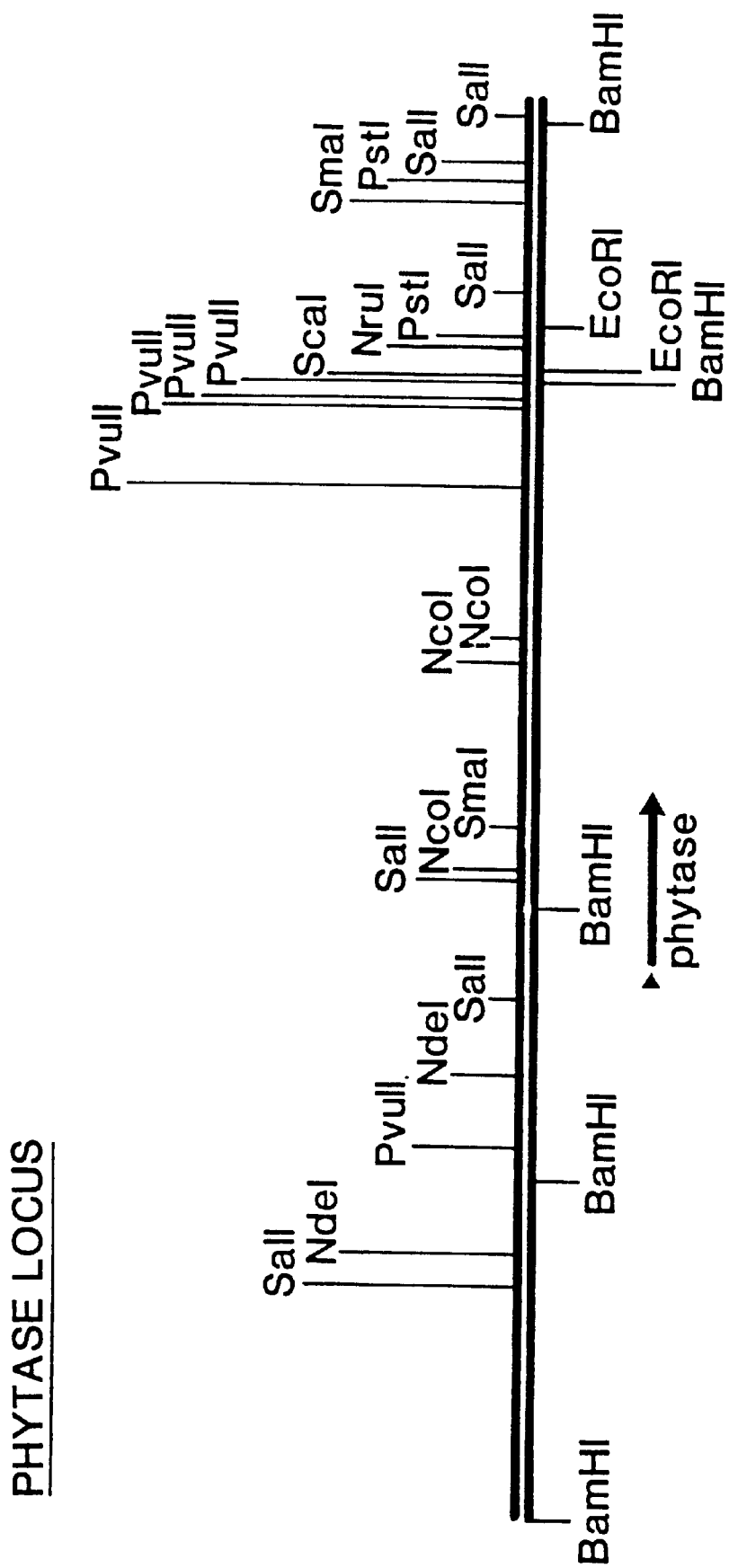
FIG. 7. Detailed physical map of the sequenced phytase chromosomal locus; the arrows indicate the location of the two exons of the phytase coding region.

The complete nucleotide sequence of clones pAF 2-3, pAF 2-6, and pAF 2-7 encompassing the chromosomal phytase gene locus is compiled in FIG. 6, a graphic representation is given in FIG. 7.

Analysis of the protein coding capacity of the complete sequence revealed that the N-terminal amino acid sequence of the mature protein was encoded starting from nucleotide position 381 (the N-terminus disclosed by Ullah is located at position 369). Furthermore, the N-terminal amino acid sequence of the 36 kDa and 2.5 kDa internal peptide fragments (see FIG. 1B—sequences B and A) were found to be encoded at nucleotide positions 1101 and 1548, respectively. The open reading frame stops at nucleotide position 1713.

These findings clearly prove the identity of the characterized chromosomal locus as containing phytase encoding DNA sequence.

Directly upstream of the chromosomal sequence encoding the mature phytase protein, no ATG start codon can be found within the reading frame contiguous with the mature protein open reading frame; however, using intron-exon boundary characteristics, an intron can be postulated between nucleotide positions 254 and 355, bringing the ATG codon at nucleotide position 210 in frame with the mature phytase encoding open reading frame. The derived amino acid sequence of this N-terminal extension closely fits the rules for a secretion signal sequence as published by von Heyne (1983, Eur. J. Biochem. 133, 17–21).

To confirm these hypotheses the phytase cDNA was isolated by PCP-amplification with specific phytase primers and a total mRNA/cDNA population as template according to the procedures described below.

Isolation of Poly A$^+$ RNA from *Aspergillus ficuum*

Total RNA was isolated from *A. ficuum* NRRL 3135 grown under induced conditions as mentioned in Example 6. Dry mycelium was frozen with liquid nitrogen and ground. Subsequently, the powder was homogenized in an Ultra-Turrax (full speed during 1 minute) in 3M LiCl, 6M urea at 0° C. and maintained overnight at 4° C. as described by Auffrey & Rougeon (Eur.J.Biochem., 107, 303–314,1980). Total cellular RNA was obtained after centrifugation at at 16,000 g for 30 minutes and two successive extractions with phenol:chloroform:isoamylalcohol (50:48:2). The RNA was precipitated with ethanol and dissolved in 1 ml 10 mM Tris-HCl (pH 7.4), 0.5% SDS. For poly A$^+$ selection the total RNA sample was heated for 5 minutes at 60° C., adjusted to 0.5 M NaCl and subsequently applied to an oligo(dT)-cellulose column. After several washes with a solution containing 10 mM Tris-HCl pH 7.4, 0.5% SDS and 0.1 M NaCl, the poly A$^+$ RNA was collected by elution with 10 mM Tric-HCl pH 7.4 and 0.5% SDS.

Preparation of the mRNA/cDNA Complex

For the synthesis of the first cDNA strand 5 $\mu$g of poly A$^+$ RNA was dissolved in 16.5 $\mu$l H$_2$O and the following components were added: 2.5 $\mu$l RNasin (30 U/$\mu$l); 10 $\mu$l of a buffer containing 50 EM Tris-HCl pH 7.6, 6 mM MgCl$_2$ and 40 mM KCl; 2 $\mu$l 1 M KCl; 5 $\mu$l 0.1 M DTT; 0.5 $\mu$l oligo (dT)$_{12-18}$ (2.5 mg/ml); 5 $\mu$l 8 mM dNTP-mix; 5 $\mu$l BSA (1 mg/ml) and 2.5 $\mu$l Moloney MLV reverse transcriptase (200 U/ml). The mixture was incubated for 30 minutes at 37° C. and the reaction was stopped by addition of 10 $\mu$l 0.2 M EDTA, and 50 $\mu$l H$_2$O. An extraction was performed with chloroform and after centrifugation 110 $\mu$l 5 M NH$_4$Ac and 440 $\mu$l ethanol were successively added to the supernatant. Precipitation of the mRNA/cDNA complex was performed in a dry ice/ethanol solution for 30 minutes. The mRNA/cDNA was collected by centrifugation, subsequently washed with 70% ice-cold ethanol and dissolved in 20 $\mu$l H$_2$O.

Cloning of Phytase cDNA Fragments

Isolation of the cDNA-encoding phytase sequences were performed by the polymerase chain reaction (PCR) in two fragments. Four synthetic oligonucleotide primers were designed based on the genomic phytase sequence as presented in FIG. 6.

Oligo 1:
5'-GGG.TAG.AAT.TCA.AAA.ATG.GGC.GTC.TCT.GCT.GTT.CTA-3'(SEQ ID NO:34)

Oligo 2:
5'-AGT.GAC.GAA.TTC.GTG.CTG.GTG.GAG.ATG.GTG.TCG-3'(SEQ ID NO:35)

Oligo 3: 5'-GAG.CAC.CAA.GCT.GAA.(GGA.TCC-3'(SEQ ID NO:36)

Oligo 4:
5'-AAA.CTG.CAG.GCG.TTG.AGT.GTG.ATT.GTT.TAA.AGG.G-3'(SEQ ID NO:37)

Oligo 1 contains the nucleotide sequence downstream of the phytase ATG startcodon (position 210 to 231) flanked at the 5' border by an EcoRI-site; oligo 2 contains the nucleotide sequence immediately upstream of the SalI-site (position 1129 to 1109) also flanked by an additional EcoRI-site; oligo 3 contains the nucleotide sequence around the BamHI-site (position 845 to 865) and oligo 4 contains a nucleotide sequence positioned downstream of the phytase stopcodon (position 1890 to 1867) flanked by an additional PstI-site.

The polymerase chain reactions were performed according to the supplier of Taq-polymerase (Cetus). As template the solution (1.5 µl) containing the mRNA/cDNA hybrids (described above) was used and as primers 0.3 µg of each of the oligos 1 and 2 in the reaction to amplify the N-terminal phytase cDNA part and oligos 3 and 4 in the reaction to amplify the C-terminal phytase cDNA part (see FIG. 8). After denaturation (7 minutes at 100° C.) and addition of 2 U Taq-polymerase the reaction mixtures were subjected to 25 amplification cycles (each: 2' at 55° C., 3' at 72° C., 1' at 94° C.) in a DNA-amplifier of Perkin-Elmer/Cetus. In the last cycle the denaturation step was omitted. After digestion (EcoRI for the N-terminal cDNA part and BamHI and PstI for the C-terminal cDNA part), both cDNA fragments were cloned into the appropiate sites of pTZ18R (Promega).

The nucleotide sequence of both obtained PCR fragments was determined using the dideoxy chain termination technique (Sanger, supra) using synthetic oligonucleotides designed after the chromosomal phytase gene sequence, as primers and total amplified DNA as well as cloned cDNA fragments as template. The sequence of the cDNA region encoding the phytase protein and the derived amino acid sequence of the phytase protein are depicted in FIG. 8.

The cDNA sequence confirmed the location of the intron postulated above, and indicated that no other introns were present within the chromosomal gene sequence.

The phytase gene encodes a primary translation product of 467 amino acids (MW 51091); processing of the primary translation product by cleaving off the signal peptide results in a mature phytase protein of 444 (MW 48851) or 448 (containing the first four N-terminal amino acids as published by Ullah, MW 49232) amino acids.

EXAMPLE 9

Overexpression of Phytase in Aspergilli by Introduction of Additional Phytase Genomic DNA Copies
Construction Expression Vector pAF 2-2S All constructs were made using standard molecular biological procedures, as described by Maniatis et al., (1982) Molecular cloning, A laboratory Manual, Cold Spring Harbor Laboratory, N.Y.

Figure 9:
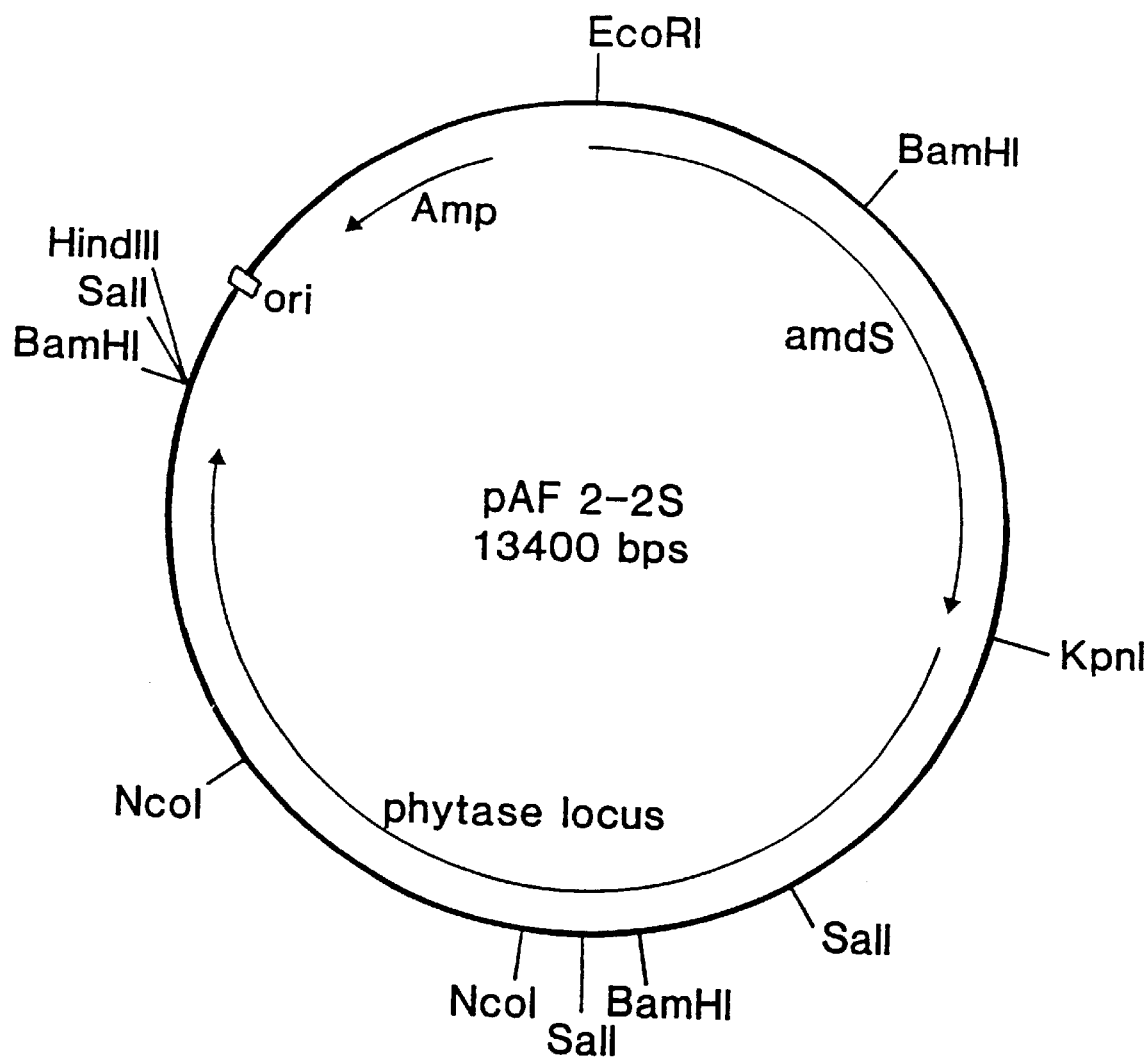
FIG. 9. Physical map of the phytase expression cassette pAF 2-2S. Arrows indicate the direction of transcription of the genes.

An expression vector pAF 2-2S was made by subcloning the 6 kb PvuII DNA fragment of the phytase genomic clone lambda AF201, into the SmaI-site of pUC19. The derived plasmid was designated pAF 2-2 (FIG. 4). As selection marker for the transformation to Aspergillus, the EcoRI/KpnI DNA fragment of plasmid pGW325 (Wernars K. (1986), Thesis, Agriculture University, Wageningen, The Netherlands) containing the homologous Aspergillus nidulans amdS gene, was inserted into the EcoRI/KpnI sites of pAF 2-2. The resulting expression vector was designated pAF 2-2S and is shown in FIG. 9.

A. Overexpression of Phytase in *A. ficuum* NRRL 3135

The plasmid pAF 2-2S was introduced in *A. ficuum* NRRL 3135 using transformation procedures as described by Tilburn, J. et.al. (1983) Gene 26, 205–221 and Kelly, J. & Hynes, M. (1985) EMBO J., 4, 475–479 with the following modifications:

mycelium was grown on Aspergillus minimal medium (Cove, D. (1966) Biochem. Biophys. Acta, 113, 51–56) supplemented with 10 mM arginine and 10 mM proline for 16 hours at 30° C. in a rotary shaker at 300 rpm:

only Novozym 234 (NOVO Industri), and no helicase, was used for formation of protoplasts;

after 90 minutes of protoplast formation, 1 volume of STC buffer (1.2 M sorbitol, 10 mM Tris-HCl pH 7.5, 50 mM $CaCl_2$) was added to the protoplast suspension and centrifuged at 2500 g at 4° C. for 10 minutes in a swinging-bucket rotor. The protoplasts were washed and resuspended in STC-buffer at a concentration of $10^8$ cells/ml plasmid DNA was added in a volume of 10 µl in TE buffer (10 mM Tris-HCl pH 7.5, 0.1 mM EDTA) to 100 µl of the protoplast suspension;

after incubation of the DNA-protoplast suspension at 0° C. for 25 minutes, 200 µl of PEG solution was added dropwise (25% PEG4000 (Merck), 10 mM Tris-HCl pH 7.5, 50 mM $CaCl_2$). Subsequently, 1 ml of PEG solution (60% PEG 4000 in 10 mM Tris-HCl pH 7.5, 50 mM $CaCl_2$) was added slowly, with repeated mixing of the tubes. After incubation at room temperature, the suspensions were diluted with STC-buffer, mixed by inversion and centrifuged at 2000 g at 4° C. for 10 minutes. The protoplasts were resuspended gently in 200 µl STC-buffer and plated on Aspergillus minimal medium with 10 mM acetamide as the sole nitrogen source, 15 mM CsCl, 1 M sucrose, solidified with 0.75% bacteriological agar #1 (Oxoid). Growth was performed at 33° C. for 6–10 days.

Single transformants designated SP4, SP7 and SP8 were isolated, purified and tested for phytase production in shake flasks, using the process as described in Examples 1 and 2. As a control, transformants possessing only the vector (amdS gene in pUC19), as well as the untransformed host were tested.

Strains were grown under induced conditions (see Example 6) and samples were taken after 96 hours of growth. Analyses were performed by measuring the phytase activity (Table 4) and by isoelectric focusing polyacrylamide gelelectrophoresis (IEF-PAGE).

Figure 10A:
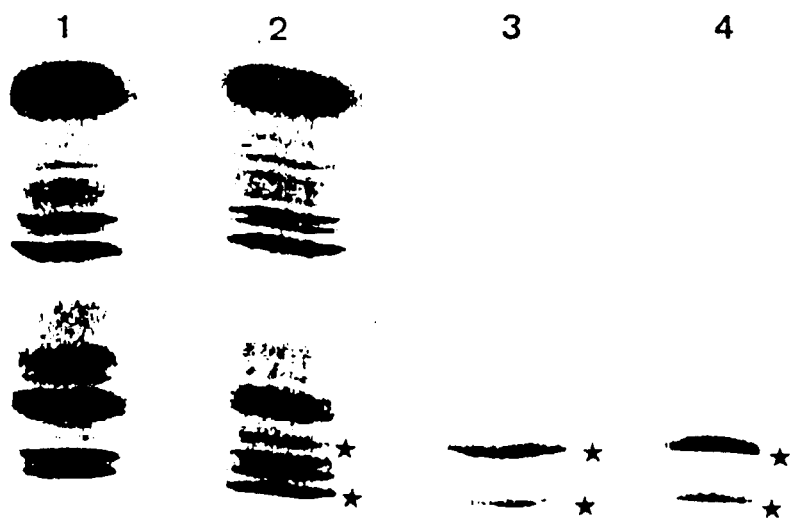
FIG. 10. IEF-PAGE evidence of the overexpression of phytase in an A. ficuum NRRL 3125 transformant. Equal volumes of culture supernatant of A. ficuum (lane 1) and transformant pAF 2-2S SP7 (lane 2), grown under identical conditions, were analysed on a Phast-System (Pharmacia) IEF-PAGE gel in the pH-range of 4.5–6. For comparison, a sample of A. ficuum phytase, purified to homogeneity was included either separately (lane 4), or mixed with a culture supernatant (lane 3). The gels were either stained with a phosphatase stain described in the text (A), or with a general protein stain (Coomassie Brilliant Blue, B). The phytase bands are indicated by an asterisk.
Figure 10B:
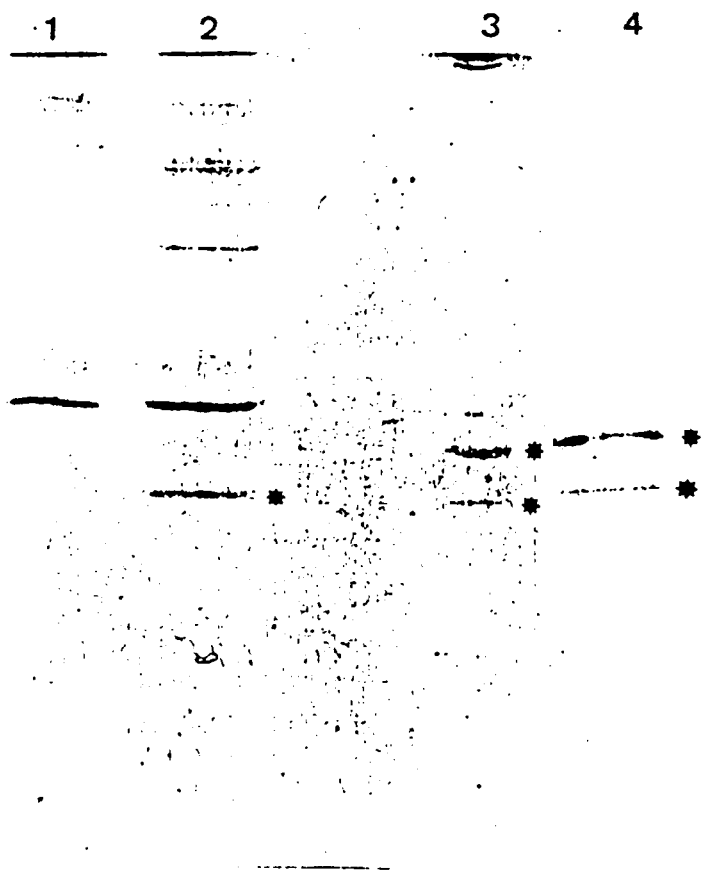

Samples of equal volume were taken from fermentations of *A. ficuum* and *A. ficuum* pAF 2-2S SP7, grown under identical conditions, and were applied onto an IEF-PAGE gel (pH-range 4.5–6, Phast-System, Pharmacia). The elactrophoresis was performed according to the instructions of the manufacturer. Subsequently, the gels were either stained with the general protein stain Coomassie Briliant Blue (FIG. 10B), or with the general phosphatase activity staining described in Example 2 (FIG. 10A).

A sample of *A. ficuum* phytase, purified to homogeneity (via immunoaffinity chromatography as described in Example 7), was also applied either alone, or mixed with a culture supernatant.

Phytase is present in the various samples in a number of isoforms (indicated with an asterisk), as has been mentioned in this invention. The two major isoenzymes are clearly visible in the purified phytase in lanes 3 and 4 with both staining procedures (A and B). The phytase bands are barely visible in the parent *A. ficuum* strain, and significantly increased in the pAF 2-2S SP7 transformant strain.

TABLE 4

Increase of phytase production
by transformation of *A. ficuum* NRRL 3135.

| Strain | Phytase activity (U/ml) |
| --- | --- |
| A. ficuum | 0.6 |
| A. ficuum + control plasmid | 0.6 |
| A. ficuum pAF 2-2S SP8 | 7.6 |
| A. ficuum pAF 2-2S SP7 | 6.7 |
| A. ficuum pAF 2-2S SP4 | 4.3 |

B. Overexpression of Phytase in *A. niger* CBS 513.88

The expression vector pAF 2-2S was also introduced in *A. niger* CBS 513.88 by transformation procedures as described for *A. ficuum*. Single transformants were isolated, purified and tested for phytase production in shake flasks under induced growth conditions as described in Example 6.

Phytase expression levels of some transformants (designated as *A. niger* pAF 2-2S #8, #20 and #33) and control strains were performed as described in Example 9A and are shown in Table 5.

*A. niger* transformants have phytase expression levels comparable with *A. ficuum* transformants. In addition this result indicates that the *A. ficuum* phytase promoter is active in *A. niger*.

Further analysis was performed on culture medium of transformant pAF 2-2S #8 by electrophoresis on an IEP-PAGE gel in the pH range of 4.5–6 on a Phast-System (Pharmacia) as described above. Equal volumes of the culture supernatants of the *A. niger* parent strain and of the transformant pAF 2-2S #8, grown under identical conditions, were applied onto the gel. The gels were run and subsequently stained as above.

Figure 11A:
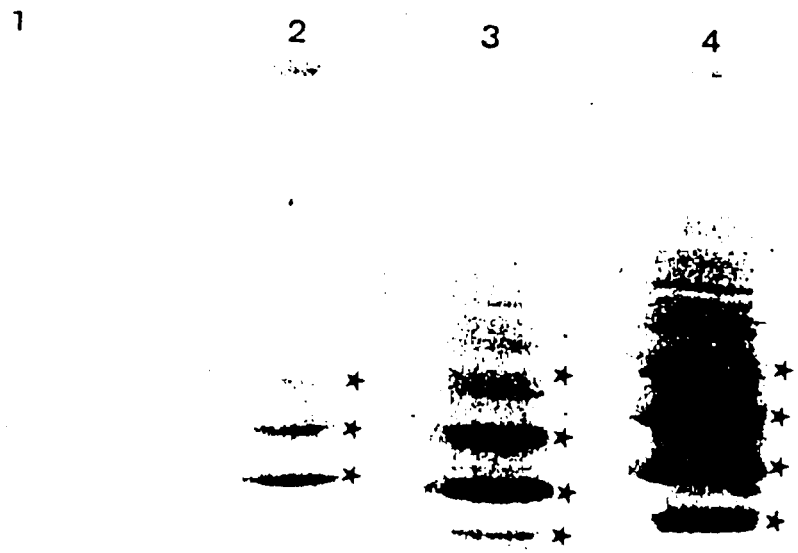
FIG. 11. IEF-PAGE evidence for the overexpression of phytase in A. niger CBS 513.88 transformants. Equal volumes of culture supernatants of the A. niger parent strain (lane 1), or the transformants pAF 2-2S #8 (lane 2), pFYT3 #205 (lane 3) & #282 (lane 4) were analysed by IEF-PAGE as described in the legend of FIG. 10. The gels were either stained by a general phosphatase activity stain (A) or by a general protein stain (B). Phytase bands are indicated by an asterisk.
Figure 11B:

The parent *A. niger* produces a very low amount of phytase, which could not be detected by gel electrophoresis. The strain pAF 2-2S #8 produces approx. 90 times more phytase, and this difference is clearly visible in FIG. 11.

Several isoforms of the phytase enzyme are detected (indicated by asterisk). The general protein stain indicates that the intensity of the phytase protein bands is dramatically increased, while no other major protein bands appear.

TABLE 5

Phytase production by transformation
of *A. niger* CBS 513.88 with pAF 2-2S.

| Strain | Phytase activity (U/ml) |
| --- | --- |
| A. niger | 0.2 |
| A. niger + control plasmid | 0.2 |
| A. niger pAF 2-2S # 8 | 14 |
| A. niger pAF 2-2S # 33 | 5 |
| A. niger pAF 2-2S # 20 | 4 |

EXAMPLE 10

Phytase Expression in *A. niger* Transformed with Expression Vectors Containing the *A. ficuum* Phytase Gene Fused to the Promoter and/or Signal Sequences of the *A. niger* Amyloglucosidase (AG) Gene Constructions of the Expression Vectors To obtain overexpression of phytase in *A. niger*, additional expression cassettes are derived in which the *A. ficuum* phytase gene is under control of the *A. niger* amyloglucosidase (AG) promoter in combination with different signal sequences. In p18FYT3 and p24FYT3 the respective 18 and 24 amino acid (aa) leader sequences of the AG gene from *A. niger* are fused to the phytase gene fragment encoding the mature protein. In the expression cassette pFYT3 the AG promoter sequence is fused to the phytase encoding sequence including the phytase leader sequence.

Construction of p18FYT3

Figure 12:
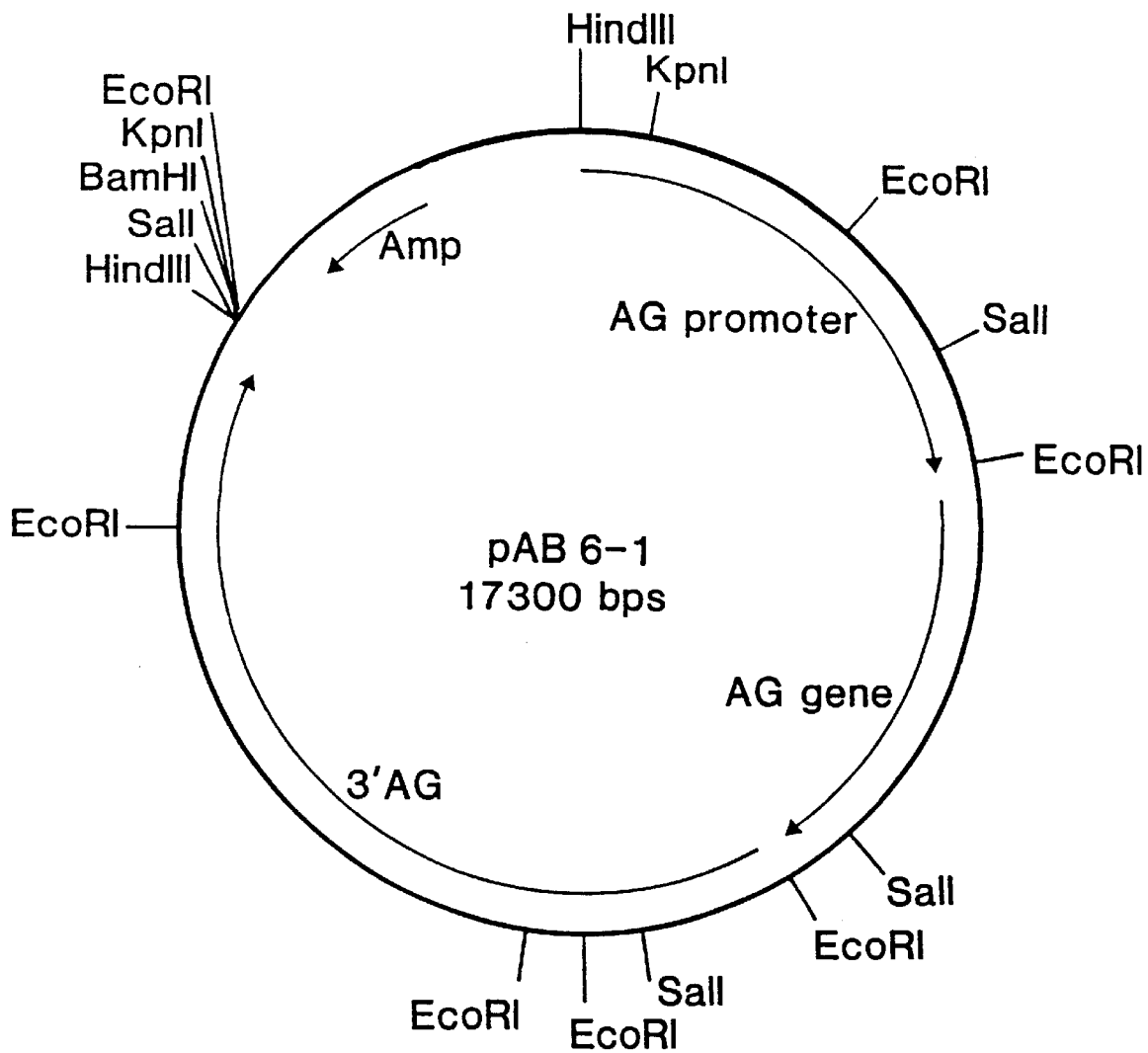
FIG. 12. Physical map of pAB 6-1. The 14.5 kb HindIII DNA insert in pUC19 contains the entire glucoamylase (AG) locus from A. niger.

Fusion of the AG-promoter and the 18 aa AG-leader sequence to the phytaga gequenea enCoding the mature protein were performed by the Polymerase Chain Reaction method. In the PCR reactions two different templates were used: pAF 2-2S containing the entire phytase gene as described above and pAB6-1, a plasmid which contains the entire AG-locus from *A. niger*, which was isolated from a *A. niger* plasmid library, containing 13–15 kb HindIII fragments in pUC19. For the isolation, AG-specific oligos were used:

AG-1:
5'-GACAATGGCTACACCAGCACCGCAACGGACA TTGTTTGGCCC-3'(SEQ ID NO:38)
AG-2: 5'-AAGCAGCCATTGCCCGAAGCCGAT-3'(SEQ ID NO:39)

both based on the nucleotide sequence published for *A. niger* (Boel et al.(1984), EMBO J. 3, 1097–1102; Boel et al. (1984), Mol. and Cell. Biol. 4, 2306–2315). The oligonucleotide probes were derived from the sequence surrounding intron 2: oligo AG-1 is located 3' of the intron and has a polarity identical to the AG mRNA and oligo AG-2 is found upstream of intron 2 and is chosen antiparallel to the AG mRNA. Plasmid pAB6-1 contains the AG gene on a 14.5 kb HindIII fragment (see FIG. 12).

As primers for the PCR-amplifications four synthetic oligonucleotides were designed with the following sequence:

Oligo 1: 5'-CTCTGCAG<u>GAATTC</u>AAGCTAG-3'(SEQ ID NO:40) (an AG-specific sequence around the EcoRI site approx. 250 bp upstream the ATG initiation codon).

Oligo 18-2:
5'-CGAGGCGGGGACTGCCAGTGCCAACCCTGT GCAGAC-3'(SEQ ID NO:41) mature phytase <—> 18 AA AG-leader Oligo 18-3:
5'-GTCTGCACAGGGTTGGCACTGGCAGTCCCCG CCTCG-3'(SEQ ID NO:42) 18 aa AG-leader <—> mature phytase Oligo 4: 5'-GGCACGA<u>GGATCC</u>TTCAGCTT-3'(SEQ ID NO:43) (a phytase specific sequence located at the BamHI site on position 861)

The PCR was performed as described by Saiki et al. (1988), Science 239, 487–491, with minor modifications (see Example 8).

Figure 13:
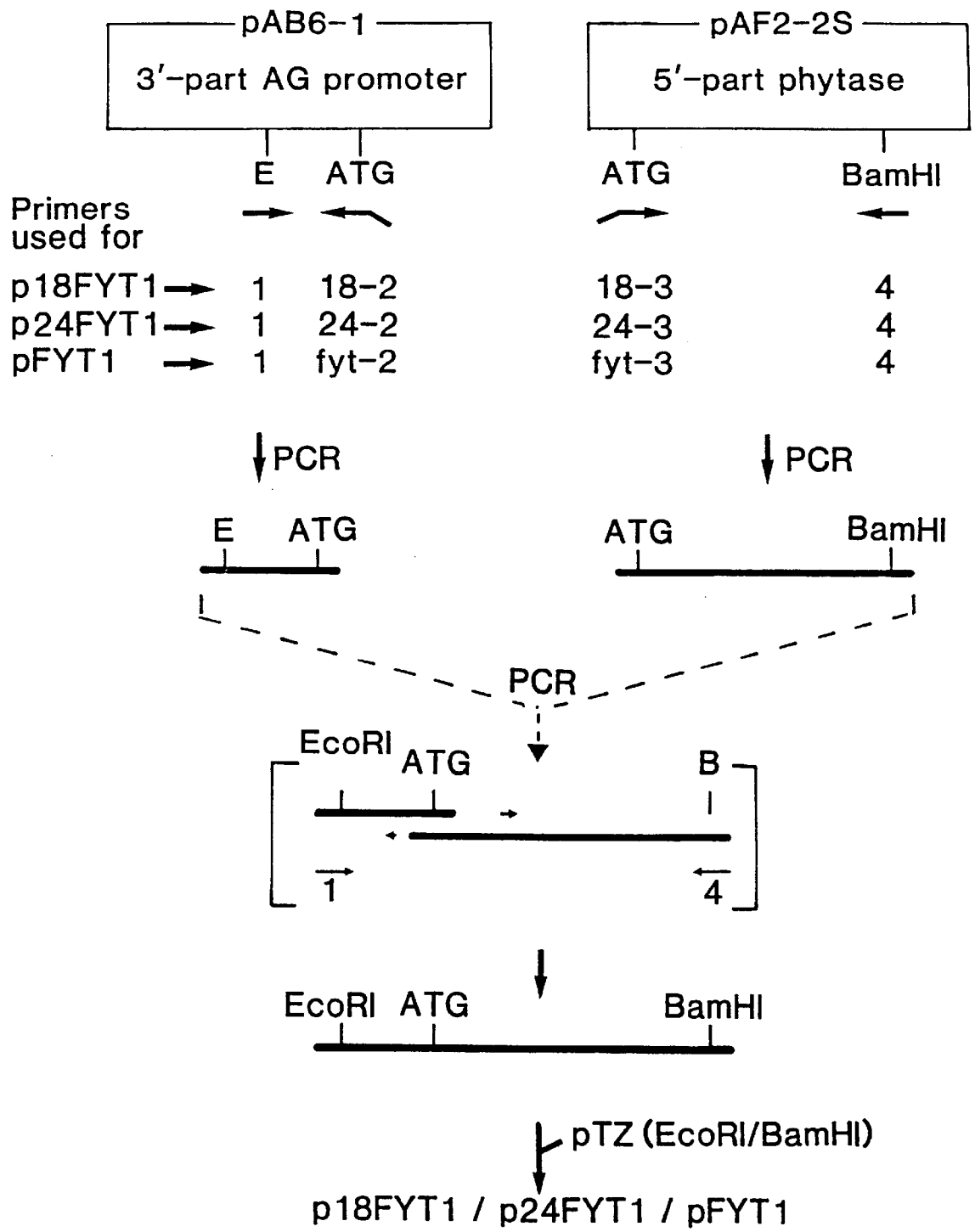
FIG. 13. A schematic view of the generation of AG promoter/phytase gene fusions by the polymerase chain reaction (PCR). The sequences of all oligonucleotide primers used are indicated in the text.

To fuse the AG sequences to the phytase coding sequences two separate PCR's were carried out: the first reaction with pAB6-1 as template and oligos 1 and 18-2 as primers to amplify a 300 bp DNA fragment containing the 3'-part of the AG promoter and the 18 aa AG-leader sequence flanked at the 3'-border by the nucleotides of the phytase gene, and the second reaction with pAF 2-2S as template and oligos 18-3 and 4 as primers to amplify a 600 bp DNA fragment containing the 5' part of the phytase gene flanked at the 5'-border by 18 nucleotides of the AG signal peptide. A schematic view of these amplifications is presented in FIG. 13.

The two DNA fragments generated were purified by gelelectrophoresis and ethanol precipitation and used as templates in the third PCR with oligos 1 and 4 as primers to generate the AG-phytase fusion. The obtained DNA fragment was digested with EcoR1 and BamHI and subcloned into pTZ18R. The resulted fusion was sequenced and designated p18FYT1.

Figure 15A:
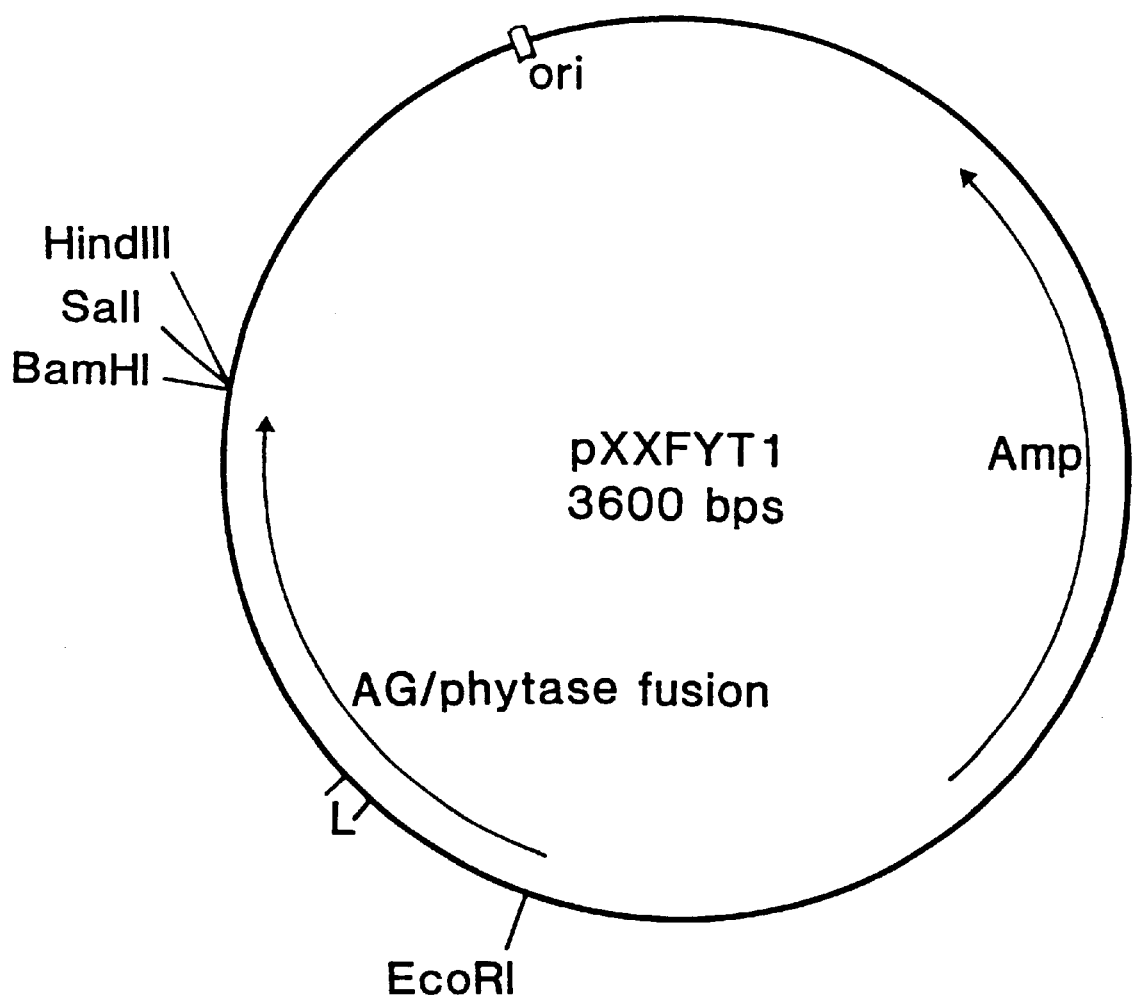
FIG. 15. Physical maps of the intermediate constructs pXXFYT1, pXXFYT2 and the phytase expression cassettes pXXFYT3, wherein XX indicates the leader sequence (L). In p18FYT# and p24FYT#, respectively the 18 aa and the 24 aa AG leader sequence are inserted whereas in pFYT#, the phytase leader is used.
Figure 15B:
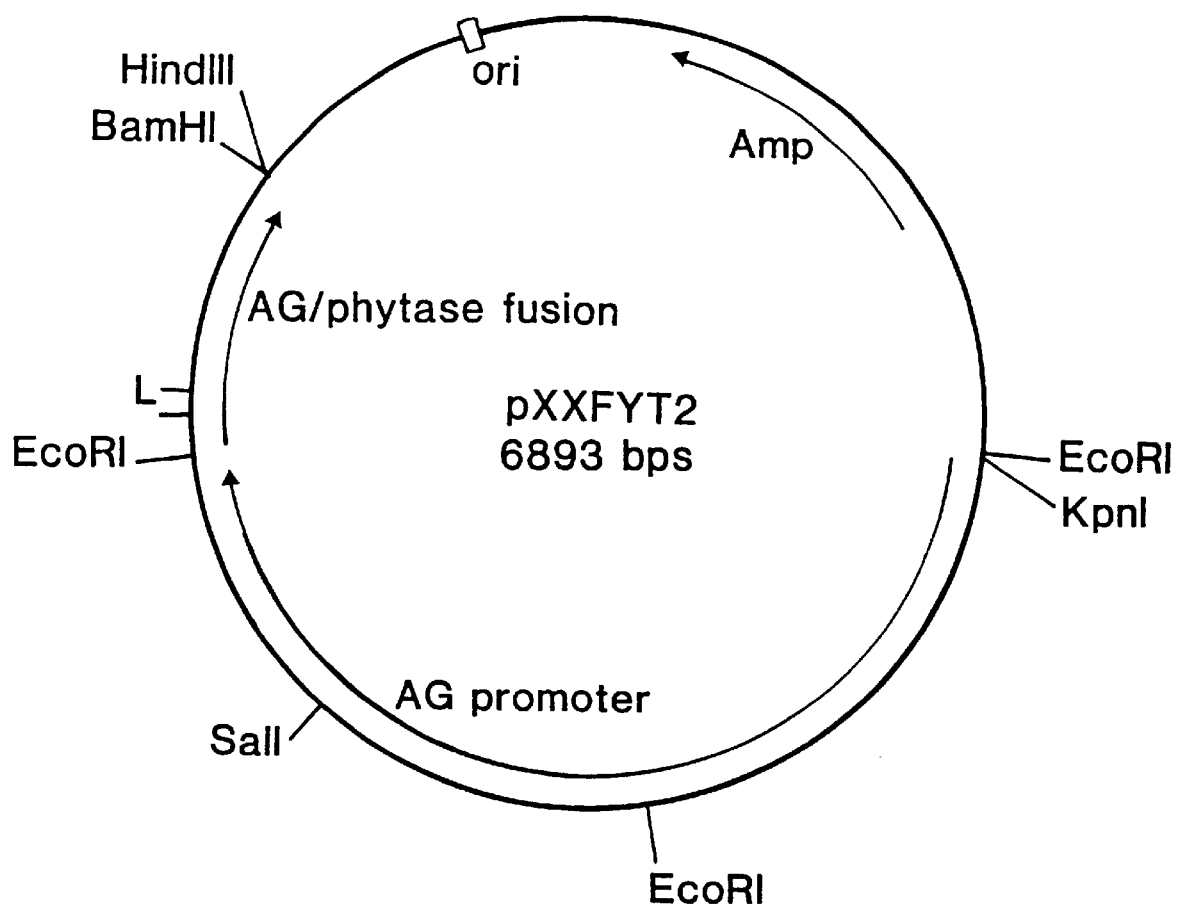
Figure 15C:
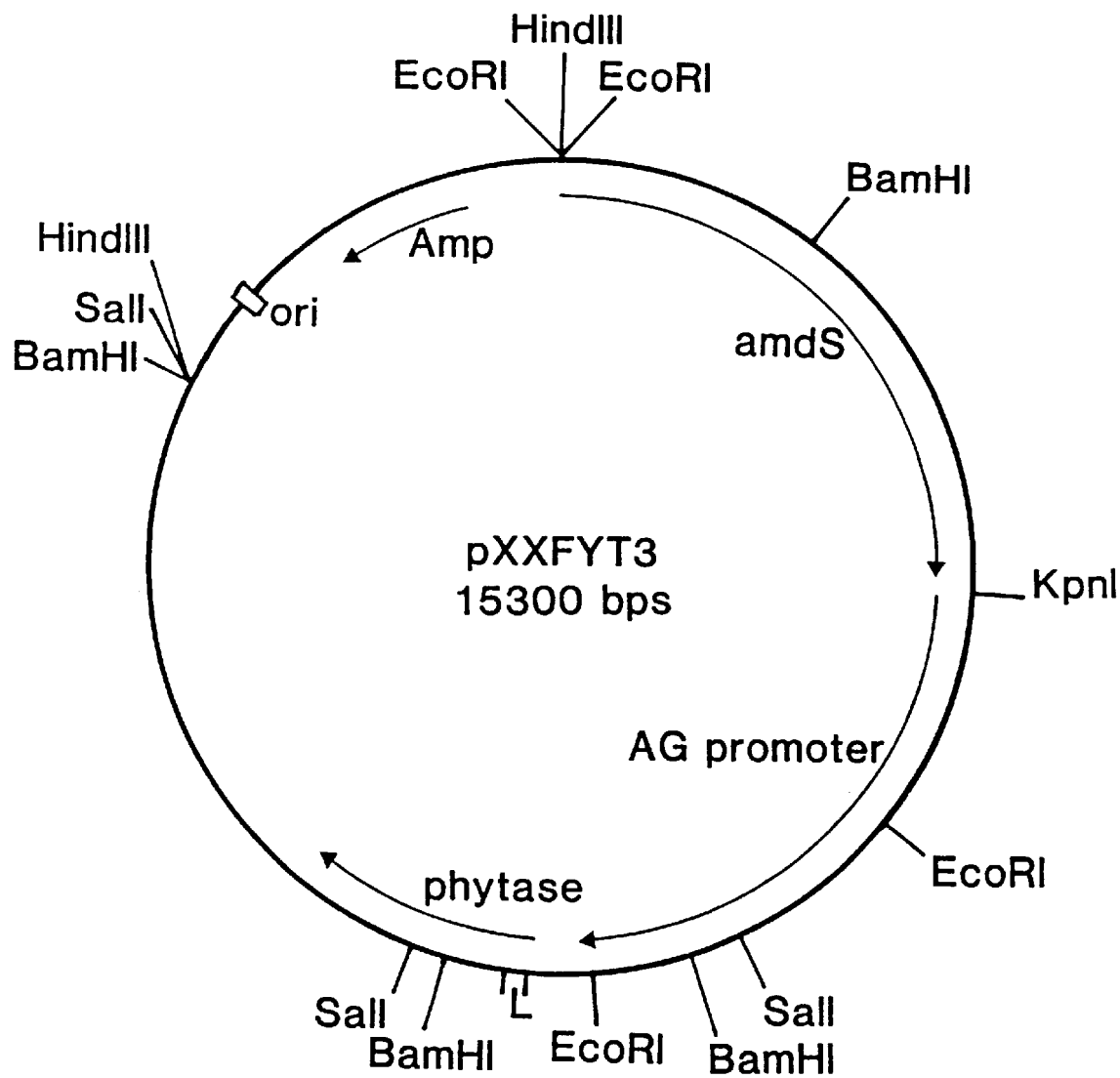

The remaining (3.5 Kb) upstream region of the AG-promoter was obtained by digestion of pAB6-1 with Kpn1 and partially with EcoR1 and ligated to the 1.1 Kb EcoR1/BamHI fragment of p18FYT1 and subsequently cloned into the Kpn1-/BamHI sites of pTZ18R. Plasmid p18FYT2 thus obtained is shown in FIG. 15.

Figure 14:
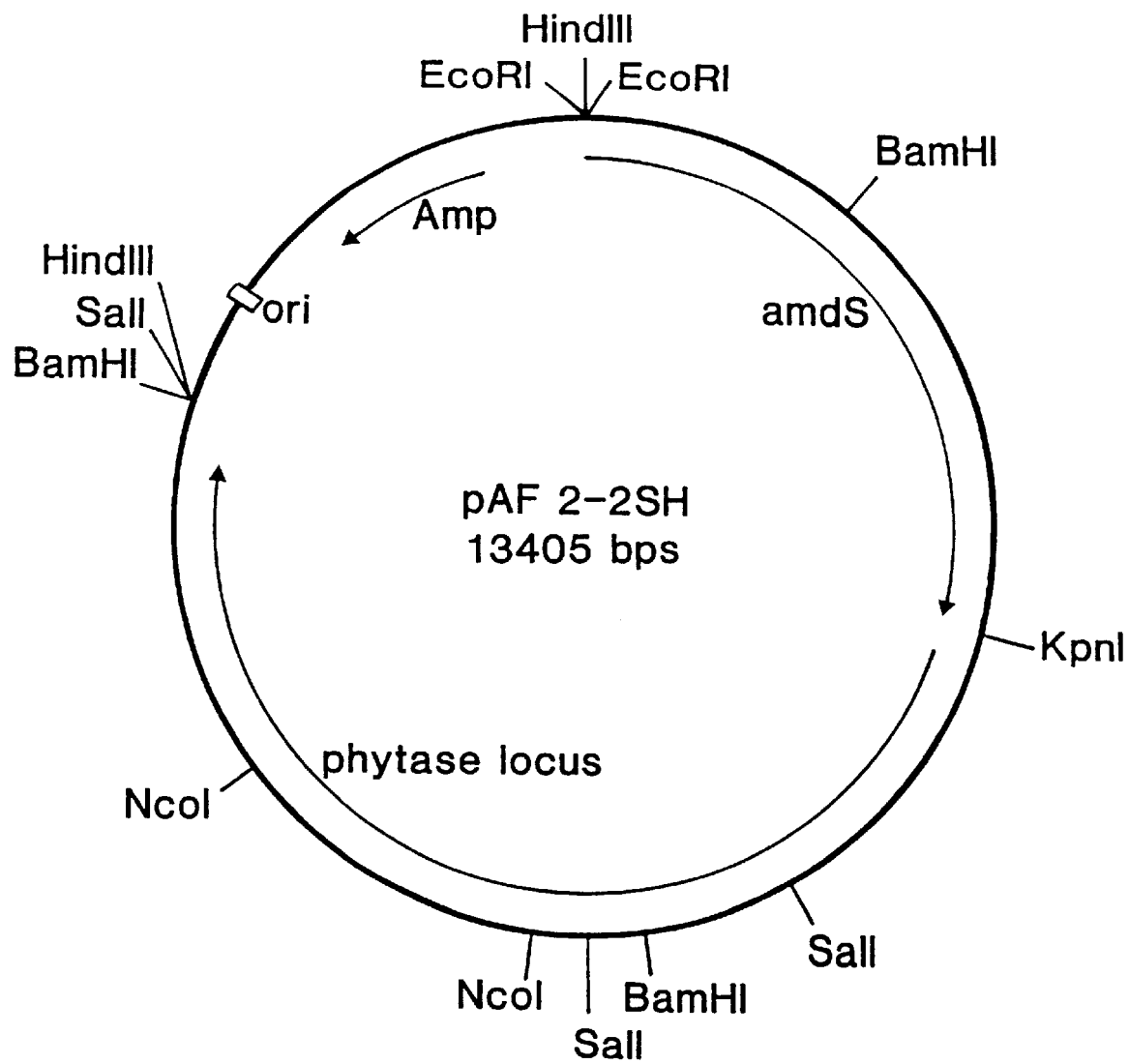
FIG. 14. Physical map of the phytase expression cassette pAF 2-2SH.

An additional HindIII restriction site was introduced by insertion of the synthetic fragment:
5' AATTCAAGCTTG 3'(SEQ ID NO:44)
3' GTTCGAACTTAA 5'(SEQ ID NO:44)
into the EcoRI-site (flanking the amdS-gene) of pAF 2-2S. The obtained plasmid was designated pAF 2-2SH (FIG. 14) and is used as starting plasmid to exchange the phytase promoter sequences by the PCR AG-phytase fusion DNA fragments.

For the final construction, p18FYT2 and pAF 2-2SH were digested with KpnI and partially with BamHI. The 4.6 kb DNA fragment of p18FYT2 and the 11 kb DNA fragment of pAF 2-2SH were isolated and purified by gel electrophoresis, subsequently ligated and transferred to *E. coli*. The derived expression cassette was designated p18FYT3 (FIG. 15).

Construction of p24FYT3

Fusion of the AG-promoter and the 24 aa AG leader sequence to the mature phytase encoding sequence was performed by PCR-amplification as described above for the construction for p18FYT3 with the exception of the primers used. Two new primers were synthesized with the following sequence:

Oligo 24-2:
5'-CGAGCCGGGGACTGCCAGGCGCTTGGAAATC
ACATT-3'(SEQ ID NO:45) mature phytase <—> 24 AA AG-leader Oligo 24-3:
5'-AATGTGATTTCCAAGCGCCTGGCAGTCCCCG
CCTCG-3'(SEQ ID NO:46) 24 aa AG-leader <—> mature phytase Two separate PCR's were carried out: the first reaction with pAB 6-1 as template and oligos 1 and 24-2 as primers to amplify a 318 bp DNA fragment containing the 3'-part of the AG promoter and the 24 aa AG leader sequence flanked at the 3'-border by 18 nucleotides of the phytase gene and the second reaction with pAF 2-2S as template and oligos 24-3 and 4 as primers to amplify a DNA fragment containing the 5'-part of the phytase gene flanked at the 5'-border by 18 nucleotides of the 24 aa AG leader. A schematic view of these amplifications is presented in FIG. 13.

For the construction of the final expression cassette p24FYT3 via the intermediate plasmids p24FYT1 and p24FYT2, the same cloning pathway/procedure was used as described for p18FYT1 and p18FYT2 to derive the expression cassette p18FYT3 (FIG. 15).

Construction of pFYT3

Fusion of the AG-promoter to the phytase gene (including the phytase leader) sequence was also performed by PCR-amplification as described above for the construction of p18FYT3 with the exception of the primers used. Two additional primers were generated with the following sequence:

Oligo fyt-2:
5'-AACAGCAGAGACGCCCATTGCTGAGGTGTAA
TGATG-3'(SEQ ID NO:47) phytase leader <—> AG-promoter Oligo fyt-3:
5'-CATCATTACACCTCAGCAATGGGCGTCTCTGC
TGTT-3'(SEQ ID NO:48) AG-promoter <—> phytase leader Two separate PCR's were carried out: the first reaction with pAB 6-1 as template and oligos 1 and fyt-2 as primers to amplify a 282 bp DNA fragment containing the 3'-part of the AG promoter flanked at the 3'-border by 18 nucleotides of the phytase leader and the second reaction with pAF 2-2S as template and oligos fyt-3 and 4 as primers to amplify a DNA-fragment containing the 5'-part of the phytase gene (including the phytase leader) and flanked at the 5'-border by 18 nucleotides of the AG-promoter. A schematic view of these amplifications is presented in FIG. 13.

For the construction of the final expression cassette pFYT3 along the intermediate plasmids pFYT1 and pFYT2, the same cloning pathway/procedure was used as described for p18FYT1 and p18FYT2 to derive the expression cassette p18FYT3 (FIG. 15).

Expression of the Phytase Gene Under the Control of the AG Promoter in *A. niger*

*E. coli* sequences were removed from the phytase expression cassettes described above by HindIII digestion. Afterwards, the *A. niger* strain CBS 513.88 (deposited Oct. 10, 1988) was transformed with 10 μg DNA fragment by procedures as described in Example 9. Single *A. niger* transformants from each expression cassette were isolated, and spores were streaked on selective acetamide-agar plates. Spores of each transformant were collected from cells grown for 3 days at 37° C. on 0.4% potato-dextrose (Oxoid, England) agar plates. Phytase production was tested in shake flasks under the following growth conditions:

Approximately 1×10$^8$ spores were inoculated in 100 ml pre-culture medium containing (per liter): 1 g KH$_2$PO$_4$; 30 g maltose; 5 g yeast-extract; 10 g casein-hydrolysate; 0.5 g MgSO$_4$.7H$_2$O and 3 g Tween 80. The pH was adjusted to 5.5.

After growing overnight at 34° C. in a rotary shaker, 1 ml of the growing culture was inoculated in a 100 ml main-culture containing (per liter): 2 g KH$_2$PO$_4$; 70 g malto-dextrin (Maldex MDO$_3$, Amylum); 12.5 g yeast-extract; 25 g casein-hydrolysate; 2 g K$_2$SO$_4$; 0.5 g MgSO$_4$.7H$_2$O; 0.03 g ZnCl$_2$; 0.02 g CaCl$_2$; 0.05 g MnSO$_4$.4 H$_2$O and FeSO$_4$. The pH was adjusted to 5.6.

The mycelium was grown for at least 140 hours. Phytase production was measured as described in Example 2. The production results of several, random transformants obtained from each expressiontcessette are shown in Table 6.

TABLE 6

Phytase production of several *A. niger* CBS 513.88 strains transformed with plasmids containing the *A. ficuum* phytase gene under control of the *A. niger* AG-promoter in combination with different leader sequences.

| Expression cassette | Transformant # | Phytase activity (U/ml) |
|---|---|---|
| p18FYT3 | p18FYT3 # 240 | 82 |
| (AG-promoter/ | p18FYT3 # 242 | 84 |
| 18 aa AG-leader) | p18FYT3 # 243 | 62 |
| | p18FYT3 # 244 | 43 |
| | p18FYT3 # 245 | 80 |
| | p18FYT3 # 246 | 82 |
| | P18FYT3 # 250 | 110 |
| p24FYT3 | p24FYT3 # 256 | 8 |
| (AG-promoter/ | p24FYT3 # 257 | 30 |
| 24 aa AG-leader) | p24FYT3 # 258 | 13 |
| | p24FYT3 # 259 | 33 |
| | p24FYT3 # 260 | 17 |
| | p24FYT3 # 261 | 28 |
| | p24FYT3 # 262 | 18 |
| | p24FYT3 # 265 | 12 |
| pFYT3 | pFYT3 # 205 | 50 |
| (AG-promoter/ | pFYT3 # 282 | 280 |
| phytase leader) | pFYT3 # 299 | 96 |
| | pFYT3 # 302 | 220 |
| | pFYT3 # 303 | 175 |

TABLE 6-continued

Phytase production of several *A. niger* CBS 513.88 strains transformed with plasmids containing the *A. ficuum* phytase gene under control of the *A. niger* AG-promoter in combination with different leader sequences.

| Expression cassette | Transformant # | Phytase activity (U/ml) |
|---|---|---|
| | pFYT3 # 304 | 150 |
| | pFYT3 # 305 | 150 |
| | pFYT3 # 312 | 140 |

The data clearly show high phytase expression levels in *A. niger* transformants containing the phytase gene under the control of the *A. niger* AG promoter. The data also show that the highest phytase production is obtained with the pFYT3 expression vector, which contains the phytase leader sequence. Similar expression vectors containing an intronless phytase gene after transformation to *A. niger*, resulted in phytase expression levels comparable to pFYT3 transformants of *A. niger*.

In addition, electrophoresis on an IEF-PAGE gel in the pH-range of 4.5–6 was performed on culture supernatants of transformants pFYT3 #205 and #282. Equal volumes of the culture supernatants of the *A. niger* parent strain and of both transformants, grown under identical conditions, were applied onto the gel, run and subsequently stained as described in Example 9. The parent *A. niger* produces a very low amount of phytase, which is not detected in this experiment. The strains pFYT3 #205 and #282 produce approx. 250 and 1400 times more phytase (compare phytase levels in Tables 4 and 5), and this difference is clearly visible in FIG. 11. Several isoforms of the phytase enzyme are detected (indicated by an asterisk). The general protein stain indicates that the intensity of the phytase protein bands is dramatically increased, while no other major protein bands appear.

EXAMPLE 11

Overexpression of Phytase in *A. ficuum* and *A. niger* Grown on an Industrial Scale A. *A. ficuum*

Strain *A. ficuum* pAF 2-2S #4 and *A. ficuum* NRRL 3135 were grown as described in Example 1. The transformant produced approximately 50 times more phytase as compared to the wild-type strain.

TABLE 7

Overexpression of phytase by a transformant of *A. ficuum* containing multiple phytase genes. Cells were grown as described in Example 1.

| Hours after inoculation | Phytase activity *A. ficuum* NRRL 3135 | (U/ml Fermentation broth) *A. ficuum* pAF 2-2S #4 |
|---|---|---|
| 0 | 0 | 0 |
| 24 | 0 | 0 |
| 92 | 2 | 142 |
| 141 | 5 | 270 |

B. *A. niger*

Strain *A. niger* pAF 2-2S #8, a transformant of *A. niger* strain CBS 513.88 and the parent *A. niger* strain itself were grown as described in Example 1. The transformant produced approximately 1000 times more phytase as compared to the original *A. niger* parent strain (Table 8).

TABLE 8

Overexpression of phytase by a transformant of *A. niger* (CBS 513.88) containing multiple phytase genes. Cells were grown as described in Example 1.

| Hours after inoculation | Phytase activity *A. niger* CBS 513.88 | (U/ml Fermentation broth) *A. niger* pAF 2.2 #8 |
|---|---|---|
| 0 | 0 | 0 |
| 24 | 0 | 5 |
| 92 | 0.1 | 65 |
| 141 | 0.1 | 95 |

EXAMPLE 12

To contruct the vector pREPFYT3, with which simultaneously phytase expression and AG gene replacement is achieved, pFYT3 is digested with KpnI. With the obtained linear KpnI DNA fragment, two separate ligations are performed.

Ligation 1 with the KpnI-HindIII adaptor:

| 5'- | CGGGGA | -3' (SEQ ID NO: 49) |
|---|---|---|
| 3'- | CATGGCCCCTTCGA | -5' |
| | KpnI | HindIII |

Ligation 2 with the KpnI-HindIII* adaptor, in which the HindIII restriction site will not restore after ligation:

| 5'- | CGGGGG | -3' (SEQ ID NO: 50) |
|---|---|---|
| 3'- | CTAGGCCCCCTCGA | -5' |
| | KpnI | HindIII* |

Figure 16:
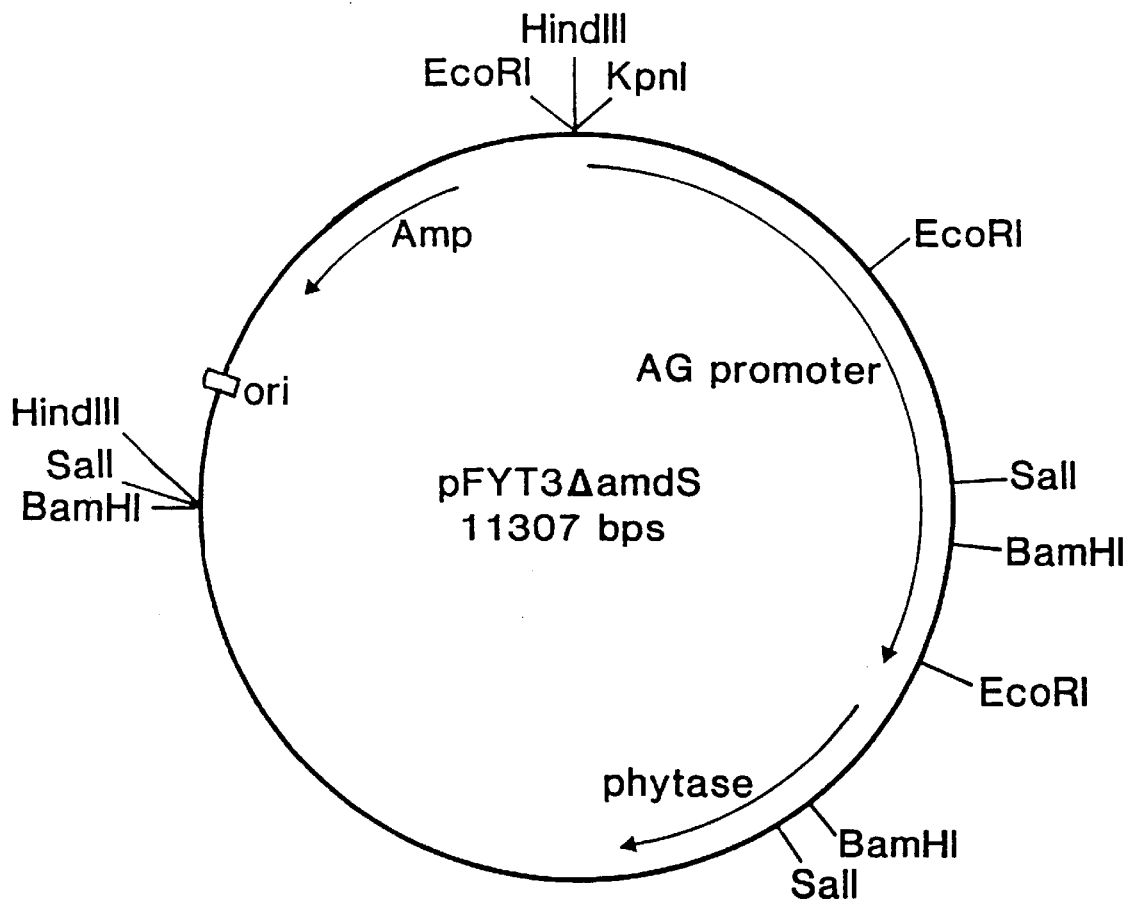
FIG. 16. Physical map of plasmid pFYT3ΔamdS.

Subsequently, ligation 1 is partially digested with HindIII. After removal of the amdS containing fragment by gel electrophoresis, the remaining DNA fragment is recircularized by ligation and transferred to *E. coli*. The obtained plasmid is denoted pFYT3ΔamdS (see FIG. 16).

Figure 17:
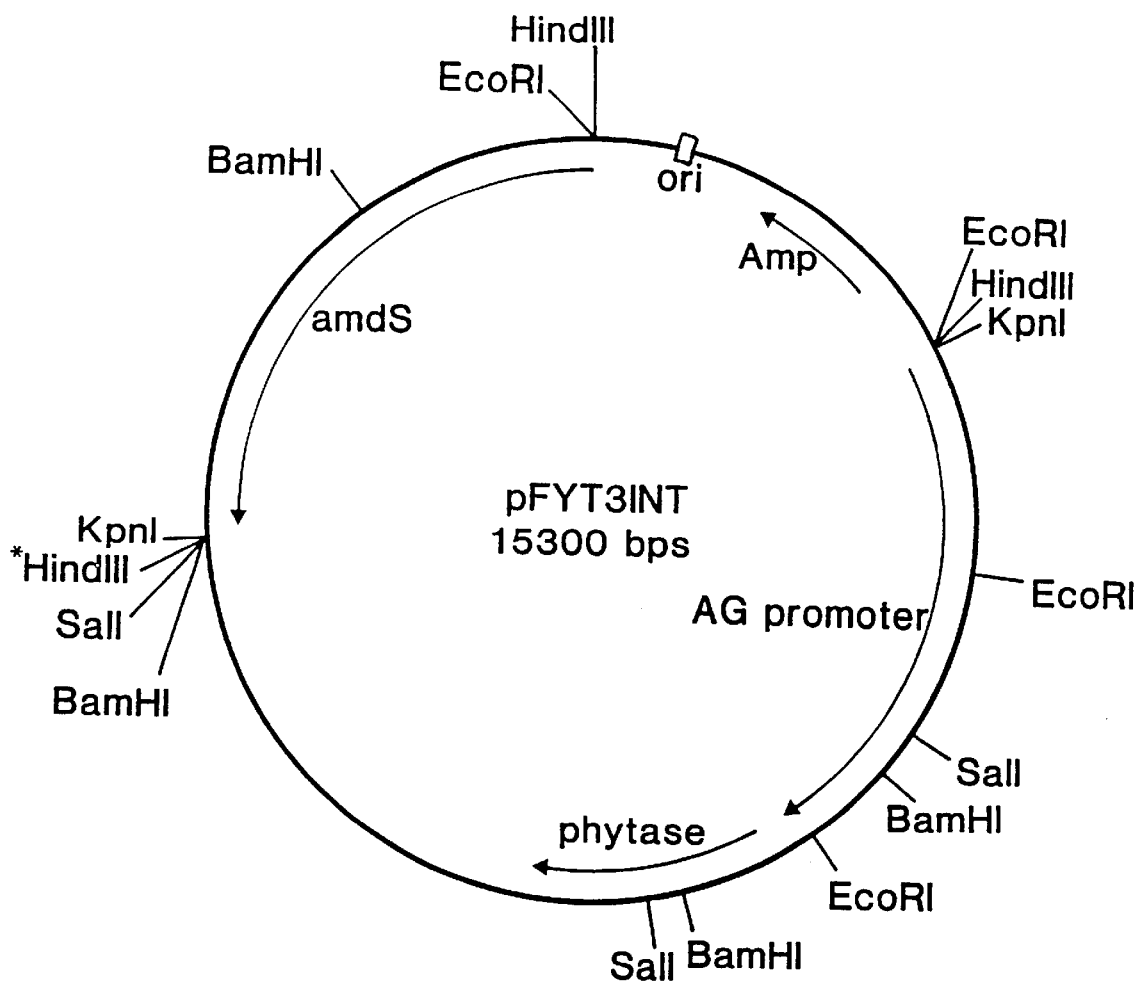
FIG. 17. Physical map of plasmid pFYT3INT.

Ligation 2 is also digested with HindIII and the 4 kb DNA HindIII/HindIII* fragment, containing the amdS gene, is isolated by gel electrophoresis, subsequently ligated to a partially HindIII digest of pFYT3ΔamdS and transferred to *E.coli*. The plasmid containing the amdS gene at the 3'end of the phytase gene is denoted pFYT3INT (see FIG. 17).

To introduce the approx. 6 kb SalI/HindIII DNA fragment of pAB6-1, containing the 3'-flanking AG sequence, pFYT3INT is partially digested with HindIII, ligated first to the adaptor:

| 5'- | AGCTAGGGGG | -3' SEQ ID NO: 51) |
|---|---|---|
| 3'- | TCCCCCAGCT | -5' (SEQ ID NO: 52) |
| | HindIII* | SalI |

Figure 18:
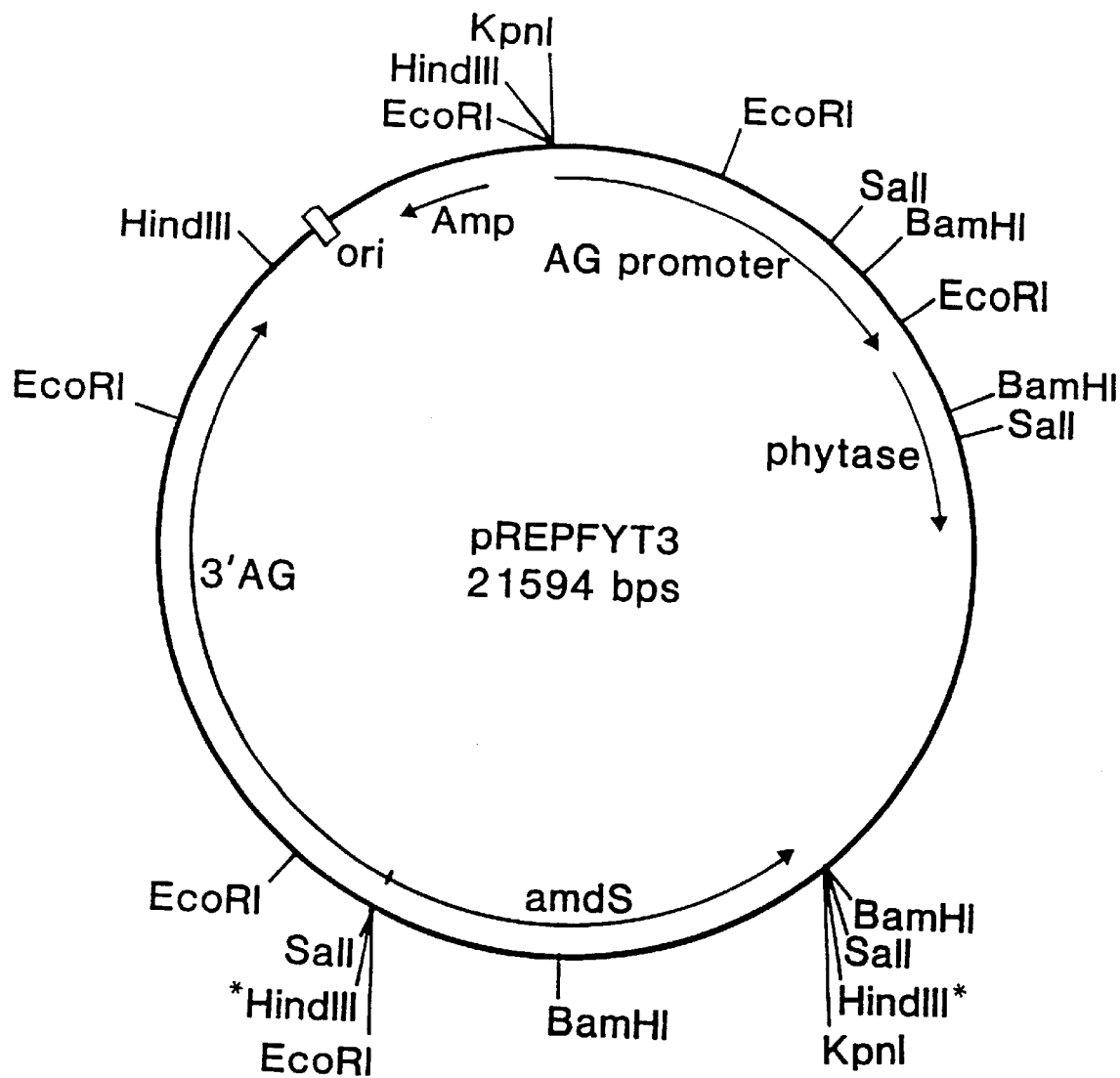
FIG. 18. Physical map of the phytase/AG replacement vector pREPFYT3.

(in which the HindIII* restriction site will not restore after ligation) and subsequently with the SalI/HindIII fragment of pAB6-1. After transformation to *E. coli*, the desired plasmid pREPFYT3, containing the 3' AG flanking sequence at the correct position, is obtained (FIG. 18).

Exression of Phytase in *A. niger* by AG Gene Replacement

Before transformation of *A. niger* with pREPFYT3, the *E. coli* sequences in the plasmid are removed by HindIII digestion and gelelectrophoresis. The *A. niger* strain CBS 513.88 is transformed with 10 μg DNA fragment by procedures as described in Example 9. Selection and growth of transformants is performed as described in Example 9. Only a minority of the selected transformants lose AG activity (approx. 20%). Southern analysis of chromosal DNA is performed on AG negative and phytase positive transformants to verify that the AG gene is indeed replaced by the phytase gene.

EXAMPLE 13
Conservation of the Phytase Gene in Different Species

To determine whether the phytase gene is highly conserved within microbial species, Southern analyses of chromosomal DNA from ten different species were performed with the *A. ficuum* phytase cDNA as probe.

These chromosomal DNA analyses were performed on species from filamentous fungi, yeasts and bacteria. As an example, only a limited number from each group were chosen: for filamentous fungi, *Penicillium chrysogenum* and *Aspergillus niger;* for yeast, *Saccharomyces cerevisiae* and *Kluyveromyces lactis;* and for the procaryotic organisms the Gram-positive species, *Bacillus subtilis, Clostridum thermocellum,* and *Streptomyces lividans* and as an example for a gram-negative bacterium *Pseudomonas aeruginosa.*

High molecular weight chromosomal DNA from these species was digested with PvuII and BamHI separately and subsequently electrophorized on a 0.7% agarose gel.

After transfer to nitrocellulose filters, the hybridization was performed overnight at low stringency (6×SSC; 50° C.) with a $^{32}$P-labeled 5'-phytase cDNA fragment (described in Example 8). Blots were washed in 6×SSC at room temperature and exposed to X-ray for 18 hours.

Figure 19A:
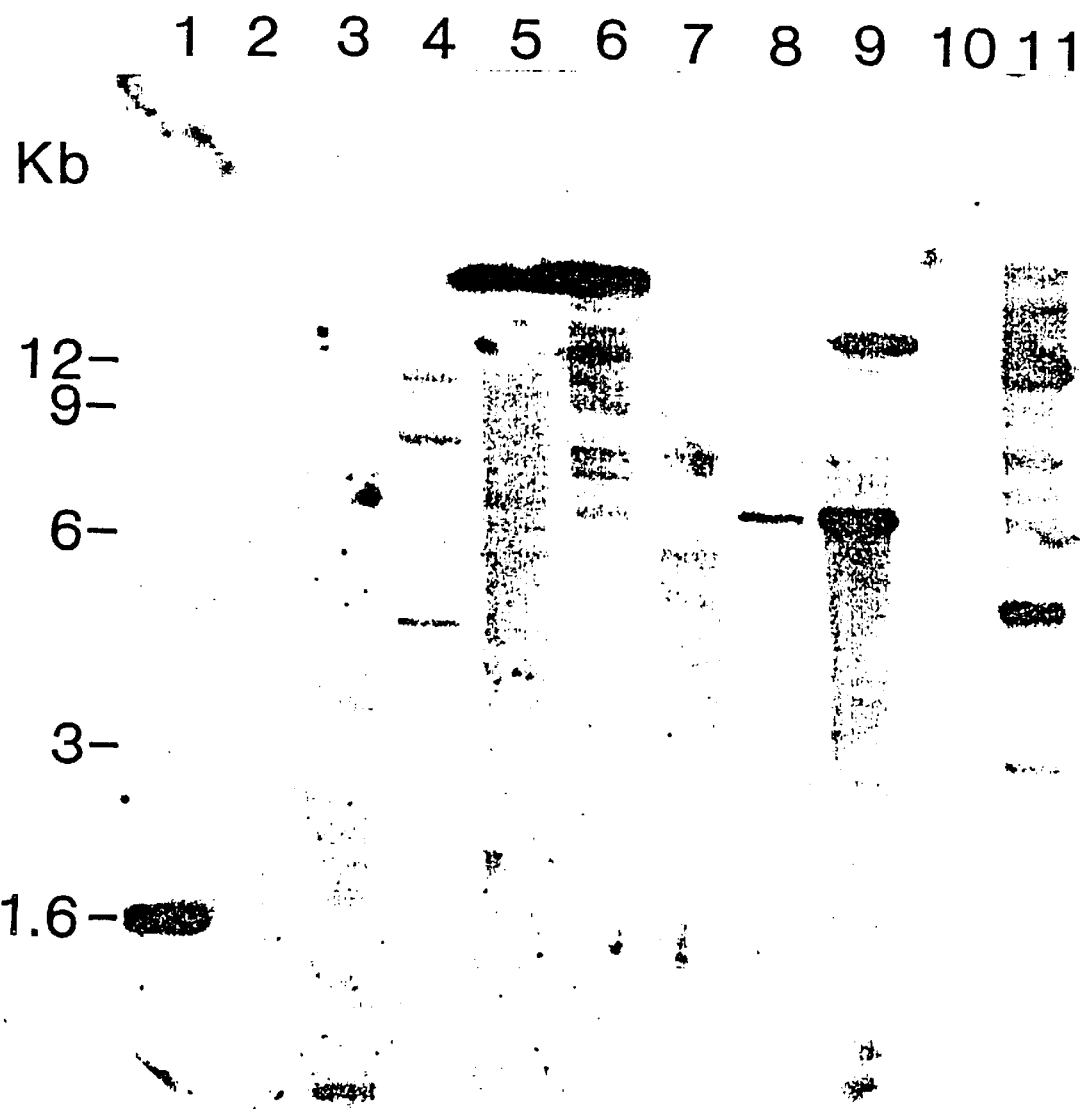
FIG. 19. Autoradiographs of chromosomal DNA, digested with PvuII (A) and BamHI (B) and hybridized with the $^{32}$P-labeled *A. ficuum* phytase cDNA as probe of the microbial species *S. cerevisiae* (lane 2); *B. subtilis* (lane 3); *K. lactis* (lane 4); *P. crysogenum* (lane 5); *P. aeruginosa* (lane 6); *S. lividans* (lane 7); *A. niger* 1 μg (lane 8); *A. niger* 5 μg (lane 9); blank (lane, 10); *C. thermocellum* (lane 11). Lane 1: marker DNA.
Figure 19B:
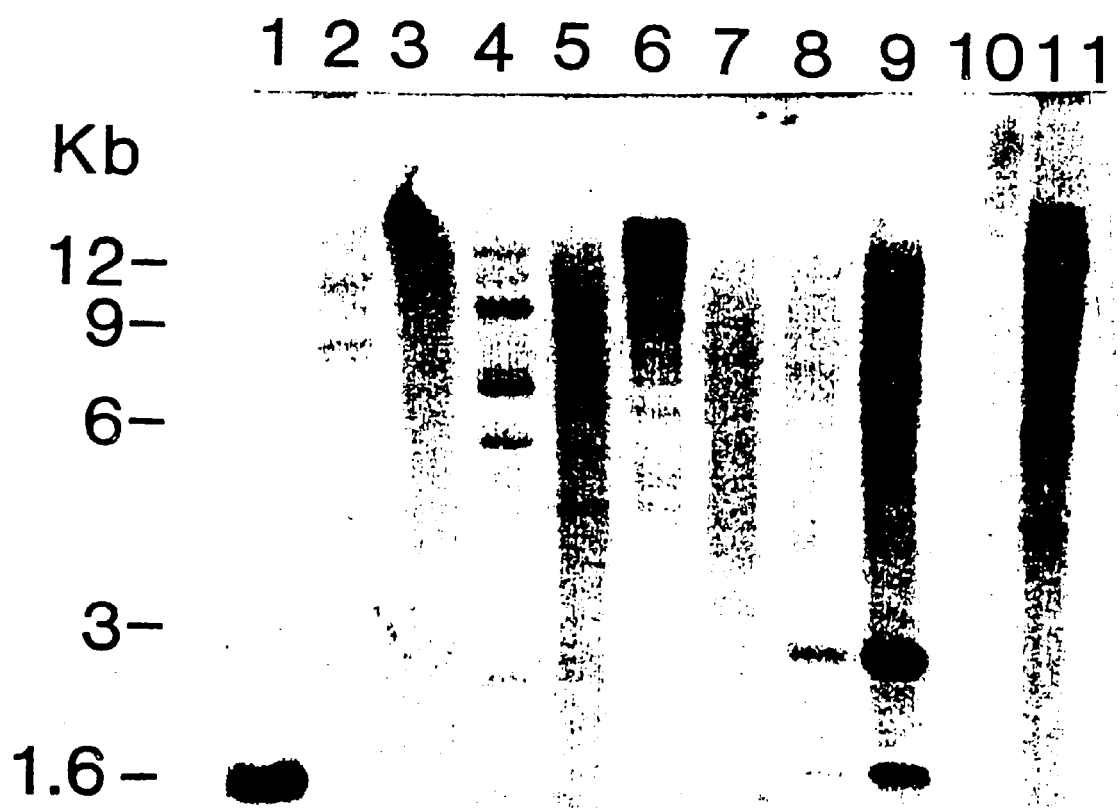

As shown in FIGS. 19 *a* and *b,* descrete bands are observed in almost every lane, predicting a high degree of homology of the phytase gene between microbial species.

What is claimed is:

1. A purified and isolated DNA molecule which:
   a) encodes a fungal phytase which catalyzes the liberation of inorganic phosphorus from myoinositol hexakis-phosphate; and
   b) encodes a phytase that is encoded by a nucleotide sequence that hybridizes under conditions of low stringency (6×SSC; 50° C. overnight) with a probe comprising nucleotide positions 210–1715 of SEQ ID NO:31.

2. A purified and isolated DNA molecule which:
   a) encodes a fungal phytase which catalyzes the liberation of inorganic phosphorus from myoinositol hexakis-phosphate; and
   b) encodes a phytase that is encoded by a nucleotide sequence that is selected from the group of nucleotide sequences consisting of:
      a nucleotide sequence encoding a phytase comprising the amino acid sequence of SEQ ID NO:32;
      a nucleotide sequence comprising the nucleotide sequence of SEQ ID NO:31; and
      a nucleotide sequence hybridizing to a cDNA probe comprising nucleotides 210–1715 of SEQ ID NO:31 under conditions of low stringency (6×SSC; 50° C. overnight), or a nucleotide sequence derived from said nucleotide sequence by degeneration of the genetic code.

3. A purified and isolated DNA molecule which is derived from the DNA molecule according to claim 1 by degeneration of the genetic code.

4. The purified and isolated DNA molecule defined in claim 2 wherein said nucleotide sequence is selected from the group of nucleotide sequences consisting of:
   a nucleotide sequence encoding a phytase comprising the amino acid sequence of SEQ ID NO:32;
   a nucleotide sequence comprising the nucleotide sequence of SEQ ID NO:31; and
   a nucleotide sequence isolated from a filamentous fungus hybridizing to a cDNA probe comprising nucleotides 210–1715 of SEQ ID NO:31 under conditions of low stringency (6×SSC; 50° C. overnight).

5. A recombinant expression system which is useful, when contained in a host cell, for expressing a nucleotide sequence encoding a fungal phytase which catalyzes the liberation of inorganic phosphate from myoinositol hexakis-phosphate, and wherein said phytase is encoded by a nucleotide sequence that hybridizes under conditions of low stringency (6×SSC; 50° C. overnight) with a probe comprising nucleotide positions 210–1715 of SEQ ID NO:31 said expression system comprising a nucleotide sequence encoding said phytase, or a nucleotide sequence derived therefrom by degeneration of the genetic code, operably linked to control sequences compatible with said host cell.

6. The expression system of claim 5, wherein said nucleotide sequence encoding said protein further includes a sequence encoding a secretory leader sequence operably linked to said protein.

7. The expression system of claim 6, wherein said leader sequence comprises the 18-amino acid AG leader sequence.

8. The expression system of claim 5 wherein said control sequence includes an AG promoter.

9. A recombinant vector comprising the expression system of claim 5.

10. A recombinant expression system which is useful, when contained in a host/cell, for expressing a nucleotide sequence encoding a fungal phytase which catalyzes the liberation of inorganic phosphate from myoinositol hexakis-phosphate, and
    wherein said phytase is encoded by a nucleotide sequence that is selected from the group of nucleotide sequences consisting of:
       a nucleotide sequence encoding a phytase comprising the amino acid sequence of SEQ ID NO:32;
       a nucleotide sequence comprising the nucleotide sequence of SEQ ID NO:31; and
       a nucleotide sequence hybridizing to a cDNA probe comprising nucleotides 210–1715 of SEQ ID NO:31 under conditions of low stringency (6×SSC; 50° C., overnight);
    said expression system comprising a nucleotide sequence encoding said phytase, or a nucleotide sequence derived therefrom by degeneration of the genetic code, operably linked to control sequences compatible with said host cell.

11. The expression system of claim 10, wherein said nucleotide sequence encoding said protein further includes a sequence encoding a secretory leader sequence operably linked to said protein.

12. The expression system of claim 11, wherein said leader sequence comprises the 18-amino acid AG leader sequence.

13. The expression system of claim 10 wherein said control sequence includes an AG promoter.

14. A recombinant vector comprising the expression system of claim 10.

15. A recombinant microbial host cell comprising the expression system of claim 5.

16. The cell of claim 5 which is a bacterial, yeast or fungal cell.

17. The cell of claim 16 which is of a genus selected from the group consisting of Aspergillus, Trichoderma, Penicillium, Mucor, Bacillus, Kluyveromyces and Saccharomyces.

18. The cell of claim 17, which is of a species selected from the group consisting of *Aspergillus niger, Aspergillus ficuum, Aspergillus awamori, Aspergillus oryzae, Trichoderma reesei, Mucor miehei, Kluyveromyces lactis, Saccharomyces cerevisiae, Bacillus subtilis* and *Bacillus licheniformis*.

19. A recombinant microbial host cell comprising the expression system of claim 10.

20. The cell of claim 10 which is a bacterial, yeast or fungal cell.

21. The cell of claim 20 which is of a genus selected from the group consisting of Aspergillus, Trichoderma, Penicillium, Mucor, Bacillus, Kluyveromyces and Saccharomyces.

22. The cell of claim 21, which is of a species selected from the group consisting of *Aspergillus niger, Aspergillus ficuum, Aspergillus awamori, Aspergillus oryzae, Trichoderma reesei, Mucor miehei, Kluyveromyces lactis, Saccharomyces cerevisiae, Bacillus subtilis* and *Bacillus licheniformis*.

23. A method to express a nucleotide sequence encoding a fungal phytase which phytase catalyzes the liberation of inorganic phosphate from myoinositol hexakis-phosphate, which method comprises (a) culturing the cells of claim 15 under conditions wherein said phytase-encoding nucleotide sequence is expressed to produce said phytase, and (b) recovering the phytase produced from the culture.

24. A method to express a nucleotide sequence encoding a fungal phytase which phytase catalyzes the liberation of inorganic phosphate from myoinositol hexakis-phosphate, which method comprises (a) culturing the cells of claim 19 under conditions wherein said phytase-encoding nucleotide sequence is expressed to produce said phytase, and (b) recovering said phytase produced from said culture.

* * * * *

UNITED STATES PATENT AND TRADEMARK OFFICE
CERTIFICATE OF CORRECTION

PATENT NO. : 6,350,602 B1 Page 1 of 1
DATED : February 26, 2002
INVENTOR(S) : Robert F. M. Van Gorcom et al.

It is certified that error appears in the above-identified patent and that said Letters Patent is hereby corrected as shown below:

<u>Title page, Item [54] and Column 1, lines 1 & 2,</u>
The Title should be changed to: -- CLONING AND EXPRESSION OF MICROBIAL PHYTASE --

Signed and Sealed this

Tenth Day of December, 2002

JAMES E. ROGAN
*Director of the United States Patent and Trademark Office*